US012590317B2

(12) United States Patent
Johnson et al.

(10) Patent No.: US 12,590,317 B2
(45) Date of Patent: Mar. 31, 2026

(54) POLYNUCLEOTIDES AND METHODS FOR TRANSFERRING RESISTANCE TO ASIAN SOYBEAN RUST

(71) Applicants: PIONEER HI-BRED INTERNATIONAL, INC., Johnston, IA (US); TWO BLADES FOUNDATION, Evanston, IL (US); UNIVERSIDADE FEDERAL DE VICOSA, Vicosa (BR)

(72) Inventors: Ebony Johnson, Johnston, IA (US); Shawn Thatcher, Johnston, IA (US); Karen E. Broglie, Johnston, IA (US); Peter Van-Esse, Evanston, IL (US); Cintia Goulart Kawashima, Evanston, IL (US); Jonathan Jones, Evanston, IL (US); Sergio Hermino Brommonschenkel, Vicosa (BR)

(73) Assignees: PIONEER HI-BRED INTERNATIONAL, INC., Johnston, IA (US); TWO BLADES FOUNDATION, Evanston, IL (US); UNIVERSIDADE FEDERAL SE VICOSA, Vicosa (BR)

( * ) Notice: Subject to any disclaimer, the term of this patent is extended or adjusted under 35 U.S.C. 154(b) by 60 days.

(21) Appl. No.: 18/259,006

(22) PCT Filed: Dec. 20, 2021

(86) PCT No.: PCT/US2021/064348
§ 371 (c)(1),
(2) Date: Jun. 22, 2023

(87) PCT Pub. No.: WO2022/140257
PCT Pub. Date: Jun. 30, 2022

(65) Prior Publication Data
US 2024/0043861 A1 Feb. 8, 2024

Related U.S. Application Data

(60) Provisional application No. 63/130,261, filed on Dec. 23, 2020.

(51) Int. Cl.
*C12N 15/82* (2006.01)
*C07K 14/415* (2006.01)
*C12N 5/04* (2006.01)
*C12Q 1/6876* (2018.01)

(52) U.S. Cl.
CPC ........ *C12N 15/8282* (2013.01); *C07K 14/415* (2013.01); *C12N 5/04* (2013.01); *C12Q 1/6876* (2013.01); *C12Q 2600/13* (2013.01)

(58) Field of Classification Search
None
See application file for complete search history.

(56) References Cited

U.S. PATENT DOCUMENTS

| 2004/0031072 A1 | 2/2004 | La Rosa | |
| 2010/0037352 A1 | 2/2010 | Alexandrov | |
| 2018/0103600 A1* | 4/2018 | Rairdan et al. | ......... A01H 1/04 |

FOREIGN PATENT DOCUMENTS

WO 2021/022022 A1 2/2021

OTHER PUBLICATIONS

Yu et al., Fine mapping of the Asian soybean rust resistance gene Rpp2 from soybean PI 230970, 2015, Theoretical and Applied Genetics, vol. 128, pp. 387-396. (Year: 2015).*
Varshney et al., Draft genome sequence of pigeonpea (*Cajanus cajan*), an orphan legume crop of resource-poor farmers, 2012, Nat. Biotechnol. vol. 30(1), pp. 83-89. (Year: 2012).*
Whitham et al., Molecular Soybean-Pathogen Interactions, 2016, Annual Review of Phytopathology, vol. 54, pp. 443-468 (Year: 2016).*
Anonymous: "Glycine max protein SEQ ID No. 156669", XP093216278, Database accession No. AFP65491, Oct. 18, 2007.
Extended European Search Report for EP 21911972.4, dated Nov. 8, 2024.
PCT Search Report and Written Opinion prepared for PCT Application No. PCT/US2021/064348, completed Apr. 4, 2022.
GenBank_EZ650441, TSA: Cajanus cajan cultivar Asha contig02577. Asha mRNA sequence. Gen Bank Accession No. EZ650441. Mar. 10, 2011. online). [Retrieved on Feb. 24, 2022. Retrieved from the Internet: < URL: https://www.ncbi.nlm.ni[h.gov/nuccore/EZ650441.
UniProtKB_V788Z3, UniProtKB—V788Z3 (V788Z3_PHAVU), Uncharacterized protein. UniProtKB Accession No. V7B8Z3. Last Modified: Feb. 19, 2014. [online]. [Retrieved on Mar. 31, 2022). Retrieved from the Internet:< URL: https://www.uniprot.org/uniproW7B8Z3.
GenBank_EZ676744, TSA: Cajanus cajan cultivar Asha contig28880. Asha mRNA sequence. Gen Bank Accession No. EZ676744. Mar. 10, 2011. [online]. [Retrieved on Feb. 24, 2022]. Retrieved from the Internet: < URL. https://www.ncbi.nlm.nih.gov/nuccore/EZ676744.
Kankanala, et al., "Genomics of Plant Disease Resistance in Legumes." 2019, Front Plant Sci., vol. 10, No. 1346, pp. 1-20.
Langenbach, et al., "Fighting Asian Soybean Rust." 2016, Front Plant Sci., vol. 7, No. 797, pp. 1-13.
Mammadov, et al., "Wild Relatives of Maize, Rice, Cotton, and Soybean: Treasure Troves for Tolerance to Biotic and Abiotic Stresses." 2018, Front Plant Sci., vol. 9, No. 886, pp. 1-21.

* cited by examiner (Continued)

*Primary Examiner* — Bratislav Stankovic
*Assistant Examiner* — Christina L Meadows
(74) *Attorney, Agent, or Firm* — Barnes & Thornburg LLP

(57) ABSTRACT

Disclosed herein are compositions and methods for improving or enhancing pathogen resistance in legume plants. Compositions comprising polypeptides encoded by the CcRpp2-R1 and CcRpp2-R3 polynucleotides disclosed herein are useful in improving resistance in legumes to Asian Soybean Rust (ASR). Methods of using CcRpp2-R1 and CcRpp2-R3 genes to make transgenic ASR-resistant legume plants are also disclosed.

21 Claims, 1 Drawing Sheet

Specification includes a Sequence Listing.

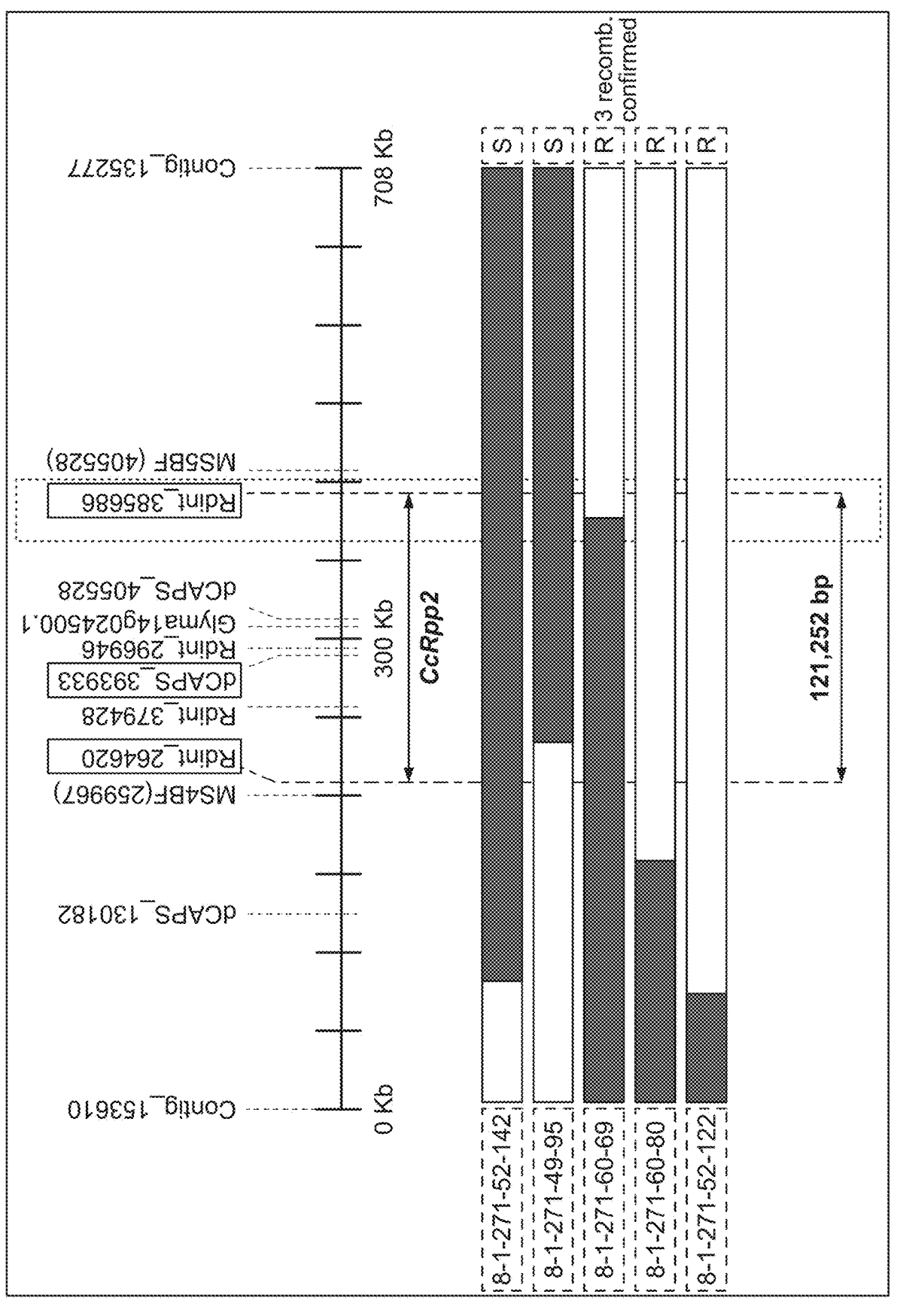

SEQUENCE LISTING

```
<160> NUMBER OF SEQ ID NOS: 60

<210> SEQ ID NO 1
<211> LENGTH: 1026
<212> TYPE: DNA
<213> ORGANISM: Cajanus cajan
```

<400> SEQUENCE: 1
atgaagatgg gggatgaaaa agcgaagtgg tgctacgatg tttttctggc tttcagaggg        60
caagacacgc gctacaactt caccggtaat ctctacgatg ctttgcggcg cgctagaatc       120
agtactttca tggatgacag tgccttgaag ggtggtgacc aaatctcagc ctctcttctc       180
agagcgcttg aagcgtccag gatttcaatc gttgttctct ccgaaaacta tgcgtttttcc      240 acgtggtgcc ttgaagaact tgtgaacatc gtccggtgta gaaggaccta tgcccaagtc       300
gttttgccaa tctttttacga cgtggatccc tccgatgtaa ggaagcagac aggtaggttt      360
gatgaagcca tggtccgaca tatacgtcgc ttcggagata aatcggagaa gataaaagag       420
tggaggtcag ctttgactga aatcgccaac ttgcgtggat gggatttccg atatggggac       480
cgatatgaat ataaactcat ccaagacatt gttagatggg tcaccaacac tgtgtcccgc       540
tatagcattt ttctgagttt ttgtggaaaa gatacccgct actcttttac aggttttctc       600
tacaatgctt tgtctcggag tggattccaa accttcatga cgatggggga ccacatttca       660
caatctaata ttgaagttga agcgattgaa aattcaaggc tttccatcat tgtatttttct      720 gaaaactatg cacgttcctc ctcgtgtctt gatgagcttc tgacgatcct cgagtgtatg       780
aagctcaaaa accaactagt ttggcctgtc ttttacaaag tggaaccatc ggatttaagg       840
catcaaagaa atagttgggg tgaagccatg attgaacatg aaaacatgtt gggcaacgac       900
tctcagaagg tgcagaaatg gaggttagct ttacttgaag tcgccaactt gaaagggtgg       960
caccacaaaa ccgggtacga atatgaatta attgaaaaaa ttgtggaaat ggccactaaa      1020
atttaa                                                                1026

<210> SEQ ID NO 2
<211> LENGTH: 341
<212> TYPE: PRT
<213> ORGANISM: Cajanus cajan

<400> SEQUENCE: 2

Met Lys Met Gly Asp Glu Lys Ala Lys Trp Cys Tyr Asp Val Phe Leu
1               5                   10                  15

Ala Phe Arg Gly Gln Asp Thr Arg Tyr Asn Phe Thr Gly Asn Leu Tyr
            20                  25                  30

Asp Ala Leu Arg Arg Ala Arg Ile Ser Thr Phe Met Asp Asp Ser Ala
        35                  40                  45

Leu Lys Gly Gly Asp Gln Ile Ser Ala Ser Leu Leu Arg Ala Leu Glu
    50                  55                  60

Ala Ser Arg Ile Ser Ile Val Val Leu Ser Glu Asn Tyr Ala Phe Ser
65                  70                  75                  80

Thr Trp Cys Leu Glu Glu Leu Val Asn Ile Val Arg Cys Arg Arg Thr
                85                  90                  95

Tyr Ala Gln Val Val Leu Pro Ile Phe Tyr Asp Val Asp Pro Ser Asp
            100                 105                 110

Val Arg Lys Gln Thr Gly Arg Phe Asp Glu Ala Met Val Arg His Ile
        115                 120                 125

Arg Arg Phe Gly Asp Lys Ser Glu Lys Ile Lys Glu Trp Arg Ser Ala
    130                 135                 140

Leu Thr Glu Ile Ala Asn Leu Arg Gly Trp Asp Phe Arg Tyr Gly Asp
145                 150                 155                 160

Arg Tyr Glu Tyr Lys Leu Ile Gln Asp Ile Val Arg Trp Val Thr Asn
                165                 170                 175

```
Thr Val Ser Arg Tyr Ser Ile Phe Leu Ser Phe Cys Gly Lys Asp Thr
            180                 185                 190

Arg Tyr Ser Phe Thr Gly Phe Leu Tyr Asn Ala Leu Ser Arg Ser Gly
            195                 200                 205

Phe Gln Thr Phe Met Asn Asp Gly Asp His Ile Ser Gln Ser Asn Ile
            210                 215                 220

Glu Val Glu Ala Ile Glu Asn Ser Arg Leu Ser Ile Ile Val Phe Ser
225                 230                 235                 240

Glu Asn Tyr Ala Arg Ser Ser Ser Cys Leu Asp Glu Leu Leu Thr Ile
                245                 250                 255

Leu Glu Cys Met Lys Leu Lys Asn Gln Leu Val Trp Pro Val Phe Tyr
            260                 265                 270

Lys Val Glu Pro Ser Asp Leu Arg His Gln Arg Asn Ser Trp Gly Glu
            275                 280                 285

Ala Met Ile Glu His Glu Asn Met Leu Gly Asn Asp Ser Gln Lys Val
            290                 295                 300

Gln Lys Trp Arg Leu Ala Leu Leu Glu Val Ala Asn Leu Lys Gly Trp
305                 310                 315                 320

His His Lys Thr Gly Tyr Glu Tyr Glu Leu Ile Glu Lys Ile Val Glu
                325                 330                 335

Met Ala Thr Lys Ile
            340
```

```
<210> SEQ ID NO 3
<211> LENGTH: 1035
<212> TYPE: DNA
<213> ORGANISM: Cajanus cajan

<400> SEQUENCE: 3
atgttgatgg cgaatggtgc caccgaggaa caaaggagca gcaacaagta cgatgttttt     60
ctcagttttg caggtataga caaccgctac accttcaccg gtaatctcta caacgccttg    120
cgcagcaaga gaatcaacac cttttttcaat gaaaatggtg ataccaaagc tcttgaagca    180
attaaagaat cgaggatttc gatcgttgtg ctctccccaa actatgcatc tcctcatgg     240 aggcttgatg aacttgtgac catccttgag tgtatgaaaa ccaagggcca actggtgtgg    300
cccatctatt acgaagtgga accgtcggaa gtaaggcgtc agagcggtat ctatggcgaa    360
gccatgtctg aatttgaaca aaaatttgga catgagagtg agatggtgtg gaaatggagg    420
agtgctttga ctgaagtcag cagcttgagt ggatgggttt acgaaactgg gtacgaatat    480
aaattcatcc gaaagattgt cgattagca gtggaatctt gccccgata tgatgttttc     540 ctgagtttta gcggagaaga tactcgctac tctttcacag gttttctcta taatgccttt    600
aggcgggagg ggttcaatat cttcatggat gatgagggat tggagggtgg caaccaaatt    660
tcagaaactc tcatgcgagc aattgaaatg tcaagacttt caattgtcgt cttctctgaa    720
aactatgcat attccacgtg gtgtcttgat gaacttgcca agatcatcga gtgcaagaag    780
accaagaatc agatggtttg gccaatattt cactatgtgg aaaagtctga tgtgtgcaat    840
caaacaaaaa gttatggtga agccatggct gcacatgaag aaagatttgg aaaggactct    900
gagaaggtgc aaaactggag gtctgctttg tctgaaattg ccaacttgga tggacaccat    960
ttcagagaaa atgagtacca atatgaattt atcgaaaggg ttgtggatct ggccattgct   1020
atcgggaatc agtag                                                    1035
```

<210> SEQ ID NO 4
<211> LENGTH: 344
<212> TYPE: PRT
<213> ORGANISM: Cajanus cajan

<400> SEQUENCE: 4

```
Met Leu Met Ala Asn Gly Ala Thr Glu Glu Gln Arg Ser Ser Asn Lys
1               5                   10                  15

Tyr Asp Val Phe Leu Ser Phe Ala Gly Ile Asp Asn Arg Tyr Thr Phe
                20                  25                  30

Thr Gly Asn Leu Tyr Asn Ala Leu Arg Ser Lys Arg Ile Asn Thr Phe
            35                  40                  45

Phe Asn Glu Asn Gly Asp Thr Lys Ala Leu Glu Ala Ile Lys Glu Ser
        50                  55                  60

Arg Ile Ser Ile Val Val Leu Ser Pro Asn Tyr Ala Ser Ser Ser Trp
65                  70                  75                  80

Arg Leu Asp Glu Leu Val Thr Ile Leu Glu Cys Met Lys Thr Lys Gly
                85                  90                  95

Gln Leu Val Trp Pro Ile Tyr Tyr Glu Val Glu Pro Ser Glu Val Arg
                100                 105                 110

Arg Gln Ser Gly Ile Tyr Gly Glu Ala Met Ser Glu Phe Glu Gln Lys
            115                 120                 125

Phe Gly His Glu Ser Glu Met Val Trp Lys Trp Arg Ser Ala Leu Thr
        130                 135                 140

Glu Val Ser Ser Leu Ser Gly Trp Val Tyr Glu Thr Gly Tyr Glu Tyr
145                 150                 155                 160

Lys Phe Ile Arg Lys Ile Val Arg Leu Ala Val Glu Ser Leu Pro Arg
                165                 170                 175

Tyr Asp Val Phe Leu Ser Phe Ser Gly Glu Asp Thr Arg Tyr Ser Phe
                180                 185                 190

Thr Gly Phe Leu Tyr Asn Ala Phe Arg Arg Glu Gly Phe Asn Ile Phe
            195                 200                 205

Met Asp Asp Glu Gly Leu Glu Gly Gly Asn Gln Ile Ser Glu Thr Leu
        210                 215                 220

Met Arg Ala Ile Glu Met Ser Arg Leu Ser Ile Val Val Phe Ser Glu
225                 230                 235                 240

Asn Tyr Ala Tyr Ser Thr Trp Cys Leu Asp Glu Leu Ala Lys Ile Ile
                245                 250                 255

Glu Cys Lys Lys Thr Lys Asn Gln Met Val Trp Pro Ile Phe His Tyr
                260                 265                 270

Val Glu Lys Ser Asp Val Cys Asn Gln Thr Lys Ser Tyr Gly Glu Ala
            275                 280                 285

Met Ala Ala His Glu Glu Arg Phe Gly Lys Asp Ser Glu Lys Val Gln
        290                 295                 300

Asn Trp Arg Ser Ala Leu Ser Glu Ile Ala Asn Leu Asp Gly His His
305                 310                 315                 320

Phe Arg Glu Asn Glu Tyr Gln Tyr Glu Phe Ile Glu Arg Val Val Asp
                325                 330                 335

Leu Ala Ile Ala Ile Gly Asn Gln
            340
```

<210> SEQ ID NO 5
<211> LENGTH: 1125
<212> TYPE: DNA
<213> ORGANISM: Arachis duranensis -continued

```
<400> SEQUENCE: 5
atgggtctgc aactgcaacc atcccactcg tcttcttcct cttcctggca ttgggaatac      60
gatgtgttcc tcaacttcag aggccctgac actcgctacg gtttcacagg ctatctctac     120
aaagctctct gtgacaaggg aattcatgcc ttcatggatt ttgacgatat tcacagaggg     180
aatgaaatct ccgcatcact tatgaaggca attgaagcgt ccaggattgc gattcttgtg     240
ttctctaaga actatgctga atcttcttat tgcctaaacg aactggtgaa gatcatggag     300
tgctctcagc gtcatggcca gtttgttttg ccagtatttt acagcgtcga tcctagcgtc     360
gtgcggcatc agaaaggtat ttatgaggag gcattggcta agactggaag gacgtttgag     420
catgccatgg acagagtgca agatggagg actgccatgg ctgacgcagc taacttgtct     480
ggcttgcatt ttaaagggga tggatacgga tatgagtttg ttgagaaaat tgttgaacaa     540
gtgtcaaggg tgattaaacg tgttggtgat tatccagttg aactagagtc ccaggaacaa     600
gcttcctact cgtctttggc tccttgcttg agcaatggat ggaaatacga tgtgttcctc     660
agcttcagag cactgatac tcgatttggt ttcactggca atctctacaa tgttctttgt     720
ggcaagggaa tccacacctt catggatgat gaggctcttc atagagggaa tgaaatctca     780
ggaacacttg acaggcaat tgaagggtcc aagattgcta tacttgtgtt ctcgaagaac     840
tatgcttatt cttcttattg cttagatgaa cttgttaaga tcatgaagtg ctctcaatct     900
aattcccagt gtgttttgcc ggttttttat aacgtggatc ctcctcacgt tcgacatcag     960
cgtggtagtt atgaggaagc actggctaag catgaggaga ggttcaagaa tgatgtagac    1020
agactgcgag attggagggc tgctctgcat caggcagcta acttaacagg cttccatttc    1080
aaaggacaac caacgcaaca cttcaaaagt caaagcagaa actga                     1125

<210> SEQ ID NO 6
<211> LENGTH: 1455
<212> TYPE: DNA
<213> ORGANISM: Arachis hypogaea

<400> SEQUENCE: 6
atgggtctgc aaccatccca ctcttcttct tcctttttcct ggcattggga atacgatgtg      60
ttcctcaact tcagaggccc tgacactcgc tacggtttca caggctatct ctacaaagct     120
ctctgtgaca agggaattcg tgccttcatg gattttggcg atattcacag agggaatgaa     180
atctccgcat ctcttatgaa ggcaattgaa gcgtccagga ttgcgattct tgtgttctct     240
aagaactatg ctgaatcttc ttattgccta aacgaactag tgaagatcat ggagtgctct     300
cagcgtcatg gccagtttgt tttgccagtg ttttacggca tcgatcctag cgtcgtgcgg     360
catcagaaag gtatttacga ggaggcactg gctaagactg aaggacgtt tgagcatgcc     420 atggacagag tgcaaagatg gaggactgcc atggctgacg cagctaactt gtctggcttg     480
cattttaaag gggatggata cggatatgaa tttgttgaga aaattgttga caagtgtca     540 agggtgatta aacgtgttgg tgattatcca attgaactgg agtcccaaga caagcttcc     600 tactcctctt tggctccttc ctcgagcaat ggatggaaat acgatgtgtt cctcagcttc     660
agaggtacta tactcgatt tggtttcact ggcaatctct acaatgttct ttgtggcaag     720
ggaatccaca ccttcatgga tgatgaggct cttcatagag ggaatgaaat ctcaggaaca     780
cttgacaagg caattgaagg tccaagatt gctatacttg tgttctcgaa gaactatgct     840
tattcttctt attgcttaga tgaacttgtt aagatcatga agtgctctca atctcattcc     900
cagtgtgttt tgccggtttt ttataacgtg gatcctcctc acgttcgaca tcagcatggt     960
```

```
agttatgagg aagcactggc taagcatgag gagaggttca gtgatgtaga gagactgcga      1020
gattggaggg ctgctctgca tcaggcagct aacttaacag gcttccattt caaagggaat      1080
gagtatgaac atgagtttat tggaaagatc gttcgagtgg tgtcgcggaa tattagaaat      1140
attgcttctc ctgtggtagg aatccaagaa aatggtggta cagaagcaga gtctcttctc      1200
caagacaacc aacgcaacaa ttcaaaagtc aaagcagaaa ctgaagctaa tgttgaaaac      1260
ttcatggaag tcgatgtgtt tgagaagtct gtaggtgttc agttggaatc gttgaagcga      1320
aagaagcgag aacttgaagg gcaaatccgt gccattaatg accagataac agaattccaa      1380
agaaagacag ttgcaaagag aaaaaaagcg tttgacagtg gaaaaaaatg ccaagttgaa      1440
agcatagtta catga                                                       1455

<210> SEQ ID NO 7
<211> LENGTH: 771
<212> TYPE: DNA
<213> ORGANISM: Cajanus cajan

<400> SEQUENCE: 7
atgaaaacca agggccaact ggtgtggccc atctattacg aagtggaacc gtcggaagta        60
aggcgtcaga gcggtatcta tggcgaagcc atgtctgaat ttgaacaaaa atttggacat       120
gagagtgaga tggtgtggaa atggaggagt gctttgactg aagtcagcag cttgagtgga       180
tgggtttacg aaactgggta tcattcgtac gaatataaat tcatccgaaa gattgtgcga       240
ttagcagtgg aatctttgcc ccgatatgat gttttcctga gttttagcgg agaagatact       300
cgctactctt tcacaggttt tctctataat gcctttaggc gggaggggtt caatatcttc       360
atggatgatg agggattgga gggtggcaac caaatttcag aaactctcat gcgagcaatt       420
gaaatgtcaa gactttcaat tgtcgtcttc tctgaaaact atgcatattc cacgtggtgt       480
cttgatgaac ttgccaagat catcgagtgc aagaagacca agaatcagat ggtttggcca       540
atatttcact atgtggaaaa gtctgatgtg tgcaatcaaa caaaaagtta tggtgaagcc       600
atggctgcac atgaagaaag atttggaaag gactctgaga aggtgcaaaa ctggaggtct       660
gctttgtctg aaattgccaa cttggatgga caccatttca gagaaaatga gtaccaatat       720
gaatttatcg aaagggttgt ggatctggcc attgctatcg ggaatcagta g               771

<210> SEQ ID NO 8
<211> LENGTH: 5211
<212> TYPE: DNA
<213> ORGANISM: Cercis canadensis

<400> SEQUENCE: 8
atggcaaatt ttggagaagc atcttctagt tcctcctcca aacccaggta cacctatgac        60
gttttcctga gttttagagg tgaagatacc cgcaacacat ttaccggtaa tctctatgat       120
gctctgtgcc aaaggggttt caacaccttc atagatgatg acgggttgga gagaggccaa       180
caaatttcat atgctcttat caatgcaatt gaagaatcaa aggtttccat tgttgtgttc       240
tccgaaaact atgcatcttc cccgtggtgc cttgatgaac ttgtcaagat ccttgaatgc       300
aagaaggaaa agggtcaaat agtttggcca atttttttaca aggttgaacc tgccgatgta       360
agagatcaga agaacagcta cgaagcagca atggcaaaac atgaaagtag gttcagcaat       420
gacaaagtga caaatggag gtcagctttg aaagaagcag ctaacttgtc aggatcggaa       480
tacaaaactg ggtacgaata caaatttatc accaacatta tagaagtcgc ctccactaaa       540
```

-continued

```
ttacatgata agcatttata tattggtgag cacattgttg gactcaagtc tcgtttaaaa      600
gaagtaaagt caattttaga tattggatct cacaatacta ttggcatggt gggaattcat      660
ggaactggtg gaataggaaa aaccacactt gccaaggttt tgtataactt gattgttgat      720
caatttcact gtgcatgttt tcttgaatct gtcagagaag gttcaaaatg ttccatggac      780
cttgtaagtc tgcaaaagaa acttctatcc cagatattta ggaaggaaaa tttcaacttg      840
ggcaatgttg atgaaggtgc aaatataata aaacataggc ttcgcaatag aagagttctc      900
cttgtgcttg atgatgttgt taaggggggag caattaaaaa aattggctgg gggatgtgat      960
tggtttggtc ctggtagtag gatcatcata acaacaaggg ataaacattt gctaattgct     1020
catggagtag aaaaaatata tgaaatgaac gagctagatg atgataaagc tcttgaactc     1080
ttttgttgga aggccttcaa aatgagtgaa cctacagaag gctttgtgga tatatcctat     1140
aagataataa aatatgccaa gggccttcca ttggctttaa atgtaatagg ttccaatttg     1200
tttggtagga gttaaaaggc atgggaatct gcatcggata aatataagag gattctggac     1260
aaaggtattc atgacatact tagagtaagc tatgatagct tggaggatga tcagaaaagc     1320
atttttctcg atattgcttg tttcttcaaa ggggagagat tggaagatgt tgaaaagata     1380
ctagatgctt gtgatctctc tccgcaatat aatattgaag tacttgttga taaatctctc     1440
ataactattg ggcttggcaa tttgtggatg catgatcttg ttcaagacat gggaaaagaa     1500
gttcttaagc aagatgcgtc atcaaaactt ggtgactaca gtagattatg gaatcatgag     1560
gctattttcg acggaagtga tagcattcaa ggaataatgt ttgatccacc tcaactagaa     1620
atggtagaat ggagtggtac tgccttcaag aagatgaaca atttaagaat tctcattgtc     1680
cgaaatgctg acttttcaac aggccctaaa aatttgccaa ataatttaag ggtgcttgaa     1740
tgggagagat atccttcaga gtctttacca caaggatttt atcctagaaa aattgttgtt     1800
ttaaagttac ggagtagctg tcttatctcc ttaaagccat tgcagaaatt tgaaaagctt     1860
acttgcattg atttctcgtg ctgtcaacta ttaactcaaa tacctgatat gtctagagcc     1920
ccaaatatag taactttgaa gcttaaccga tgcaccagtc taaaagaggt tcatgattct     1980
gttggagttc ttactaagct tcttggttta agccttgagg gatgcaccaa gctcaaaata     2040
tttccatatg gaattcagat gacatctctt atacatctta atctcaatga ttgcagaagt     2100
cttcaacact tcccagatat attgggacag atggatgaac tgaaacgtat tgatgcggaa     2160
aggaccggta ttaagcagat tccacattcc atttgttacc tccggggggct tgaattttta     2220 tgtatatcaa ataattacga tttgatatcc ctcccggaaa gcattaacca attagataga     2280
ttgatacacc ttaatattta taattgcaag aagcttcgac aaatttcagg aattccttca     2340
aatttggaac aaatacgtgc agaagaagca tcttctagtt cctcctttga accaaagttc     2400
tcctatgaca ttttgctgag ttttggaggt gaagatacct gcaacacctt tactgattat     2460
ctctacaatg ctctgtgcca aagggggtttc aacaccttca tagatgatgg cgggttagag     2520 agagggaac aaatttcacc tgctcttctc aatgcaattg aagaatctag ggcttccatt     2580
gttgtgttgt ctgaaaactt cccatttttc acgtggtgcc ttgatgtagt tgtcaagatc     2640
cttgagtgca agaaggaaaa aggccaaatg gtttggccaa ttttctacca agtgaaccg      2700 tcctatgtaa gacttaagaa gaagagctac agagaagcaa tggctaaaca tgaaaatagg     2760
ttcagaaatg atatggacaa agtgagaaaa tggaggtcag cttttgaaaga agcagctgac     2820 ttgtatgaat ataaatttat ctcaaatatt atagaagagg tctctgtcac attacataat     2880
aagcatttat atgttggtga gcatatagtt ggactcaagt cttgcattga agaaatgaag     2940
```

-continued

```
tcaattttag atgttggatc taataatgat gttggcatgg tgggaattca tggaattggt    3000
gggatagaag catcttctag ttcctcctcc aaacccaggt acacctatga cgttttcctg    3060
agttttagag gtgaagatac ccgcaacaca tttaccggta atctctatga tgctctgtgc    3120
caaaggggtt tcaacacctt catagatgat gacgggttgg agagagggca acaaatttca    3180
tatgctctta tcaatgcaat tgaagaatca aaggtttcca ttgttgtgtt ctccgaaaac    3240
tatgcatctt ccccgtggtg ccttgatgaa cttgtcaaga tccttgaatg caagaaggaa    3300
aagggtcaaa tagtttggcc aattttttac aaggttgaac cggccgatgt aagacatctg    3360
aagaacagct acgaagcagc aatggcaaaa catgaaagta ggttcagcaa tgacaaagtg    3420
acaaaatgga ggtcagcttt gaaagaagca gctaacttgt caggatcgga atacaaaact    3480
gggtacgaat acaaatttat caccaacatt atagaagtgg cctccgctaa attacatgat    3540
aagcatttat atattggtga gcacattgtt ggactcaggt ctcgtttaaa agaagtaaag    3600
tcaattttag atattggatc tcacaatact attggcatgg tgggaattca tggaactggt    3660
ggtataggaa aaaccacact tgtcaaggtt ttgtataact tgattgttga tcaatttcac    3720
tgtgcatgtt ttcttgaatc tgccagagaa ggttcaaaat gttccatgga ccttgtaagt    3780
ctacaaaaga aacttctatc ccagatattt aggaaggaaa atttcaactt gggcaatgtt    3840
gatgaaggtg caaatataat aaaacacagg cttcgcaata ggagtgttct tcttgtgctt    3900
gatgatgttg ataaggggga gcaattaaaa aaattggctg ggggatgtga ttggtttggt    3960
cctggtagta ggatcatcat aacaacaagg gataaacatc tgctaattgc tcatggagta    4020
gaaaaaatat atgaaatgaa agagctagat gatgataaag ctcttgaact cttttgttgg    4080
aaggccttca aaacgagtga acctgcagaa agctttgtgg atatatccta taagataata    4140
aaatatgcca agggccttcc attggcttta aatgtaatag gttccaattt gtttggtagg    4200
agtttaaagg catgggaatc tgcattggat aaatataaga ggattctgga caaaggtatt    4260
catgacatac ttagagtaag ctatgatagc ttggaggatg atcagaaaag catttttctc    4320
gatattgctt gtttcttcaa aggggataga ttggaagatg ttgaaaagat actagaagct    4380
tgtgatctct ctccacaata taatattgaa ggaagtgata gcattcaagg aatcatgttt    4440
catccacctc aactagaaat ggtagaatgg agtggtactg ccttcgagaa gatgaacaat    4500
ttaagaattc tcattgtccg aaatgctaac ttttcaacaa gccctaaaaa tttgccaaat    4560
aatttaaggg tgcttgaatg ggaaagatat ccttcagact ctttaccaca aggattttat    4620
cctagaaaaa ttgttgtatt aaagttacga agtagctgtc ttaactcctt aaagccattg    4680
cagaaatttg aaaagcttac ttgcattgat ttctcgtgct gtcaactatt aactcaaata    4740
cctgatatgt ctaatgcccc aaatatagta actttgaagc ttgaccgatg caccagtctg    4800
aaagaggttc atgattctgt tggagttctt actaagcttc ttgatttaag ccttgaggga    4860
tgcaccaagc tcaaaatatt cccacatgga attcagatga catctcttag agatcttaat    4920
ctcaatgatt gcagaagtct tcaacacttc ccagatatat tgggacagat ggatgaacta    4980
agacgtattg atgcgaaaag gaccggtatt aagcagattc acattccat ttgttacctc     5040 acaaggcttg gattttact tatgtcagat aattatgatt tgatatccct cccggaaagc    5100
attagccaat tagatagatt gacagacctt aatatggata attgcaagaa gcttcgacaa    5160
atttcaggaa ttccttcaaa tttgaaacaa atacgtgcag atgttgcata a              5211
```

<210> SEQ ID NO 9

-continued

```
<211> LENGTH: 1023
<212> TYPE: DNA
<213> ORGANISM: Glycine soja

<400> SEQUENCE: 9
atggcggatg aagggggaat tgagaagcgg cgctacgatg ttttttctgtg ttttagagcg      60 caagacacgc gctacacctt cacaggtaat ctctatgctg ctttgcggca ggccagattg     120
aggaccttct tcgctggtgg gttgaagggt ggcgaccaaa tcttagacgc cattcttcaa     180
gcaattcagg aatcaaggat ttcaatcgtt gttctctccc aaagcttcgg gtcttccttg     240
tggtgccttg aagaacttgt gaagatcctt gagtgcaaga aaacaaagaa gcaactcctt     300
attccaatct tttaccgcgt ggatccctcc gacataagaa gacagactgg tagtttttaag     360 gaggagctgc ttaaacatga aagtcgcttc ggaaaggact ccgagaaagt acgcaagtgg     420
aagtcagctt tgactcatgt cgccaccttg cccggatggt gtttcggaga tggaagctgc     480
aggtaccaat atgaatatga attcatcgaa aacattgtgc gagaagtcat cgccattgta     540
ccccgctata gcattttttct gagtttttagt ggaaacgata cccgctcctt tacaggtttt     600
ctcaacaatg cattgtgcag gagtaggtac caaaccttca tgaatgatgg ggaccaaatt     660
tcacaatcta ctaatggagt tattgaagaa tcaaggcttt cgatcattgt atttttctgaa     720 aactatgcac gttcctcgtc ctgtcttgat tttcttttga ccatccttga gtgtatgaag     780
acgaaaaacc aactggtttg ccccatctttt tacaaagtgt taccgtcgga tttaaggcat     840
caaagaaata gctatggtga agccatgact gagcatgaaa atatgtttggg taaggactct     900 gagatggtga agaaatggag gtcagctttg tttgatgtcg ccaacttgaa aggatttttac     960 ttgaaaaccg ggtacgaata tgaatttatt gacaaaatcg tggaaatggc cagtaaaatt    1020
taa                                                                  1023

<210> SEQ ID NO 10
<211> LENGTH: 1071
<212> TYPE: DNA
<213> ORGANISM: Medicago truncatula

<400> SEQUENCE: 10
atggccatga tgaatgaaga ggttgatggc agcagctaca agtacgatgt ttttctaagt      60
tttagagggg aagatactta ttgtaccttc gcaggtaatc tctatcatgc tttacgcaac     120
aagaaaatca agaccttctt cccacatgat caaattcaaa atgatgatga ggaacttcaa     180
ctttcacctt ctattctcaa ggcaattcag gaatcaagga tttcaatcgt cgttctctca     240
aaaaactatg caacctccac acgttgcctc aacgaacttg tgatcatcct tcagtgtatg     300
aagatgaaaa accagcttgt ttggccaatc ttttacgaag tacattcctc ggatgtaaag     360
cttcagagat gtaagtatgg tagtagcagc aaagccatat tgaagttccg agaaaggttt     420
aaagactacc ctcgcaggat gtgggaatgg cagcaagctt tgtctcaagt cacctctatt     480
gctggatgga attatggaat taaattcgaa tatgaactca tccaaaagat tgtggagtta     540
acagtacaat cgctaccccg ctacgatgtt tttctaagtt tttgcgggga agatactcgc     600
tactccttta cgggattcct ctatcatgct ttgcgtctag agggattcaa gatcttcatg     660
gatgatgagg gattggaggg tggaaaccaa atttcacaaa ctctttttaaa agcaattgaa     720 aaatcaaggc tctcaattgt tgtttttgtcc gaaaattatg gatattcgac atggtgtctt     780
gatgaacttg tgaagattat ggagtgcaag aagaccaata ataaattggt ttggccacta     840
ttttacaaaa tagaacagtc agatttaagc tataaaaaaa gtagttatgg taaagccatg     900
```

-continued

```
gcagcacatg aggatagatt tggaaaggaa tctgagaatg tgcaaaaatg gagatcagct      960
ttgtcagaag ttgccttatt gaaagcagac catatcaaag aaaatgagca cgaatatgaa     1020
ttcataaaga agatcgtgga aagggccaat gaagctgaaa tcacacatgtg a             1071

<210> SEQ ID NO 11
<211> LENGTH: 1005
<212> TYPE: DNA
<213> ORGANISM: Phaseolus vulgaris

<400> SEQUENCE: 11
atggcgcgtt atgatgtttt tctgtgcttt agaggggaag acacgcgcct caccttcacg       60
ggtaacctct atgctgcttt gcagcaggca agattgagaa ctttcaggga tgagggagtg      120
ttgaagggtg gcgaccttgt atattccatc attgaagctt tggaagcatc cagggttgcc      180
atcgttgttc tctccgaaaa ctttgcgttt tctaggtggt gccttgacga acttgtcaag      240
atcctagact gcatgaagac aaagaaccaa atcgttattc caatctttta caacgtcgat      300
ccgtccgatg taaggaacct gagaggtagt tttgccgatg ccatggttga ccatgaacat      360
aggttcggaa agaactttga caaaatacga aactggaggt cagctttgac tgaagtggcc      420
aatttgtcag gatggtgttt gggaagagga agcaggttcg gatatgaata tgagtacatt      480
gaaaggattg tgagagactt gaccttgagg ctaccccgct atactatttt tctgagtttt      540
agtggaaaag atacacgctc cttctcgggt tttctctaca atgctctgag cagaagtgga      600
taccatacca tcctcaatga tggggaccag agttcacaat ctactgttgg ggttattgaa      660
aaatcaaaac tttcaatcat tgtctttttct gaaaactatg cacgttctcc ctcctgtctt      720
gatgagcttt tgaggatcct tgagtgcaag gagatgaaaa acaactggt ttgccccatc       780 ttttacaaat tgttaccgtc tgatttaagg catcaaagaa atagttatgg tgaagccatg      840
agtgaacatg aaactatgat gggtaaggac tctgagaagg tgaagaaatg gaggtcagct      900
ttgtttgaag tcgccaactt gaaaggatgg tacatgaaaa cagggtacga atacgaattt      960
attgaaaaaa tcgtggaatt ggccaataaa atttctcggg tgtga                    1005

<210> SEQ ID NO 12
<211> LENGTH: 531
<212> TYPE: DNA
<213> ORGANISM: Pisum sativum

<400> SEQUENCE: 12
atggctaaat ggcaaatttt tcttagtttt agaggagaag atacgcgtta cgcgtttaca       60
ggttctcttt atcaatcttt atgtcaaggg ggattcaaga cctttatgga tgatagagga      120
ttgcagatgg gagaccaaat ttcaccatct cttttaaatg ccattgaagc atcgaggctt      180
tcgattattg ttttatctga aaactatgca aattcgacgt ggtgtctgga tgaacttgtc      240
aagattctcg agtgtatgaa attgaagaat caattggttt ggccaatctt ttataaagtg      300
gagccatctg atatcagaca tatgaaaaaa tcttatggaa aagacatggc tcgacatgaa      360
aatatatttg gaaatgattc tgagagagta caaaaatgga agtcagcttt agttgaagtg      420
tgtaatttgg ccaaaatggc ttattcaatc gggtatgaat atgaatttat tcagaagatt      480
gtggaagatg ccaatctcat tagaagacgt ttgcaaataa gaaacatata g               531

<210> SEQ ID NO 13
<211> LENGTH: 1014
<212> TYPE: DNA
```

-continued

<213> ORGANISM: Glycine max

<400> SEQUENCE: 13

```
atggcggatg aagggggaat tgagaagcgg cgctacgatg tttttctgtg ttttagaggg      60
gaagacacgc gctacacctt cacaggtaat ctctatgctg ctttgcggca ggcgagattg     120
aggaccttct tcgatgatgg gttcaagagt ggcgaccaaa tctttgacgt tgttcttcaa     180
gcaattcagg aatcaaggat ttcaatcgtt gttctctccg aaaacttcgc ttcttcctcg     240
tggtgccttg aagaacttgt gaagatcctt gagtgcaggg aaacaaagaa gcaactcgtt     300
attccaatct tttaccgcat ggatccctcc gacgtaagga gacagactgg ttgttatggg     360
gagagcctgg ctcaacatca atatgagttc agaagcgact ccgagaaagt acgcaattgg     420
caggaagctt tgactcatgt cgccaacttg cccggatgga ggttcagccg gtaccaatat     480
gaatatgaat tcatcgaaga cattgtgcga caagccatcg tcgccattgt accccgctat     540
agcatttttc tgagtttttag tggaaacgat acccgctcct ttacaggttt tctcaacaat     600
gcattgtgca ggagtaggta ccaaaccttc atgaatgatg gggaccaaat ttcacaatct     660
actaatggag ttattgaaga atcaaggctt tcgatcattg tattttctga aaactatgca     720
cgttcctcgt cctgtcttga tttttctttg accatccttg agtgtatgaa gacgaaaaac     780
caactggttt gccccatctt ttacaaagtg ttaccgtcgg atttaaggca tcaaagaaat     840
agctatggta aagccatgac tgagcatgaa aatatgttgg gtaaggactc tgagatggtg     900
aagaaatgga ggtcagcttt gtttgatgtc gccaacttga aaggatttta cttgaaaacc     960
gggtacgaat atgaatttat tgacaaaatc gtggaaatgg ccagtaaaat ttaa          1014
```

<210> SEQ ID NO 14
<211> LENGTH: 1530
<212> TYPE: DNA
<213> ORGANISM: Trifolium pratense

<400> SEQUENCE: 14

```
atgtctggca gctgcaacaa tacggttgat ttcacaaaag aaaagaaccg attggttaca      60
catcgagatt ttgtgcgtga caaaattgaa agaactcata ataaaactca aaaggttagc     120
gatgttgtgt ttgagtggct aaatgaaaca gatatactca tacgtcaatt ggagaatctg     180
tcggcacaag caataacaag aaaacaattt aaaaaattgt tgaaaagagt aatgaaacag     240
aacacgaaag taccttcagg aaattacatt caggaatctt caactccaat tccaagttta     300
gaacacttct cttcaggaaa tttaatgtgt tttaattcta gagagaagat ctccgatcaa     360 ctttttcgtgg cattgaatga tgatagttgt tctatgattg gattgtatgg tagccagggc     420
tcgggtaaaa caacattggt tgaagcaatg gccaaaaaag taaagtattt agagattttt     480
catgagattt tatttgtcaa ggtaacccaa aattcaaata ttagaacaat gcaagatgaa     540
attgttgact cattaaatat gaaatttgat aaaaaaaaca gtgaatctgg aagagccaga     600
gaaatattct caacaataga aagtatgaat tgtccaattc tagtcatttt tgataatgtt     660
ccagcaaaat tcgacccaga agatataggc attccttgta atagtaatcg ctgcaagatt     720
cttttgacca catgttgcca aaaagattgt gacttgttgt ccggtcaaag gaagattcaa     780
cttgatccct tatctagaca ggaagcttgg attttgtttc aaaaacattc aggtatttat     840
gatgatgaga atactcgag atttgactta ttgaatgtag catatgaagt tgcttttagaa     900 tgtgaagggt tacctagaac aattaaagat gtgggacctt tcttaaaaag taaaccaatt     960
gaagaatgga agacaacact agatagtctg aaacattcaa tggccaaatg gcaaattttt    1020
```

-continued

```
cttagtttta gaggagaaga tacacgcaac tcttttacag gttatcttta tcaaacttta    1080
tctcaagcgg gattcaagac cttcatggat gatggaggac tgcatactgg agaccaaatt    1140
tcaccctctc ttgtaaatgc aattgaagca tcgaggcttt cgattattgt tttatctgaa    1200
aactatgcaa attcctcatg gtgtcttgaa gaacttgtca agattcttga gtgtatgaag    1260
ttgaagaatc aattagtttg gccaatcttt tacaaagtgt acccatcaga cataaggcat    1320
ctgagaaaat gttatggcaa agacatggat cgacatgaaa ataattttgg aattaactca    1380
gaaagagtgc agaaatggag gtcagctttg tttgaagtgt ctaatttatc cggaaaagct    1440
tatacaaccg ggtacgaata tgaatttatt caaaagatcg tggaagatgc caatcgtatt    1500
aaaagtcgtt tgcaaatacg aagagcataa                                     1530
```

```
<210> SEQ ID NO 15
<211> LENGTH: 1848
<212> TYPE: DNA
<213> ORGANISM: Vigna angularis

<400> SEQUENCE: 15
```

```
atggaggcag aaagttacaa tagactgagt caacaagacc cttctggtgg tgccactgtt      60
tctcatccat ccagtgaacg aaaaaacttt gatgttttcc tcagtcttgg tggaaaagat     120
gttcgctaca ccttcactgg taatctcttt aatgcttttgc gcagcaagag aattaagacc     180
cttttcagag aacatgaata tgaacctgat gatgacacca atatttcacc ctctgctctt     240
aaagcaatac aaacgtcaaa gatttccatc gttgttttct ccccagaata tgcatcctcc     300
tcaaaacgtc tcgatgaact tgtggccatc cttgagtgta ggatgaggac caaccaactc     360
gtatggccaa tcttttacgg agtggaaccg actgacgtaa gatttcagag aggtagatat     420
gaacaagcca ttaatagatt tgaagaaaga tattattccc cagagaggat gaataaatgg     480
agagcagctt tggctgaagt cagcaacttg agtggatggt tttaccaaaa ggggcacaaa     540
tacgaatata aattcatccg aaagattgtg gaagcagccg tgcaatgcct gtcaagatat     600
gatgtttttc tgagtttttg tggagaggat acccgctaca ctctcacagg ttttctatac     660 aatgccctttc gccgagaggg gattcaaaatc ttcatggacg atgaagaatt ggagggtggg     720
aaccaaattt ctcaaaagct aatgggagca atagaaagtt caagggtttc aattgttgtg     780
ttctctgaaa actatggata ttccacctgg tgtgctttgt ctcaaatcac caacttggaa     840
ggagagcatc tcagtgaaaa tgagtctgta atgttaaatt ttattactgt atttataatt     900
ggtgtttgtt ggaatgtttt agggaaggac acgcgccaca ccctcacagg taacctctat     960
gctgctttgc agcaggctag attcagaact ttcatggatg atgacgagtt gaagggtgcc    1020
gaccaaattg catatacgat cgttttggaa gcatccagga tttcgatcgt tgttctctcc    1080
gaacactttg cgttttccag ttggtgcctt gatgaacttg ctaacatcct agactgcatg    1140
aacacaaaga accaagccgt tttttccaatc ttttacgaag tcgatccgtt ctatgtaagg    1200
cacctgaaag gtagttttgg cgaggccatg gttgcccatg aagctagatt cggaaaggac    1260
tctgagaaag tagaaaaatg gaggtcagct ttggctcaag tggccaactt gtcgggatgg    1320
tgttttggaa gaggaaggtg gtgccaatat gaatatgaat atgaattcat tgaaaggatt    1380
gtgcaacatg tgaccaagtt gttaccccgc tacagcattt ttctgagttt tagtggaaaa    1440
gatacacgct ccttcacggg tttttctctac aatgctttga gccgaagtgg ataccatact    1500
ttcatcagtg atggggaaca tagttcacaa tctattgttg gggttattga aaaatcaagg    1560
```

```
ctttcaatca ttgtctttttc tgaaaactat gcacgttccc cttcctctct tgatgagctt      1620
ttgaggatcc ttgagtgcat ggatatgaaa aaccacctgg tttgccccat cttttacaaa      1680
gtgttaccgt cggatataag gcatcagaga aaaagttatt gtgaagccat gattgaacat      1740
gaaaatgtga tgggtgagga ctctgagaag gtcaagaaat ggaggtcagc tttgtttcaa      1800
gtcgccaact tgaaaggatg gtgcatgaaa acggggtaca gtaaatag                   1848

<210> SEQ ID NO 16
<211> LENGTH: 1065
<212> TYPE: DNA
<213> ORGANISM: Vigna radiata

<400> SEQUENCE: 16
atgtatttca tttcagcatc agagagaagg aatgcagcaa cctgcaatga acatctaagt        60
aatcgcaata acactcagtt tgagttcttg attcatttca ttatcgatgc tatggcgcgt       120
tatgacgttt ttctgtgctt tagagggagg gacacgcgcc acaccttcac aggtaacctc       180
tatgctgctt tgcagcaggc tagattcaga actttcatgg atgatgacga gttgaagggt       240
gccgaccaaa ttgcatatac tatcgttttg gaagcatcca ggatttcgat cgttgttctc       300
tccgaacact ttgcattttc cagttggtgc cttgatgaac tagctaaaat cgtagactgc       360
atgaacacaa agaaccaagc cgttttttcca atctttttacg aagttgatcc gttctatgta      420
aggcacctga aaggtagttt tggcgaggcc atggttgccc atgaagctag gttcggaaag       480
gactctgaga gagtagagaa atggaggtca gctttgattc aagtgaccaa cttgtcagga       540
tggtgttttg caagaggaag gtggtgcgaa tacgaatatg aattcattga aaggattgtg       600
caacatgtga ccaagttggt accccgctac agaatttttg tgagttttag tggaaaagat       660
acacgctcct tcactggttt tctctgcaat gctttgagcc gaagtggata caatactttc       720
atcagtgatg gggaacagag ttcacaatct actgttgggg ttattgaaaa atcaaggctt       780
tcaatcattg tctttttctga aaactatgca cgttcccctt cctgtcttga tgagcttttg      840
agggtccttg agtgcatgga gatgaaaaac cagctggttt gccccatctt ttacaaagtg       900
ttaccatcgg atttaaggca tcagagaaga agttatggtg aagccatgat tgaacatgaa       960
aatgtgatgg gtgaaaactc tgagaaggtc aagaaatgga ggtcagcttt gtttcatgtc      1020
gccaacttga aaggatggtg catgaaaaca gggtacagta aatag                      1065

<210> SEQ ID NO 17
<211> LENGTH: 2664
<212> TYPE: DNA
<213> ORGANISM: Pisum sativum

<400> SEQUENCE: 17
atggcattgg cttgcaatag cctccaaagc agctcttctt caccaaagat gagatggaaa        60
tatgatgtgt ttgtgagctt tagaggagaa gacactcgca acaatttcac cgatcacctc       120
tttggcgctc ttcataagaa agctattatt accttcaggg atgatacaaa gctcaagaaa       180
ggggaagata tatcacttga gcttctacaa gctattgaag atcccaaat  tttgattgtt        240 attttctcaa caaactatgc ttcttccaca tggtgcttgc aagaagtagc aaaaattgct       300
gcatgcattg aagttccagg acaatctgtt ctacctattt tctttgatgt cagtccttct       360
gaggtacgaa agcaatgcgg agattatgaa aaagcctttc aagggcatga agaaagattc       420
aaagcaactt tagagaaagt gcaaagatgg agaggagctc taacacaagt agccaatctc       480
tctggttggg acgttaggga taagccacaa tatgcagaga ttggagaaat tactaaaaag       540
```

-continued

```
gtaacatgct tattgggaaa taaatcttcg actttaccta gggatatagt tgggatgccc        600
tccagagtgg aagaattaga aaaccatctg aatttggact caaatgatga tgatgttcga        660
gtaataggga tttgtggaat gggtggaata ggaaagacga ctcttgctac tgctttgtat        720
gctagaatct ctaatcaatt tgatgcttgc tgctttattg atgatgtaag taaaatttat        780
ggagatcatg gcccaattgg agtacaaaag caacttctgc gtcaaactct aaatgaagaa        840
aatctccaaa tatgcaatct tcctatggct tctaatttga ttcgaactag gctatctcga        900
ttaaaatccc ttgtttttct tgataatgtg gatgaagttg aacaactgga taaattggat        960
atgagactag aatggctagg cagagggagt agaataatca taatttctag aaatgggcac       1020
atcttgacag agtatggagt agatgaagta tacagagttc gactcttgga tcgtaaatgt       1080
gcccttcaat tgttttgcca gaaagctttc aaaagtgatg acatcatgag tggttacata       1140
tacttgacaa aagaagtact agcatatgcc aatggccttc cactcgcaat taaagtgttg       1200
ggctcgtatc tgtatggtcg agatgtgtct gagtggagaa gtgcattgtc aagattaaga       1260
gagaacccaa tgacagatat tatgaatgta ctccgaatta gttttgatgg actagaggat       1320
acagaaaagg acatatttct tgatattgct tgtttctttc atggataccc gaagggatac       1380
ctgaagaaaa ttttagattt tcgtggattt catcctgaaa ttggtttaag agttctcgtt       1440
gataaatcat tcataactta caagaaacag ataatttgca tgcatgattt gtttagagaa       1500
ctgggaaaga gtatcgttag agaaaaatca cccaaagaac caagaaagtg gaacagggtg       1560
tgggactaca aagacgtcca caatgttatc tcagaaaaca tggcaacaga aaaccttgaa       1620
gccatgatga tggagtatga ttcagaacat gatatagaaa tacaacagat gacaacattg       1680
agggccgaag ctttagcaca aatgagtcgc cttaaattgc tcaggttgtt gacgtttaat       1740
ttctcaggaa gtctcaattt tctttcaagt gaattggggt atctacgttg ggataaatat       1800
cctttcacta gtttgccatc aagtttttcag gcgtataaac ttgttgaact gatcctacgt       1860
catagcaaca ttaggaaact atgggaaggc acaaagtctc tacctaattt gacacgtatt       1920
gatctcagtt actcaaagaa tcttaatatg atgccaaatt ttgaggagac tccaaatctt       1980
gagagcctat gtcttgtagg atgtataaaa ctcgtgaaga ttgatccatc cattgctggg       2040
ttatatatat ttgactgccc cagtttagtt gagatggaaa gctattttgg aattgctttt       2100
tcttggatga tacaacttct tcaggttcac atgcaatccg agatcccaag gacagacatt       2160
acaattgtta ttcccaaaac tcaaattcca aagtggttca ccaaacaaca tgtaggcagt       2220
tcaataagca tcgatccatc atccattatg catgacaaga atttgatagg catcgcttgc       2280
tgcttaacat ttgtagcgca agataatcct actaatttaa gggaagaact gtcatcttat       2340
attgcgtttg gttttaaatg tacacagtgt ggggtctatt caattattcc catacttctt       2400
ggaaaagatc tggtcacagt tgatttagat cacctgttgc tagttttttt cagtaggaag       2460
aaatttattg atttgataag tgatgcaaca gatggatggg atgatattag tggtattgaa       2520
ttgagtgcta cagttaggca gcccctttggt ttgcacttgg aagtaaaaaa ttgtggttat       2580
aattggatat ttaaggagga tctggaacaa ttaaatccac aaaagatgta caagggaaat       2640
tcgtcagttc agccatatta ttga                                             2664
```

<210> SEQ ID NO 18
<211> LENGTH: 978
<212> TYPE: DNA
<213> ORGANISM: Phaseolus vulgaris -continued

```
<400> SEQUENCE: 18
atggcgcgtt atgatgtttt tctgtgcttt agagggcgtg acacgcgcca caccttcatg      60
ggtaacctct atgctgcttt gcggcaggcc agattgagaa ctttcatgga tgagggcgtg     120
cttaaaggtg gcgacgttgc agatactatc attcaagctt tggaagcatc cagggtttcc     180
atcgttattc tctccgaaac ctttgcgtct tctaggtggt gccttgacga acttgtcaac     240
atcctagact gcatgaagac aaagaaccaa accgttattc caatctttta caacgtcgat     300
ccctccgatg taaggaacct gaaaggtagt tttggcgctg ccatggttgc ccatgaagat     360
gggttcggaa aggacaatga gagattacaa aagtggagat cagcattgac tcaagtggcc     420
aacttgtcag gatgctgttt gggtacagga agcaggttcg gatatgaata tgagtacatt     480
gaaaggattg tgagaagcgt gaccttggtg atacccccgct ataatatttt tgtgagtttc     540
agtggaaaag atacacgctc cttctcgggt tttctctaca atgctctgag cagaagggga     600
taccatacca tcctcaatga tggggaccag agttcacaat ctactactgt tggggttatt     660
gaaaaatcaa aactttcaat cattgtgttt tctgaaaact atgcacgttc ccctcatgt      720 cttgatgagc ttttgaggat ccttgagtgc aaggagatga aaaccaact ggtttgcccc      780 atcttttaca aagtgttacc gtctgattta aggcatcaaa gaaatagtta tggtgaagcc     840
atgagtgaac atgaaaatat gatgggtaag gactctgaga aggtgaagat atggaggtca     900
gctttgtttg aagtcgccaa cttgaaagga tgtcctagtt ttgttgtgtg gcaattactt     960
tgtgcagata tactttga                                                   978
```

```
<210> SEQ ID NO 19
<211> LENGTH: 984
<212> TYPE: DNA
<213> ORGANISM: Glycine max

<400> SEQUENCE: 19
atggcggatg aagggggaat tgagaagcgg cgctacgatg tttttctgtg ttttagaggg      60
gaagacacgc gcttcacctt cacaggtaat ctctgtgctg ctttgcggca ggccagattg     120
aggaccttct tcgatgatgg gttgaagggt ggcgaccaaa tcttagacgc cagtcttcaa     180
gcaattcagg aatcaaggat ttcaatcgtt gttctctccc acaacttcgc ttcttcctcg     240
tggtgccttg aagaacttgt gaagatcctt gagtgcaggg aaacaaagaa gcaactcgtt     300
attccaatct tttgccgggt ggatccctcc gacgtaagga gacagactgg tcgtttttaag     360 gaggatctgc ttaaacatga aagtcgcttc gaaaaggact ccgagaaagt acgcaagtgg     420
aagtcagctt tgactcaagt cgccaccttg cccggatttt gtttcggaga tggaagctgc     480
agcgaccaat atgaatatga attcatccaa aacattgtgc gagaagccat cgccattgta     540
ccccgctata gcattttttct gagttttagt ggaaacgata cccgctcctt tacaggtttt     600
ctcaacaatg cattgtgcag gagtaggtac caaaccttca tgaatgatgg ggaccaaatt     660
tcacaatcta ctaatggagt tattgaagaa tcaaggcttt cgatcattgt attttctgaa     720
aactatgcac gttcctcgtc ctgtcttgat ttgctttttga ctatccttga gtgtatgaag     780
acgaaaaacc aactggtttg ccccatcttt tacaaagtgt taccgtcgga tttaaggcat     840
caaagaaata gctatggtga agccatgact gaacatgaaa atatgttggg taaggactct     900
gagagggtga agaaatggag gtcagctttg tttgatgtcg ccaacttgaa aggattttac     960
ttgaaaaccg ggtacaacac atag                                            984
```

```
<210> SEQ ID NO 20
<211> LENGTH: 1035
<212> TYPE: DNA
<213> ORGANISM: Glycine max

<400> SEQUENCE: 20
atggcggatg aagggggaat taagaagcgg cgctacgatg tttttctgtg ttttagaggg        60
gaagacacgc gctacacctt caccggtaat ctctatgctg ctttgcggca ggcgagattg       120
aggaccttct tcgatggtgg cattggtggg ttgaaggggt gcgaccaaat ctttgacgtt       180
cttcttcaag caattcagga atcaaggatt tcaatcgttg ttctctccca aaacttcggg       240
tcttccttgt ggtgccttga agaacttgtg aagatccttg agtgcaagaa aacaaagaag       300
caactcgtta ttccaatctt ttaccgcgtg gatcccgccg acgtaaggag acagactggt       360
agttttaagg agcagctgct aaacatgaa agtcgcttcg gaaaggactc cgagaaagta       420
cgccagtgga agtcagcttt gactcaagtc gccaccttgc ccggatggtg tttcggacat       480
ggaagctgca ggtaccaata tgaatatgaa ttcatcgaag acattgtgcg acaagccatc       540
gtcgccattg taccccgcta tagcattttt ctgagtttta gtggaaacga tacccgctcc       600
tttacaggtt ttctcaacaa tgcattgtgc aggagtaggt accaaacctt catgaatgat       660
ggggaccaaa tttcacaatc tactaatgga gttattgaag aatcaaggct ttcgatcatt       720
gtattttctg aaaactatgc acgttcctcg tcctgtcttg attttctttt gaccatcctt       780
gagtgtatga agacgaaaaa ccaactggtt tgccccatct tttacaaagt gttaccgtcg       840
gatttaaggc atcaaagaaa tagctatggt gaagccatga ctgagcatga aaatatgttg       900
ggtaaggact ctgagatggt gaagaaatgg aggtcagctt tgtttgatgt cgccaacttg       960
aaaggatttt acttgaaaac cgggtacgaa tatgaattta ttgacaaaat cgtggaaatg      1020
gccagtaaaa tttaa                                                         1035

<210> SEQ ID NO 21
<211> LENGTH: 374
<212> TYPE: PRT
<213> ORGANISM: Arachis duranensis

<400> SEQUENCE: 21

Met Gly Leu Gln Leu Gln Pro Ser His Ser Ser Ser Ser Ser Trp
1               5                   10                  15

His Trp Glu Tyr Asp Val Phe Leu Asn Phe Arg Gly Pro Asp Thr Arg
                20                  25                  30

Tyr Gly Phe Thr Gly Tyr Leu Tyr Lys Ala Leu Cys Asp Lys Gly Ile
            35                  40                  45

His Ala Phe Met Asp Phe Asp Asp Ile His Arg Gly Asn Glu Ile Ser
        50                  55                  60

Ala Ser Leu Met Lys Ala Ile Glu Ala Ser Arg Ile Ala Ile Leu Val
65                  70                  75                  80

Phe Ser Lys Asn Tyr Ala Glu Ser Ser Tyr Cys Leu Asn Glu Leu Val
                85                  90                  95

Lys Ile Met Glu Cys Ser Gln Arg His Gly Gln Phe Val Leu Pro Val
            100                 105                 110

Phe Tyr Ser Val Asp Pro Ser Val Val Arg His Gln Lys Gly Ile Tyr
            115                 120                 125

Glu Glu Ala Leu Ala Lys Thr Gly Arg Thr Phe Glu His Ala Met Asp
        130                 135                 140

Arg Val Gln Arg Trp Arg Thr Ala Met Ala Asp Ala Ala Asn Leu Ser
```

-continued

```
145               150               155               160

Gly Leu His Phe Lys Gly Asp Gly Tyr Gly Tyr Glu Phe Val Glu Lys
                165               170               175

Ile Val Glu Gln Val Ser Arg Val Ile Lys Arg Val Gly Asp Tyr Pro
                180               185               190

Val Glu Leu Glu Ser Gln Glu Gln Ala Ser Tyr Ser Ser Leu Ala Pro
                195               200               205

Cys Leu Ser Asn Gly Trp Lys Tyr Asp Val Phe Leu Ser Phe Arg Gly
        210               215               220

Thr Asp Thr Arg Phe Gly Phe Thr Gly Asn Leu Tyr Asn Val Leu Cys
225               230               235               240

Gly Lys Gly Ile His Thr Phe Met Asp Asp Glu Ala Leu His Arg Gly
                245               250               255

Asn Glu Ile Ser Gly Thr Leu Asp Lys Ala Ile Glu Gly Ser Lys Ile
                260               265               270

Ala Ile Leu Val Phe Ser Lys Asn Tyr Ala Tyr Ser Ser Tyr Cys Leu
                275               280               285

Asp Glu Leu Val Lys Ile Met Lys Cys Ser Gln Ser Asn Ser Gln Cys
        290               295               300

Val Leu Pro Val Phe Tyr Asn Val Asp Pro Pro His Val Arg His Gln
305               310               315               320

Arg Gly Ser Tyr Glu Glu Ala Leu Ala Lys His Glu Glu Arg Phe Lys
                325               330               335

Asn Asp Val Asp Arg Leu Arg Asp Trp Arg Ala Ala Leu His Gln Ala
                340               345               350

Ala Asn Leu Thr Gly Phe His Phe Lys Gly Gln Pro Thr Gln His Phe
                355               360               365

Lys Ser Gln Ser Arg Asn
        370

<210> SEQ ID NO 22
<211> LENGTH: 484
<212> TYPE: PRT
<213> ORGANISM: Arachis hypogaea

<400> SEQUENCE: 22

Met Gly Leu Gln Pro Ser His Ser Ser Ser Ser Phe Ser Trp His Trp
1               5               10               15

Glu Tyr Asp Val Phe Leu Asn Phe Arg Gly Pro Asp Thr Arg Tyr Gly
                20               25               30

Phe Thr Gly Tyr Leu Tyr Lys Ala Leu Cys Asp Lys Gly Ile Arg Ala
                35               40               45

Phe Met Asp Phe Gly Asp Ile His Arg Gly Asn Glu Ile Ser Ala Ser
        50               55               60

Leu Met Lys Ala Ile Glu Ala Ser Arg Ile Ala Ile Leu Val Phe Ser
65               70               75               80

Lys Asn Tyr Ala Glu Ser Ser Tyr Cys Leu Asn Glu Leu Val Lys Ile
                85               90               95

Met Glu Cys Ser Gln Arg His Gly Gln Phe Val Leu Pro Val Phe Tyr
                100               105               110

Gly Ile Asp Pro Ser Val Val Arg His Gln Lys Gly Ile Tyr Glu Glu
                115               120               125

Ala Leu Ala Lys Thr Gly Arg Thr Phe Glu His Ala Met Asp Arg Val
        130               135               140
```

-continued

```
Gln Arg Trp Arg Thr Ala Met Ala Asp Ala Ala Asn Leu Ser Gly Leu
145                 150                 155                 160

His Phe Lys Gly Asp Gly Tyr Gly Tyr Glu Phe Val Glu Lys Ile Val
                165                 170                 175

Glu Gln Val Ser Arg Val Ile Lys Arg Val Gly Asp Tyr Pro Ile Glu
            180                 185                 190

Leu Glu Ser Gln Glu Gln Ala Ser Tyr Ser Ser Leu Ala Pro Ser Ser
        195                 200                 205

Ser Asn Gly Trp Lys Tyr Asp Val Phe Leu Ser Phe Arg Gly Thr Asp
    210                 215                 220

Thr Arg Phe Gly Phe Thr Gly Asn Leu Tyr Asn Val Leu Cys Gly Lys
225                 230                 235                 240

Gly Ile His Thr Phe Met Asp Asp Glu Ala Leu His Arg Gly Asn Glu
                245                 250                 255

Ile Ser Gly Thr Leu Asp Lys Ala Ile Glu Gly Ser Lys Ile Ala Ile
            260                 265                 270

Leu Val Phe Ser Lys Asn Tyr Ala Tyr Ser Ser Tyr Cys Leu Asp Glu
        275                 280                 285

Leu Val Lys Ile Met Lys Cys Ser Gln Ser His Ser Gln Cys Val Leu
    290                 295                 300

Pro Val Phe Tyr Asn Val Asp Pro Pro His Val Arg His Gln His Gly
305                 310                 315                 320

Ser Tyr Glu Glu Ala Leu Ala Lys His Glu Glu Arg Phe Ser Asp Val
                325                 330                 335

Glu Arg Leu Arg Asp Trp Arg Ala Ala Leu His Gln Ala Ala Asn Leu
            340                 345                 350

Thr Gly Phe His Phe Lys Gly Asn Glu Tyr Glu His Glu Phe Ile Gly
        355                 360                 365

Lys Ile Val Arg Val Val Ser Arg Asn Ile Arg Asn Ile Ala Ser Pro
    370                 375                 380

Val Val Gly Ile Gln Glu Asn Gly Gly Thr Glu Ala Glu Ser Leu Leu
385                 390                 395                 400

Gln Asp Asn Gln Arg Asn Asn Ser Lys Val Lys Ala Glu Thr Glu Ala
            405                 410                 415

Asn Val Glu Asn Phe Met Glu Val Asp Val Phe Glu Lys Ser Val Gly
            420                 425                 430

Val Gln Leu Glu Ser Leu Lys Arg Lys Lys Arg Glu Leu Glu Gly Gln
        435                 440                 445

Ile Arg Ala Ile Asn Asp Gln Ile Thr Glu Phe Gln Arg Lys Thr Val
    450                 455                 460

Ala Lys Arg Lys Lys Ala Phe Asp Ser Gly Lys Lys Cys Gln Val Glu
465                 470                 475                 480

Ser Ile Val Thr

<210> SEQ ID NO 23
<211> LENGTH: 256
<212> TYPE: PRT
<213> ORGANISM: Cajanus cajan

<400> SEQUENCE: 23

Met Lys Thr Lys Gly Gln Leu Val Trp Pro Ile Tyr Tyr Glu Val Glu
1                   5                   10                  15

Pro Ser Glu Val Arg Arg Gln Ser Gly Ile Tyr Gly Glu Ala Met Ser
            20                  25                  30
```

-continued

```
Glu Phe Glu Gln Lys Phe Gly His Glu Ser Glu Met Val Trp Lys Trp
        35              40              45

Arg Ser Ala Leu Thr Glu Val Ser Ser Leu Ser Gly Trp Val Tyr Glu
        50              55              60

Thr Gly Tyr His Ser Tyr Glu Tyr Lys Phe Ile Arg Lys Ile Val Arg
65              70              75              80

Leu Ala Val Glu Ser Leu Pro Arg Tyr Asp Val Phe Leu Ser Phe Ser
                85              90              95

Gly Glu Asp Thr Arg Tyr Ser Phe Thr Gly Phe Leu Tyr Asn Ala Phe
                100             105             110

Arg Arg Glu Gly Phe Asn Ile Phe Met Asp Asp Glu Gly Leu Glu Gly
        115             120             125

Gly Asn Gln Ile Ser Glu Thr Leu Met Arg Ala Ile Glu Met Ser Arg
        130             135             140

Leu Ser Ile Val Val Phe Ser Glu Asn Tyr Ala Tyr Ser Thr Trp Cys
145             150             155             160

Leu Asp Glu Leu Ala Lys Ile Ile Glu Cys Lys Lys Thr Lys Asn Gln
                165             170             175

Met Val Trp Pro Ile Phe His Tyr Val Glu Lys Ser Asp Val Cys Asn
                180             185             190

Gln Thr Lys Ser Tyr Gly Glu Ala Met Ala Ala His Glu Glu Arg Phe
        195             200             205

Gly Lys Asp Ser Glu Lys Val Gln Asn Trp Arg Ser Ala Leu Ser Glu
        210             215             220

Ile Ala Asn Leu Asp Gly His His Phe Arg Glu Asn Glu Tyr Gln Tyr
225             230             235             240

Glu Phe Ile Glu Arg Val Val Asp Leu Ala Ile Ala Ile Gly Asn Gln
                245             250             255
```

```
<210> SEQ ID NO 24
<211> LENGTH: 1736
<212> TYPE: PRT
<213> ORGANISM: Cercis canadensis

<400> SEQUENCE: 24
```

```
Met Ala Asn Phe Gly Glu Ala Ser Ser Ser Ser Ser Ser Lys Pro Arg
1               5               10              15

Tyr Thr Tyr Asp Val Phe Leu Ser Phe Arg Gly Glu Asp Thr Arg Asn
                20              25              30

Thr Phe Thr Gly Asn Leu Tyr Asp Ala Leu Cys Gln Arg Gly Phe Asn
        35              40              45

Thr Phe Ile Asp Asp Asp Gly Leu Glu Arg Gly Gln Gln Ile Ser Tyr
        50              55              60

Ala Leu Ile Asn Ala Ile Glu Glu Ser Lys Val Ser Ile Val Val Phe
65              70              75              80

Ser Glu Asn Tyr Ala Ser Ser Pro Trp Cys Leu Asp Glu Leu Val Lys
                85              90              95

Ile Leu Glu Cys Lys Lys Glu Lys Gly Gln Ile Val Trp Pro Ile Phe
                100             105             110

Tyr Lys Val Glu Pro Ala Asp Val Arg Asp Gln Lys Asn Ser Tyr Glu
        115             120             125

Ala Ala Met Ala Lys His Glu Ser Arg Phe Ser Asn Asp Lys Val Thr
        130             135             140

Lys Trp Arg Ser Ala Leu Lys Glu Ala Ala Asn Leu Ser Gly Ser Glu
145             150             155             160
```

-continued

```
Tyr Lys Thr Gly Tyr Glu Tyr Lys Phe Ile Thr Asn Ile Ile Glu Val
            165             170             175

Ala Ser Thr Lys Leu His Asp Lys His Leu Tyr Ile Gly Glu His Ile
            180             185             190

Val Gly Leu Lys Ser Arg Leu Lys Glu Val Lys Ser Ile Leu Asp Ile
            195             200             205

Gly Ser His Asn Thr Ile Gly Met Val Gly Ile His Gly Thr Gly Gly
    210             215             220

Ile Gly Lys Thr Thr Leu Ala Lys Val Leu Tyr Asn Leu Ile Val Asp
225             230             235             240

Gln Phe His Cys Ala Cys Phe Leu Glu Ser Val Arg Glu Gly Ser Lys
            245             250             255

Cys Ser Met Asp Leu Val Ser Leu Gln Lys Lys Leu Leu Ser Gln Ile
            260             265             270

Phe Arg Lys Glu Asn Phe Asn Leu Gly Asn Val Asp Glu Gly Ala Asn
            275             280             285

Ile Ile Lys His Arg Leu Arg Asn Arg Arg Val Leu Leu Val Leu Asp
    290             295             300

Asp Val Val Lys Gly Glu Gln Leu Lys Lys Leu Ala Gly Gly Cys Asp
305             310             315             320

Trp Phe Gly Pro Gly Ser Arg Ile Ile Ile Thr Thr Arg Asp Lys His
            325             330             335

Leu Leu Ile Ala His Gly Val Glu Lys Ile Tyr Glu Met Asn Glu Leu
            340             345             350

Asp Asp Asp Lys Ala Leu Glu Leu Phe Cys Trp Lys Ala Phe Lys Met
            355             360             365

Ser Glu Pro Thr Glu Gly Phe Val Asp Ile Ser Tyr Lys Ile Ile Lys
            370             375             380

Tyr Ala Lys Gly Leu Pro Leu Ala Leu Asn Val Ile Gly Ser Asn Leu
385             390             395             400

Phe Gly Arg Ser Leu Lys Ala Trp Glu Ser Ala Ser Asp Lys Tyr Lys
            405             410             415

Arg Ile Leu Asp Lys Gly Ile His Asp Ile Leu Arg Val Ser Tyr Asp
            420             425             430

Ser Leu Glu Asp Asp Gln Lys Ser Ile Phe Leu Asp Ile Ala Cys Phe
            435             440             445

Phe Lys Gly Glu Arg Leu Glu Asp Val Glu Lys Ile Leu Asp Ala Cys
    450             455             460

Asp Leu Ser Pro Gln Tyr Asn Ile Glu Val Leu Val Asp Lys Ser Leu
465             470             475             480

Ile Thr Ile Gly Leu Gly Asn Leu Trp Met His Asp Leu Val Gln Asp
            485             490             495

Met Gly Lys Glu Val Leu Lys Gln Asp Ala Ser Ser Lys Leu Gly Asp
            500             505             510

Tyr Ser Arg Leu Trp Asn His Glu Ala Ile Phe Asp Gly Ser Asp Ser
            515             520             525

Ile Gln Gly Ile Met Phe Asp Pro Pro Gln Leu Glu Met Val Glu Trp
    530             535             540

Ser Gly Thr Ala Phe Lys Lys Met Asn Asn Leu Arg Ile Leu Ile Val
545             550             555             560

Arg Asn Ala Asp Phe Ser Thr Gly Pro Lys Asn Leu Pro Asn Asn Leu
            565             570             575
```

-continued

```
Arg Val Leu Glu Trp Glu Arg Tyr Pro Ser Glu Ser Leu Pro Gln Gly
            580                 585                 590

Phe Tyr Pro Arg Lys Ile Val Val Leu Lys Leu Arg Ser Ser Cys Leu
            595                 600                 605

Ile Ser Leu Lys Pro Leu Gln Lys Phe Glu Lys Leu Thr Cys Ile Asp
            610                 615                 620

Phe Ser Cys Cys Gln Leu Leu Thr Gln Ile Pro Asp Met Ser Arg Ala
625                 630                 635                 640

Pro Asn Ile Val Thr Leu Lys Leu Asn Arg Cys Thr Ser Leu Lys Glu
            645                 650                 655

Val His Asp Ser Val Gly Val Leu Thr Lys Leu Leu Gly Leu Ser Leu
            660                 665                 670

Glu Gly Cys Thr Lys Leu Lys Ile Phe Pro Tyr Gly Ile Gln Met Thr
            675                 680                 685

Ser Leu Ile His Leu Asn Leu Asn Asp Cys Arg Ser Leu Gln His Phe
            690                 695                 700

Pro Asp Ile Leu Gly Gln Met Asp Glu Leu Lys Arg Ile Asp Ala Glu
705                 710                 715                 720

Arg Thr Gly Ile Lys Gln Ile Pro His Ser Ile Cys Tyr Leu Arg Gly
            725                 730                 735

Leu Glu Phe Leu Cys Ile Ser Asn Asn Tyr Asp Leu Ile Ser Leu Pro
            740                 745                 750

Glu Ser Ile Asn Gln Leu Asp Arg Leu Ile His Leu Asn Ile Tyr Asn
            755                 760                 765

Cys Lys Lys Leu Arg Gln Ile Ser Gly Ile Pro Ser Asn Leu Glu Gln
            770                 775                 780

Ile Arg Ala Glu Glu Ala Ser Ser Ser Ser Phe Glu Pro Lys Phe
785                 790                 795                 800

Ser Tyr Asp Ile Leu Leu Ser Phe Gly Gly Glu Asp Thr Cys Asn Thr
            805                 810                 815

Phe Thr Asp Tyr Leu Tyr Asn Ala Leu Cys Gln Arg Gly Phe Asn Thr
            820                 825                 830

Phe Ile Asp Asp Gly Gly Leu Glu Arg Gly Glu Gln Ile Ser Pro Ala
            835                 840                 845

Leu Leu Asn Ala Ile Glu Glu Ser Arg Ala Ser Ile Val Val Leu Ser
            850                 855                 860

Glu Asn Phe Pro Phe Phe Thr Trp Cys Leu Asp Val Val Val Lys Ile
865                 870                 875                 880

Leu Glu Cys Lys Lys Glu Lys Gly Gln Met Val Trp Pro Ile Phe Tyr
            885                 890                 895

Gln Val Glu Pro Ser Tyr Val Arg Leu Lys Lys Lys Ser Tyr Arg Glu
            900                 905                 910

Ala Met Ala Lys His Glu Asn Arg Phe Arg Asn Asp Met Asp Lys Val
            915                 920                 925

Arg Lys Trp Arg Ser Ala Leu Lys Glu Ala Ala Asp Leu Tyr Glu Tyr
            930                 935                 940

Lys Phe Ile Ser Asn Ile Ile Glu Glu Val Ser Val Thr Leu His Asn
945                 950                 955                 960

Lys His Leu Tyr Val Gly Glu His Ile Val Gly Leu Lys Ser Cys Ile
            965                 970                 975

Glu Glu Met Lys Ser Ile Leu Asp Val Gly Ser Asn Asn Asp Val Gly
            980                 985                 990

Met Val Gly Ile His Gly Ile Gly  Gly Ile Glu Ala Ser  Ser Ser Ser
```

-continued

```
         995                  1000                 1005

Ser Ser  Lys Pro Arg Tyr Thr  Tyr Asp Val Phe Leu  Ser Phe Arg
    1010                 1015              1020

Gly Glu  Asp Thr Arg Asn Thr  Phe Thr Gly Asn Leu  Tyr Asp Ala
    1025                 1030              1035

Leu Cys  Gln Arg Gly Phe Asn  Thr Phe Ile Asp Asp  Asp Gly Leu
    1040                 1045              1050

Glu Arg  Gly Gln Gln Ile Ser  Tyr Ala Leu Ile Asn  Ala Ile Glu
    1055                 1060              1065

Glu Ser  Lys Val Ser Ile Val  Val Phe Ser Glu Asn  Tyr Ala Ser
    1070                 1075              1080

Ser Pro  Trp Cys Leu Asp Glu  Leu Val Lys Ile Leu  Glu Cys Lys
    1085                 1090              1095

Lys Glu  Lys Gly Gln Ile Val  Trp Pro Ile Phe Tyr  Lys Val Glu
    1100                 1105              1110

Pro Ala  Asp Val Arg His Leu  Lys Asn Ser Tyr Glu  Ala Ala Met
    1115                 1120              1125

Ala Lys  His Glu Ser Arg Phe  Ser Asn Asp Lys Val  Thr Lys Trp
    1130                 1135              1140

Arg Ser  Ala Leu Lys Glu Ala  Ala Asn Leu Ser Gly  Ser Glu Tyr
    1145                 1150              1155

Lys Thr  Gly Tyr Glu Tyr Lys  Phe Ile Thr Asn Ile  Ile Glu Val
    1160                 1165              1170

Ala Ser  Ala Lys Leu His Asp  Lys His Leu Tyr Ile  Gly Glu His
    1175                 1180              1185

Ile Val  Gly Leu Arg Ser Arg  Leu Lys Glu Val Lys  Ser Ile Leu
    1190                 1195              1200

Asp Ile  Gly Ser His Asn Thr  Ile Gly Met Val Gly  Ile His Gly
    1205                 1210              1215

Thr Gly  Gly Ile Gly Lys Thr  Thr Leu Val Lys Val  Leu Tyr Asn
    1220                 1225              1230

Leu Ile  Val Asp Gln Phe His  Cys Ala Cys Phe Leu  Glu Ser Ala
    1235                 1240              1245

Arg Glu  Gly Ser Lys Cys Ser  Met Asp Leu Val Ser  Leu Gln Lys
    1250                 1255              1260

Lys Leu  Leu Ser Gln Ile Phe  Arg Lys Glu Asn Phe  Asn Leu Gly
    1265                 1270              1275

Asn Val  Asp Glu Gly Ala Asn  Ile Ile Lys His Arg  Leu Arg Asn
    1280                 1285              1290

Arg Ser  Val Leu Leu Val Leu  Asp Asp Val Asp Lys  Gly Glu Gln
    1295                 1300              1305

Leu Lys  Lys Leu Ala Gly Gly  Cys Asp Trp Phe Gly  Pro Gly Ser
    1310                 1315              1320

Arg Ile  Ile Ile Thr Thr Arg  Asp Lys His Leu Leu  Ile Ala His
    1325                 1330              1335

Gly Val  Glu Lys Ile Tyr Glu  Met Lys Glu Leu Asp  Asp Asp Lys
    1340                 1345              1350

Ala Leu  Glu Leu Phe Cys Trp  Lys Ala Phe Lys Thr  Ser Glu Pro
    1355                 1360              1365

Ala Glu  Ser Phe Val Asp Ile  Ser Tyr Lys Ile Ile  Lys Tyr Ala
    1370                 1375              1380

Lys Gly  Leu Pro Leu Ala Leu  Asn Val Ile Gly Ser  Asn Leu Phe
    1385                 1390              1395
```

-continued

```
Gly Arg Ser Leu Lys Ala Trp Glu Ser Ala Leu Asp Lys Tyr Lys
    1400            1405            1410

Arg Ile Leu Asp Lys Gly Ile His Asp Ile Leu Arg Val Ser Tyr
    1415            1420            1425

Asp Ser Leu Glu Asp Asp Gln Lys Ser Ile Phe Leu Asp Ile Ala
    1430            1435            1440

Cys Phe Phe Lys Gly Asp Arg Leu Glu Asp Val Glu Lys Ile Leu
    1445            1450            1455

Glu Ala Cys Asp Leu Ser Pro Gln Tyr Asn Ile Glu Gly Ser Asp
    1460            1465            1470

Ser Ile Gln Gly Ile Met Phe His Pro Pro Gln Leu Glu Met Val
    1475            1480            1485

Glu Trp Ser Gly Thr Ala Phe Glu Lys Met Asn Asn Leu Arg Ile
    1490            1495            1500

Leu Ile Val Arg Asn Ala Asn Phe Ser Thr Ser Pro Lys Asn Leu
    1505            1510            1515

Pro Asn Asn Leu Arg Val Leu Glu Trp Glu Arg Tyr Pro Ser Asp
    1520            1525            1530

Ser Leu Pro Gln Gly Phe Tyr Pro Arg Lys Ile Val Val Leu Lys
    1535            1540            1545

Leu Arg Ser Ser Cys Leu Asn Ser Leu Lys Pro Leu Gln Lys Phe
    1550            1555            1560

Glu Lys Leu Thr Cys Ile Asp Phe Ser Cys Cys Gln Leu Leu Thr
    1565            1570            1575

Gln Ile Pro Asp Met Ser Asn Ala Pro Asn Ile Val Thr Leu Lys
    1580            1585            1590

Leu Asp Arg Cys Thr Ser Leu Lys Glu Val His Asp Ser Val Gly
    1595            1600            1605

Val Leu Thr Lys Leu Leu Asp Leu Ser Leu Glu Gly Cys Thr Lys
    1610            1615            1620

Leu Lys Ile Phe Pro His Gly Ile Gln Met Thr Ser Leu Arg Asp
    1625            1630            1635

Leu Asn Leu Asn Asp Cys Arg Ser Leu Gln His Phe Pro Asp Ile
    1640            1645            1650

Leu Gly Gln Met Asp Glu Leu Arg Arg Ile Asp Ala Lys Arg Thr
    1655            1660            1665

Gly Ile Lys Gln Ile Pro His Ser Ile Cys Tyr Leu Thr Arg Leu
    1670            1675            1680

Gly Phe Leu Leu Met Ser Asp Asn Tyr Asp Leu Ile Ser Leu Pro
    1685            1690            1695

Glu Ser Ile Ser Gln Leu Asp Arg Leu Thr Asp Leu Asn Met Asp
    1700            1705            1710

Asn Cys Lys Lys Leu Arg Gln Ile Ser Gly Ile Pro Ser Asn Leu
    1715            1720            1725

Lys Gln Ile Arg Ala Asp Val Ala
    1730            1735
```

```
<210> SEQ ID NO 25
<211> LENGTH: 340
<212> TYPE: PRT
<213> ORGANISM: Glycine soja

<400> SEQUENCE: 25

Met Ala Asp Glu Gly Gly Ile Glu Lys Arg Arg Tyr Asp Val Phe Leu
```

-continued

```
1               5                 10                15

Cys Phe Arg Ala Gln Asp Thr Arg Tyr Thr Phe Thr Gly Asn Leu Tyr
            20                25                30

Ala Ala Leu Arg Gln Ala Arg Leu Arg Thr Phe Phe Ala Gly Gly Leu
            35                40                45

Lys Gly Gly Asp Gln Ile Leu Asp Ala Ile Leu Gln Ala Ile Gln Glu
            50                55                60

Ser Arg Ile Ser Ile Val Val Leu Ser Gln Ser Phe Gly Ser Ser Leu
65                    70                75                80

Trp Cys Leu Glu Glu Leu Val Lys Ile Leu Glu Cys Lys Lys Thr Lys
                85                90                95

Lys Gln Leu Leu Ile Pro Ile Phe Tyr Arg Val Asp Pro Ser Asp Ile
            100               105               110

Arg Arg Gln Thr Gly Ser Phe Lys Glu Glu Leu Leu Lys His Glu Ser
            115               120               125

Arg Phe Gly Lys Asp Ser Glu Lys Val Arg Lys Trp Lys Ser Ala Leu
            130               135               140

Thr His Val Ala Thr Leu Pro Gly Trp Cys Phe Gly Asp Gly Ser Cys
145                   150               155               160

Arg Tyr Gln Tyr Glu Tyr Glu Phe Ile Glu Asn Ile Val Arg Glu Val
                165               170               175

Ile Ala Ile Val Pro Arg Tyr Ser Ile Phe Leu Ser Phe Ser Gly Asn
                180               185               190

Asp Thr Arg Ser Phe Thr Gly Phe Leu Asn Asn Ala Leu Cys Arg Ser
                195               200               205

Arg Tyr Gln Thr Phe Met Asn Asp Gly Asp Gln Ile Ser Gln Ser Thr
            210               215               220

Asn Gly Val Ile Glu Glu Ser Arg Leu Ser Ile Ile Val Phe Ser Glu
225                   230               235               240

Asn Tyr Ala Arg Ser Ser Ser Cys Leu Asp Phe Leu Leu Thr Ile Leu
                245               250               255

Glu Cys Met Lys Thr Lys Asn Gln Leu Val Cys Pro Ile Phe Tyr Lys
                260               265               270

Val Leu Pro Ser Asp Leu Arg His Gln Arg Asn Ser Tyr Gly Glu Ala
            275               280               285

Met Thr Glu His Glu Asn Met Leu Gly Lys Asp Ser Glu Met Val Lys
            290               295               300

Lys Trp Arg Ser Ala Leu Phe Asp Val Ala Asn Leu Lys Gly Phe Tyr
305                   310               315               320

Leu Lys Thr Gly Tyr Glu Tyr Glu Phe Ile Asp Lys Ile Val Glu Met
                325               330               335

Ala Ser Lys Ile
                340

<210> SEQ ID NO 26
<211> LENGTH: 356
<212> TYPE: PRT
<213> ORGANISM: Medicago truncatula

<400> SEQUENCE: 26

Met Ala Met Met Asn Glu Glu Val Asp Gly Ser Ser Tyr Lys Tyr Asp
1               5                 10                15

Val Phe Leu Ser Phe Arg Gly Glu Asp Thr Tyr Cys Thr Phe Ala Gly
            20                25                30
```

```
Asn Leu Tyr His Ala Leu Arg Asn Lys Lys Ile Lys Thr Phe Phe Pro
         35                  40                  45

His Asp Gln Ile Gln Asn Asp Asp Glu Glu Leu Gln Leu Ser Pro Ser
     50                  55                  60

Ile Leu Lys Ala Ile Gln Glu Ser Arg Ile Ser Ile Val Val Leu Ser
 65                  70                  75                  80

Lys Asn Tyr Ala Thr Ser Thr Arg Cys Leu Asn Glu Leu Val Ile Ile
                 85                  90                  95

Leu Gln Cys Met Lys Met Lys Asn Gln Leu Val Trp Pro Ile Phe Tyr
             100                 105                 110

Glu Val His Ser Ser Asp Val Lys Leu Gln Arg Cys Lys Tyr Gly Ser
             115                 120                 125

Ser Ser Lys Ala Ile Leu Lys Phe Arg Glu Arg Phe Lys Asp Tyr Pro
         130                 135                 140

Arg Arg Met Trp Glu Trp Gln Gln Ala Leu Ser Gln Val Thr Ser Ile
145                 150                 155                 160

Ala Gly Trp Asn Tyr Gly Ile Lys Phe Glu Tyr Glu Leu Ile Gln Lys
                 165                 170                 175

Ile Val Glu Leu Thr Val Gln Ser Leu Pro Arg Tyr Asp Val Phe Leu
             180                 185                 190

Ser Phe Cys Gly Glu Asp Thr Arg Tyr Ser Phe Thr Gly Phe Leu Tyr
             195                 200                 205

His Ala Leu Arg Leu Glu Gly Phe Lys Ile Phe Met Asp Asp Glu Gly
         210                 215                 220

Leu Glu Gly Gly Asn Gln Ile Ser Gln Thr Leu Leu Lys Ala Ile Glu
225                 230                 235                 240

Lys Ser Arg Leu Ser Ile Val Val Leu Ser Glu Asn Tyr Gly Tyr Ser
                 245                 250                 255

Thr Trp Cys Leu Asp Glu Leu Val Lys Ile Met Glu Cys Lys Lys Thr
             260                 265                 270

Asn Asn Lys Leu Val Trp Pro Leu Phe Tyr Lys Ile Glu Gln Ser Asp
         275                 280                 285

Leu Ser Tyr Lys Lys Ser Ser Tyr Gly Lys Ala Met Ala Ala His Glu
         290                 295                 300

Asp Arg Phe Gly Lys Glu Ser Glu Asn Val Gln Lys Trp Arg Ser Ala
305                 310                 315                 320

Leu Ser Glu Val Ala Leu Leu Lys Ala Asp His Ile Lys Glu Asn Glu
                 325                 330                 335

His Glu Tyr Glu Phe Ile Lys Lys Ile Val Glu Arg Ala Asn Glu Ala
             340                 345                 350

Glu Asn His Met
         355
```

```
<210> SEQ ID NO 27
<211> LENGTH: 334
<212> TYPE: PRT
<213> ORGANISM: Phaseolus vulgaris

<400> SEQUENCE: 27

Met Ala Arg Tyr Asp Val Phe Leu Cys Phe Arg Gly Glu Asp Thr Arg
1                5                  10                  15

Leu Thr Phe Thr Gly Asn Leu Tyr Ala Ala Leu Gln Gln Ala Arg Leu
                 20                  25                  30

Arg Thr Phe Arg Asp Glu Gly Val Leu Lys Gly Gly Asp Leu Val Tyr
         35                  40                  45
```

-continued

```
Ser Ile Ile Glu Ala Leu Glu Ala Ser Arg Val Ala Ile Val Val Leu
    50              55              60

Ser Glu Asn Phe Ala Phe Ser Arg Trp Cys Leu Asp Glu Leu Val Lys
65              70              75              80

Ile Leu Asp Cys Met Lys Thr Lys Asn Gln Ile Val Ile Pro Ile Phe
            85              90              95

Tyr Asn Val Asp Pro Ser Asp Val Arg Asn Leu Arg Gly Ser Phe Ala
            100             105             110

Asp Ala Met Val Asp His Glu His Arg Phe Gly Lys Asn Phe Asp Lys
            115             120             125

Ile Arg Asn Trp Arg Ser Ala Leu Thr Glu Val Ala Asn Leu Ser Gly
        130             135             140

Trp Cys Leu Gly Arg Gly Ser Arg Phe Gly Tyr Glu Tyr Glu Tyr Ile
145             150             155             160

Glu Arg Ile Val Arg Asp Leu Thr Leu Arg Leu Pro Arg Tyr Thr Ile
            165             170             175

Phe Leu Ser Phe Ser Gly Lys Asp Thr Arg Ser Phe Ser Gly Phe Leu
            180             185             190

Tyr Asn Ala Leu Ser Arg Ser Gly Tyr His Thr Ile Leu Asn Asp Gly
            195             200             205

Asp Gln Ser Ser Gln Ser Thr Val Gly Val Ile Glu Lys Ser Lys Leu
    210             215             220

Ser Ile Ile Val Phe Ser Glu Asn Tyr Ala Arg Ser Pro Ser Cys Leu
225             230             235             240

Asp Glu Leu Leu Arg Ile Leu Glu Cys Lys Glu Met Lys Lys Gln Leu
            245             250             255

Val Cys Pro Ile Phe Tyr Lys Leu Leu Pro Ser Asp Leu Arg His Gln
            260             265             270

Arg Asn Ser Tyr Gly Glu Ala Met Ser Glu His Glu Thr Met Met Gly
            275             280             285

Lys Asp Ser Glu Lys Val Lys Lys Trp Arg Ser Ala Leu Phe Glu Val
    290             295             300

Ala Asn Leu Lys Gly Trp Tyr Met Lys Thr Gly Tyr Glu Tyr Glu Phe
305             310             315             320

Ile Glu Lys Ile Val Glu Leu Ala Asn Lys Ile Ser Arg Val
            325             330
```

<210> SEQ ID NO 28
<211> LENGTH: 176
<212> TYPE: PRT
<213> ORGANISM: Pisum sativum

<400> SEQUENCE: 28

```
Met Ala Lys Trp Gln Ile Phe Leu Ser Phe Arg Gly Glu Asp Thr Arg
1               5               10              15

Tyr Ala Phe Thr Gly Ser Leu Tyr Gln Ser Leu Cys Gln Gly Gly Phe
            20              25              30

Lys Thr Phe Met Asp Asp Arg Gly Leu Gln Met Gly Asp Gln Ile Ser
        35              40              45

Pro Ser Leu Leu Asn Ala Ile Glu Ala Ser Arg Leu Ser Ile Ile Val
    50              55              60

Leu Ser Glu Asn Tyr Ala Asn Ser Thr Trp Cys Leu Asp Glu Leu Val
65              70              75              80

Lys Ile Leu Glu Cys Met Lys Leu Lys Asn Gln Leu Val Trp Pro Ile
```

```
                    85                 90                 95

Phe Tyr Lys Val Glu Pro Ser Asp Ile Arg His Met Lys Lys Ser Tyr
            100                 105                 110

Gly Lys Asp Met Ala Arg His Glu Asn Ile Phe Gly Asn Asp Ser Glu
            115                 120                 125

Arg Val Gln Lys Trp Lys Ser Ala Leu Val Glu Val Cys Asn Leu Ala
            130                 135                 140

Lys Met Ala Tyr Ser Ile Gly Tyr Glu Tyr Glu Phe Ile Gln Lys Ile
145                 150                 155                 160

Val Glu Asp Ala Asn Leu Ile Arg Arg Arg Leu Gln Ile Arg Asn Ile
                    165                 170                 175

<210> SEQ ID NO 29
<211> LENGTH: 337
<212> TYPE: PRT
<213> ORGANISM: Glycine max

<400> SEQUENCE: 29

Met Ala Asp Glu Gly Gly Ile Glu Lys Arg Arg Tyr Asp Val Phe Leu
1                   5                   10                  15

Cys Phe Arg Gly Glu Asp Thr Arg Tyr Thr Phe Thr Gly Asn Leu Tyr
                    20                  25                  30

Ala Ala Leu Arg Gln Ala Arg Leu Arg Thr Phe Phe Asp Asp Gly Phe
            35                  40                  45

Lys Ser Gly Asp Gln Ile Phe Asp Val Val Leu Gln Ala Ile Gln Glu
            50                  55                  60

Ser Arg Ile Ser Ile Val Val Leu Ser Glu Asn Phe Ala Ser Ser Ser
65                  70                  75                  80

Trp Cys Leu Glu Glu Leu Val Lys Ile Leu Glu Cys Arg Glu Thr Lys
                    85                  90                  95

Lys Gln Leu Val Ile Pro Ile Phe Tyr Arg Met Asp Pro Ser Asp Val
            100                 105                 110

Arg Arg Gln Thr Gly Cys Tyr Gly Glu Ser Leu Ala Gln His Gln Tyr
            115                 120                 125

Glu Phe Arg Ser Asp Ser Glu Lys Val Arg Asn Trp Gln Glu Ala Leu
            130                 135                 140

Thr His Val Ala Asn Leu Pro Gly Trp Arg Phe Ser Arg Tyr Gln Tyr
145                 150                 155                 160

Glu Tyr Glu Phe Ile Glu Asp Ile Val Arg Gln Ala Ile Val Ala Ile
            165                 170                 175

Val Pro Arg Tyr Ser Ile Phe Leu Ser Phe Ser Gly Asn Asp Thr Arg
            180                 185                 190

Ser Phe Thr Gly Phe Leu Asn Asn Ala Leu Cys Arg Ser Arg Tyr Gln
            195                 200                 205

Thr Phe Met Asn Asp Gly Asp Gln Ile Ser Gln Ser Thr Asn Gly Val
            210                 215                 220

Ile Glu Glu Ser Arg Leu Ser Ile Ile Val Phe Ser Glu Asn Tyr Ala
225                 230                 235                 240

Arg Ser Ser Ser Cys Leu Asp Phe Leu Leu Thr Ile Leu Glu Cys Met
            245                 250                 255

Lys Thr Lys Asn Gln Leu Val Cys Pro Ile Phe Tyr Lys Val Leu Pro
            260                 265                 270

Ser Asp Leu Arg His Gln Arg Asn Ser Tyr Gly Glu Ala Met Thr Glu
            275                 280                 285
```

-continued

```
His Glu Asn Met Leu Gly Lys Asp Ser Glu Met Val Lys Lys Trp Arg
    290                 295                 300

Ser Ala Leu Phe Asp Val Ala Asn Leu Lys Gly Phe Tyr Leu Lys Thr
305                 310                 315                 320

Gly Tyr Glu Tyr Glu Phe Ile Asp Lys Ile Val Glu Met Ala Ser Lys
                325                 330                 335

Ile

<210> SEQ ID NO 30
<211> LENGTH: 509
<212> TYPE: PRT
<213> ORGANISM: Trifolium pratense

<400> SEQUENCE: 30

Met Ser Gly Ser Cys Asn Asn Thr Val Asp Phe Thr Lys Glu Lys Asn
1               5                   10                  15

Arg Leu Val Thr His Arg Asp Phe Val Arg Asp Lys Ile Glu Arg Thr
                20                  25                  30

His Asn Lys Thr Gln Lys Val Ser Asp Val Val Phe Glu Trp Leu Asn
            35                  40                  45

Glu Thr Asp Ile Leu Ile Arg Gln Leu Glu Asn Leu Ser Ala Gln Ala
    50                  55                  60

Ile Thr Arg Lys Gln Phe Lys Lys Leu Leu Lys Arg Val Met Glu Gln
65                  70                  75                  80

Asn Thr Lys Val Pro Ser Gly Asn Tyr Ile Gln Glu Ser Ser Thr Pro
                85                  90                  95

Ile Pro Ser Leu Glu His Phe Ser Ser Gly Asn Leu Met Cys Phe Asn
            100                 105                 110

Ser Arg Glu Lys Ile Ser Asp Gln Leu Phe Val Ala Leu Asn Asp Asp
        115                 120                 125

Ser Cys Ser Met Ile Gly Leu Tyr Gly Ser Gln Gly Ser Gly Lys Thr
    130                 135                 140

Thr Leu Val Glu Ala Met Ala Lys Lys Val Lys Tyr Leu Glu Ile Phe
145                 150                 155                 160

His Glu Ile Leu Phe Val Lys Val Thr Gln Asn Ser Asn Ile Arg Thr
                165                 170                 175

Met Gln Asp Glu Ile Val Asp Ser Leu Asn Met Lys Phe Asp Lys Lys
            180                 185                 190

Asn Ser Glu Ser Gly Arg Ala Arg Glu Ile Phe Ser Thr Ile Glu Ser
        195                 200                 205

Met Asn Cys Pro Ile Leu Val Ile Phe Asp Asn Val Pro Ala Lys Phe
    210                 215                 220

Asp Pro Glu Asp Ile Gly Ile Pro Cys Asn Ser Asn Arg Cys Lys Ile
225                 230                 235                 240

Leu Leu Thr Thr Cys Cys Gln Lys Asp Cys Asp Leu Leu Ser Gly Gln
                245                 250                 255

Arg Lys Ile Gln Leu Asp Pro Leu Ser Arg Gln Glu Ala Trp Ile Leu
            260                 265                 270

Phe Gln Lys His Ser Gly Ile Tyr Asp Asp Glu Lys Tyr Ser Arg Phe
        275                 280                 285

Asp Leu Leu Asn Val Ala Tyr Glu Val Ala Leu Glu Cys Glu Gly Leu
    290                 295                 300

Pro Arg Thr Ile Lys Asp Val Gly Pro Phe Leu Lys Ser Lys Pro Ile
305                 310                 315                 320
```

-continued

```
Glu Glu Trp Lys Thr Thr Leu Asp Ser Leu Lys His Ser Met Ala Lys
            325                 330                 335

Trp Gln Ile Phe Leu Ser Phe Arg Gly Glu Asp Thr Arg Asn Ser Phe
            340                 345                 350

Thr Gly Tyr Leu Tyr Gln Thr Leu Ser Gln Ala Gly Phe Lys Thr Phe
            355                 360                 365

Met Asp Asp Gly Gly Leu His Thr Gly Asp Gln Ile Ser Pro Ser Leu
    370                 375                 380

Val Asn Ala Ile Glu Ala Ser Arg Leu Ser Ile Ile Val Leu Ser Glu
385                 390                 395                 400

Asn Tyr Ala Asn Ser Ser Trp Cys Leu Glu Glu Leu Val Lys Ile Leu
            405                 410                 415

Glu Cys Met Lys Leu Lys Asn Gln Leu Val Trp Pro Ile Phe Tyr Lys
            420                 425                 430

Val Tyr Pro Ser Asp Ile Arg His Leu Arg Lys Cys Tyr Gly Lys Asp
            435                 440                 445

Met Asp Arg His Glu Asn Asn Phe Gly Ile Asn Ser Glu Arg Val Gln
    450                 455                 460

Lys Trp Arg Ser Ala Leu Phe Glu Val Ser Asn Leu Ser Gly Lys Ala
465                 470                 475                 480

Tyr Thr Thr Gly Tyr Glu Tyr Glu Phe Ile Gln Lys Ile Val Glu Asp
            485                 490                 495

Ala Asn Arg Ile Lys Ser Arg Leu Gln Ile Arg Arg Ala
            500                 505

<210> SEQ ID NO 31
<211> LENGTH: 615
<212> TYPE: PRT
<213> ORGANISM: Vigna angularis

<400> SEQUENCE: 31

Met Glu Ala Glu Ser Tyr Asn Arg Leu Ser Gln Gln Asp Pro Ser Gly
1               5                   10                  15

Gly Ala Thr Val Ser His Pro Ser Ser Glu Arg Lys Asn Phe Asp Val
            20                  25                  30

Phe Leu Ser Leu Gly Gly Lys Asp Val Arg Tyr Thr Phe Thr Gly Asn
            35                  40                  45

Leu Phe Asn Ala Leu Arg Ser Lys Arg Ile Lys Thr Leu Phe Arg Glu
    50                  55                  60

His Glu Tyr Glu Pro Asp Asp Asp Thr Asn Ile Ser Pro Ser Ala Leu
65                  70                  75                  80

Lys Ala Ile Gln Thr Ser Lys Ile Ser Ile Val Val Phe Ser Pro Glu
            85                  90                  95

Tyr Ala Ser Ser Ser Lys Arg Leu Asp Glu Leu Val Ala Ile Leu Glu
            100                 105                 110

Cys Arg Met Arg Thr Asn Gln Leu Val Trp Pro Ile Phe Tyr Gly Val
            115                 120                 125

Glu Pro Thr Asp Val Arg Phe Gln Arg Gly Arg Tyr Glu Gln Ala Ile
    130                 135                 140

Asn Arg Phe Glu Glu Arg Tyr Tyr Ser Pro Glu Arg Met Asn Lys Trp
145                 150                 155                 160

Arg Ala Ala Leu Ala Glu Val Ser Asn Leu Ser Gly Trp Phe Tyr Gln
            165                 170                 175

Lys Gly His Lys Tyr Glu Tyr Lys Phe Ile Arg Lys Ile Val Glu Ala
            180                 185                 190
```

```
Ala Val Gln Cys Leu Ser Arg Tyr Asp Val Phe Leu Ser Phe Cys Gly
        195                 200                 205

Glu Asp Thr Arg Tyr Thr Leu Thr Gly Phe Leu Tyr Asn Ala Leu Arg
    210                 215                 220

Arg Glu Gly Phe Lys Ile Phe Met Asp Asp Glu Glu Leu Glu Gly Gly
225                 230                 235                 240

Asn Gln Ile Ser Gln Lys Leu Met Gly Ala Ile Glu Ser Ser Arg Val
                245                 250                 255

Ser Ile Val Val Phe Ser Glu Asn Tyr Gly Tyr Ser Thr Trp Cys Ala
                260                 265                 270

Leu Ser Gln Ile Thr Asn Leu Glu Gly Glu His Leu Ser Glu Asn Glu
        275                 280                 285

Ser Val Met Leu Asn Phe Ile Thr Val Phe Ile Ile Gly Val Cys Trp
    290                 295                 300

Asn Val Leu Gly Lys Asp Thr Arg His Thr Leu Thr Gly Asn Leu Tyr
305                 310                 315                 320

Ala Ala Leu Gln Gln Ala Arg Phe Arg Thr Phe Met Asp Asp Asp Glu
                325                 330                 335

Leu Lys Gly Ala Asp Gln Ile Ala Tyr Thr Ile Val Leu Glu Ala Ser
        340                 345                 350

Arg Ile Ser Ile Val Val Leu Ser Glu His Phe Ala Phe Ser Ser Trp
        355                 360                 365

Cys Leu Asp Glu Leu Ala Asn Ile Leu Asp Cys Met Asn Thr Lys Asn
    370                 375                 380

Gln Ala Val Phe Pro Ile Phe Tyr Glu Val Asp Pro Phe Tyr Val Arg
385                 390                 395                 400

His Leu Lys Gly Ser Phe Gly Glu Ala Met Val Ala His Glu Ala Arg
                405                 410                 415

Phe Gly Lys Asp Ser Glu Lys Val Glu Lys Trp Arg Ser Ala Leu Ala
                420                 425                 430

Gln Val Ala Asn Leu Ser Gly Trp Cys Phe Gly Arg Gly Arg Trp Cys
        435                 440                 445

Gln Tyr Glu Tyr Glu Tyr Glu Phe Ile Glu Arg Ile Val Gln His Val
        450                 455                 460

Thr Lys Leu Leu Pro Arg Tyr Ser Ile Phe Leu Ser Phe Ser Gly Lys
465                 470                 475                 480

Asp Thr Arg Ser Phe Thr Gly Phe Leu Tyr Asn Ala Leu Ser Arg Ser
                485                 490                 495

Gly Tyr His Thr Phe Ile Ser Asp Gly Glu His Ser Ser Gln Ser Ile
            500                 505                 510

Val Gly Val Ile Glu Lys Ser Arg Leu Ser Ile Ile Val Phe Ser Glu
            515                 520                 525

Asn Tyr Ala Arg Ser Pro Ser Ser Leu Asp Glu Leu Leu Arg Ile Leu
        530                 535                 540

Glu Cys Met Asp Met Lys Asn His Leu Val Cys Pro Ile Phe Tyr Lys
545                 550                 555                 560

Val Leu Pro Ser Asp Ile Arg His Gln Arg Lys Ser Tyr Cys Glu Ala
                565                 570                 575

Met Ile Glu His Glu Asn Val Met Gly Glu Asp Ser Glu Lys Val Lys
            580                 585                 590

Lys Trp Arg Ser Ala Leu Phe Gln Val Ala Asn Leu Lys Gly Trp Cys
        595                 600                 605
```

```
Met Lys Thr Gly Tyr Ser Lys
    610                 615

<210> SEQ ID NO 32
<211> LENGTH: 354
<212> TYPE: PRT
<213> ORGANISM: Vigna radiata

<400> SEQUENCE: 32

Met Tyr Phe Ile Ser Ala Ser Glu Arg Arg Asn Ala Ala Thr Cys Asn
1               5                   10                  15

Glu His Leu Ser Asn Arg Asn Asn Thr Gln Phe Glu Phe Leu Ile His
            20                  25                  30

Phe Ile Ile Asp Ala Met Ala Arg Tyr Asp Val Phe Leu Cys Phe Arg
        35                  40                  45

Gly Arg Asp Thr Arg His Thr Phe Thr Gly Asn Leu Tyr Ala Ala Leu
    50                  55                  60

Gln Gln Ala Arg Phe Arg Thr Phe Met Asp Asp Asp Glu Leu Lys Gly
65                  70                  75                  80

Ala Asp Gln Ile Ala Tyr Thr Ile Val Leu Glu Ala Ser Arg Ile Ser
                85                  90                  95

Ile Val Val Leu Ser Glu His Phe Ala Phe Ser Ser Trp Cys Leu Asp
            100                 105                 110

Glu Leu Ala Lys Ile Val Asp Cys Met Asn Thr Lys Asn Gln Ala Val
            115                 120                 125

Phe Pro Ile Phe Tyr Glu Val Asp Pro Phe Tyr Val Arg His Leu Lys
        130                 135                 140

Gly Ser Phe Gly Glu Ala Met Val Ala His Glu Ala Arg Phe Gly Lys
145                 150                 155                 160

Asp Ser Glu Arg Val Glu Lys Trp Arg Ser Ala Leu Ile Gln Val Thr
                165                 170                 175

Asn Leu Ser Gly Trp Cys Phe Ala Arg Gly Arg Trp Cys Glu Tyr Glu
            180                 185                 190

Tyr Glu Phe Ile Glu Arg Ile Val Gln His Val Thr Lys Leu Val Pro
            195                 200                 205

Arg Tyr Arg Ile Phe Val Ser Phe Ser Gly Lys Asp Thr Arg Ser Phe
        210                 215                 220

Thr Gly Phe Leu Cys Asn Ala Leu Ser Arg Ser Gly Tyr Asn Thr Phe
225                 230                 235                 240

Ile Ser Asp Gly Glu Gln Ser Ser Gln Ser Thr Val Gly Val Ile Glu
                245                 250                 255

Lys Ser Arg Leu Ser Ile Ile Val Phe Ser Glu Asn Tyr Ala Arg Ser
            260                 265                 270

Pro Ser Cys Leu Asp Glu Leu Leu Arg Val Leu Glu Cys Met Glu Met
            275                 280                 285

Lys Asn Gln Leu Val Cys Pro Ile Phe Tyr Lys Val Leu Pro Ser Asp
    290                 295                 300

Leu Arg His Gln Arg Arg Ser Tyr Gly Glu Ala Met Ile Glu His Glu
305                 310                 315                 320

Asn Val Met Gly Glu Asn Ser Glu Lys Val Lys Lys Trp Arg Ser Ala
                325                 330                 335

Leu Phe His Val Ala Asn Leu Lys Gly Trp Cys Met Lys Thr Gly Tyr
            340                 345                 350

Ser Lys
```

```
<210> SEQ ID NO 33
<211> LENGTH: 887
<212> TYPE: PRT
<213> ORGANISM: Pisum sativum

<400> SEQUENCE: 33

Met Ala Leu Ala Cys Asn Ser Leu Gln Ser Ser Ser Ser Pro Lys
1               5                   10                  15

Met Arg Trp Lys Tyr Asp Val Phe Val Ser Phe Arg Gly Glu Asp Thr
            20                  25                  30

Arg Asn Asn Phe Thr Asp His Leu Phe Gly Ala Leu His Lys Lys Ala
        35                  40                  45

Ile Ile Thr Phe Arg Asp Asp Thr Lys Leu Lys Lys Gly Glu Asp Ile
    50                  55                  60

Ser Leu Glu Leu Leu Gln Ala Ile Glu Gly Ser Gln Ile Leu Ile Val
65                  70                  75                  80

Ile Phe Ser Thr Asn Tyr Ala Ser Ser Thr Trp Cys Leu Gln Glu Val
                85                  90                  95

Ala Lys Ile Ala Ala Cys Ile Glu Val Pro Gly Gln Ser Val Leu Pro
            100                 105                 110

Ile Phe Phe Asp Val Ser Pro Ser Glu Val Arg Lys Gln Cys Gly Asp
            115                 120                 125

Tyr Glu Lys Ala Phe Gln Gly His Glu Glu Arg Phe Lys Ala Thr Leu
    130                 135                 140

Glu Lys Val Gln Arg Trp Arg Gly Ala Leu Thr Gln Val Ala Asn Leu
145                 150                 155                 160

Ser Gly Trp Asp Val Arg Asp Lys Pro Gln Tyr Ala Glu Ile Gly Glu
                165                 170                 175

Ile Thr Lys Lys Val Thr Cys Leu Leu Gly Asn Lys Ser Ser Thr Leu
            180                 185                 190

Pro Arg Asp Ile Val Gly Met Pro Ser Arg Val Glu Glu Leu Glu Asn
            195                 200                 205

His Leu Asn Leu Asp Ser Asn Asp Asp Val Arg Val Ile Gly Ile
    210                 215                 220

Cys Gly Met Gly Gly Ile Gly Lys Thr Thr Leu Ala Thr Ala Leu Tyr
225                 230                 235                 240

Ala Arg Ile Ser Asn Gln Phe Asp Ala Cys Cys Phe Ile Asp Asp Val
                245                 250                 255

Ser Lys Ile Tyr Gly Asp His Gly Pro Ile Gly Val Gln Lys Gln Leu
            260                 265                 270

Leu Arg Gln Thr Leu Asn Glu Glu Asn Leu Gln Ile Cys Asn Leu Pro
            275                 280                 285

Met Ala Ser Asn Leu Ile Arg Thr Arg Leu Ser Arg Leu Lys Ser Leu
    290                 295                 300

Val Phe Leu Asp Asn Val Asp Glu Val Glu Gln Leu Asp Lys Leu Asp
305                 310                 315                 320

Met Arg Leu Glu Trp Leu Gly Arg Gly Ser Arg Ile Ile Ile Ser
                325                 330                 335

Arg Asn Gly His Ile Leu Thr Glu Tyr Gly Val Asp Glu Val Tyr Arg
            340                 345                 350

Val Arg Leu Leu Asp Arg Lys Cys Ala Leu Gln Leu Phe Cys Gln Lys
            355                 360                 365

Ala Phe Lys Ser Asp Asp Ile Met Ser Gly Tyr Ile Tyr Leu Thr Lys
    370                 375                 380
```

```
Glu Val Leu Ala Tyr Ala Asn Gly Leu Pro Leu Ala Ile Lys Val Leu
385                 390                 395                 400

Gly Ser Tyr Leu Tyr Gly Arg Asp Val Ser Glu Trp Arg Ser Ala Leu
                405                 410                 415

Ser Arg Leu Arg Glu Asn Pro Met Thr Asp Ile Met Asn Val Leu Arg
            420                 425                 430

Ile Ser Phe Asp Gly Leu Glu Asp Thr Glu Lys Asp Ile Phe Leu Asp
            435                 440                 445

Ile Ala Cys Phe Phe His Gly Tyr Pro Lys Gly Tyr Leu Lys Lys Ile
        450                 455                 460

Leu Asp Phe Arg Gly Phe His Pro Glu Ile Gly Leu Arg Val Leu Val
465                 470                 475                 480

Asp Lys Ser Phe Ile Thr Tyr Lys Lys Gln Ile Ile Cys Met His Asp
                485                 490                 495

Leu Phe Arg Glu Leu Gly Lys Ser Ile Val Arg Glu Lys Ser Pro Lys
            500                 505                 510

Glu Pro Arg Lys Trp Asn Arg Val Trp Asp Tyr Lys Asp Val His Asn
            515                 520                 525

Val Ile Ser Glu Asn Met Ala Thr Glu Asn Leu Glu Ala Met Met Met
        530                 535                 540

Glu Tyr Asp Ser Glu His Asp Ile Glu Ile Gln Gln Met Thr Thr Leu
545                 550                 555                 560

Arg Ala Glu Ala Leu Ala Gln Met Ser Arg Leu Lys Leu Leu Arg Leu
                565                 570                 575

Leu Thr Phe Asn Phe Ser Gly Ser Leu Asn Phe Leu Ser Ser Glu Leu
                580                 585                 590

Gly Tyr Leu Arg Trp Asp Lys Tyr Pro Phe Thr Ser Leu Pro Ser Ser
            595                 600                 605

Phe Gln Ala Tyr Lys Leu Val Glu Leu Ile Leu Arg His Ser Asn Ile
        610                 615                 620

Arg Lys Leu Trp Glu Gly Thr Lys Ser Leu Pro Asn Leu Thr Arg Ile
625                 630                 635                 640

Asp Leu Ser Tyr Ser Lys Asn Leu Asn Met Met Pro Asn Phe Glu Glu
                645                 650                 655

Thr Pro Asn Leu Glu Ser Leu Cys Leu Val Gly Cys Ile Lys Leu Val
                660                 665                 670

Lys Ile Asp Pro Ser Ile Ala Gly Leu Tyr Ile Phe Asp Cys Pro Ser
            675                 680                 685

Leu Val Glu Met Glu Ser Tyr Phe Gly Ile Ala Phe Ser Trp Met Ile
        690                 695                 700

Gln Leu Leu Gln Val His Met Gln Ser Glu Ile Pro Arg Thr Asp Ile
705                 710                 715                 720

Thr Ile Val Ile Pro Lys Thr Gln Ile Pro Lys Trp Phe Thr Lys Gln
                725                 730                 735

His Val Gly Ser Ser Ile Ser Ile Asp Pro Ser Ser Ile Met His Asp
            740                 745                 750

Lys Asn Leu Ile Gly Ile Ala Cys Cys Leu Thr Phe Val Ala Gln Asp
            755                 760                 765

Asn Pro Thr Asn Leu Arg Glu Glu Leu Ser Ser Tyr Ile Ala Phe Gly
        770                 775                 780

Phe Lys Cys Thr Gln Cys Gly Val Tyr Ser Ile Ile Pro Ile Leu Leu
785                 790                 795                 800
```

```
Gly Lys Asp Leu Val Thr Val Asp Leu Asp His Leu Leu Leu Val Phe
                805                 810                 815

Phe Ser Arg Lys Lys Phe Ile Asp Leu Ile Ser Asp Ala Thr Asp Gly
            820                 825                 830

Trp Asp Asp Ile Ser Gly Ile Glu Leu Ser Ala Thr Val Arg Gln Pro
        835                 840                 845

Phe Gly Leu His Leu Glu Val Lys Asn Cys Gly Tyr Asn Trp Ile Phe
    850                 855                 860

Lys Glu Asp Leu Glu Gln Leu Asn Pro Gln Lys Met Tyr Lys Gly Asn
865                 870                 875                 880

Ser Ser Val Gln Pro Tyr Tyr
                885

<210> SEQ ID NO 34
<211> LENGTH: 202
<212> TYPE: PRT
<213> ORGANISM: Phaseolus vulgaris

<400> SEQUENCE: 34

Lys Asp Asn Glu Arg Leu Gln Lys Trp Arg Ser Ala Leu Thr Gln Val
1               5                   10                  15

Ala Asn Leu Ser Gly Cys Cys Leu Gly Thr Gly Ser Arg Phe Gly Tyr
            20                  25                  30

Glu Tyr Glu Tyr Ile Glu Arg Ile Val Arg Ser Val Thr Leu Val Ile
        35                  40                  45

Pro Arg Tyr Asn Ile Phe Val Ser Phe Ser Gly Lys Asp Thr Arg Ser
    50                  55                  60

Phe Ser Gly Phe Leu Tyr Asn Ala Leu Ser Arg Arg Gly Tyr His Thr
65                  70                  75                  80

Ile Leu Asn Asp Gly Asp Gln Ser Ser Gln Ser Thr Thr Val Gly Val
                85                  90                  95

Ile Glu Lys Ser Lys Leu Ser Ile Ile Val Phe Ser Glu Asn Tyr Ala
            100                 105                 110

Arg Ser Pro Ser Cys Leu Asp Glu Leu Leu Arg Ile Leu Glu Cys Lys
        115                 120                 125

Glu Met Lys Asn Gln Leu Val Cys Pro Ile Phe Tyr Lys Val Leu Pro
    130                 135                 140

Ser Asp Leu Arg His Gln Arg Asn Ser Tyr Gly Glu Ala Met Ser Glu
145                 150                 155                 160

His Glu Asn Met Met Gly Lys Asp Ser Glu Lys Val Lys Ile Trp Arg
                165                 170                 175

Ser Ala Leu Phe Glu Val Ala Asn Leu Lys Gly Cys Pro Ser Phe Val
            180                 185                 190

Val Trp Gln Leu Leu Cys Ala Asp Ile Leu
        195                 200

<210> SEQ ID NO 35
<211> LENGTH: 327
<212> TYPE: PRT
<213> ORGANISM: Glycine max

<400> SEQUENCE: 35

Met Ala Asp Glu Gly Gly Ile Glu Lys Arg Arg Tyr Asp Val Phe Leu
1               5                   10                  15

Cys Phe Arg Gly Glu Asp Thr Arg Phe Thr Phe Thr Gly Asn Leu Cys
            20                  25                  30
```

-continued

```
Ala Ala Leu Arg Gln Ala Arg Leu Arg Thr Phe Phe Asp Asp Gly Leu
        35                  40                  45

Lys Gly Gly Asp Gln Ile Leu Asp Ala Ser Leu Gln Ala Ile Gln Glu
        50                  55                  60

Ser Arg Ile Ser Ile Val Val Leu Ser His Asn Phe Ala Ser Ser Ser
65                  70                  75                  80

Trp Cys Leu Glu Glu Leu Val Lys Ile Leu Glu Cys Arg Glu Thr Lys
                85                  90                  95

Lys Gln Leu Val Ile Pro Ile Phe Cys Arg Val Asp Pro Ser Asp Val
            100                 105                 110

Arg Arg Gln Thr Gly Arg Phe Lys Glu Asp Leu Leu Lys His Glu Ser
        115                 120                 125

Arg Phe Glu Lys Asp Ser Glu Lys Val Arg Lys Trp Lys Ser Ala Leu
    130                 135                 140

Thr Gln Val Ala Thr Leu Pro Gly Phe Cys Phe Gly Asp Gly Ser Cys
145                 150                 155                 160

Ser Asp Gln Tyr Glu Tyr Glu Phe Ile Gln Asn Ile Val Arg Glu Ala
                165                 170                 175

Ile Ala Ile Val Pro Arg Tyr Ser Ile Phe Leu Ser Phe Ser Gly Asn
            180                 185                 190

Asp Thr Arg Ser Phe Thr Gly Phe Leu Asn Asn Ala Leu Cys Arg Ser
        195                 200                 205

Arg Tyr Gln Thr Phe Met Asn Asp Gly Asp Gln Ile Ser Gln Ser Thr
    210                 215                 220

Asn Gly Val Ile Glu Glu Ser Arg Leu Ser Ile Ile Val Phe Ser Glu
225                 230                 235                 240

Asn Tyr Ala Arg Ser Ser Ser Cys Leu Asp Leu Leu Leu Thr Ile Leu
                245                 250                 255

Glu Cys Met Lys Thr Lys Asn Gln Leu Val Cys Pro Ile Phe Tyr Lys
                260                 265                 270

Val Leu Pro Ser Asp Leu Arg His Gln Arg Asn Ser Tyr Gly Glu Ala
            275                 280                 285

Met Thr Glu His Glu Asn Met Leu Gly Lys Asp Ser Glu Arg Val Lys
        290                 295                 300

Lys Trp Arg Ser Ala Leu Phe Asp Val Ala Asn Leu Lys Gly Phe Tyr
305                 310                 315                 320

Leu Lys Thr Gly Tyr Asn Thr
                325

<210> SEQ ID NO 36
<211> LENGTH: 344
<212> TYPE: PRT
<213> ORGANISM: Glycine max

<400> SEQUENCE: 36

Met Ala Asp Glu Gly Gly Ile Lys Lys Arg Arg Tyr Asp Val Phe Leu
1               5                   10                  15

Cys Phe Arg Gly Glu Asp Thr Arg Tyr Thr Phe Thr Gly Asn Leu Tyr
            20                  25                  30

Ala Ala Leu Arg Gln Ala Arg Leu Arg Thr Phe Phe Asp Gly Gly Ile
        35                  40                  45

Gly Gly Leu Lys Gly Gly Asp Gln Ile Phe Asp Val Leu Leu Gln Ala
        50                  55                  60

Ile Gln Glu Ser Arg Ile Ser Ile Val Val Leu Ser Gln Asn Phe Gly
65                  70                  75                  80
```

-continued

```
Ser Ser Leu Trp Cys Leu Glu Glu Leu Val Lys Ile Leu Glu Cys Lys
            85                  90                  95

Lys Thr Lys Lys Gln Leu Val Ile Pro Ile Phe Tyr Arg Val Asp Pro
            100                 105                 110

Ala Asp Val Arg Arg Gln Thr Gly Ser Phe Lys Glu Gln Leu Leu Lys
            115                 120                 125

His Glu Ser Arg Phe Gly Lys Asp Ser Glu Lys Val Arg Gln Trp Lys
        130                 135                 140

Ser Ala Leu Thr Gln Val Ala Thr Leu Pro Gly Trp Cys Phe Gly His
145                 150                 155                 160

Gly Ser Cys Arg Tyr Gln Tyr Glu Tyr Glu Phe Ile Glu Asp Ile Val
                165                 170                 175

Arg Gln Ala Ile Val Ala Ile Val Pro Arg Tyr Ser Ile Phe Leu Ser
            180                 185                 190

Phe Ser Gly Asn Asp Thr Arg Ser Phe Thr Gly Phe Leu Asn Asn Ala
            195                 200                 205

Leu Cys Arg Ser Arg Tyr Gln Thr Phe Met Asn Asp Gly Asp Gln Ile
        210                 215                 220

Ser Gln Ser Thr Asn Gly Val Ile Glu Glu Ser Arg Leu Ser Ile Ile
225                 230                 235                 240

Val Phe Ser Glu Asn Tyr Ala Arg Ser Ser Ser Cys Leu Asp Phe Leu
                245                 250                 255

Leu Thr Ile Leu Glu Cys Met Lys Thr Lys Asn Gln Leu Val Cys Pro
            260                 265                 270

Ile Phe Tyr Lys Val Leu Pro Ser Asp Leu Arg His Gln Arg Asn Ser
            275                 280                 285

Tyr Gly Glu Ala Met Thr Glu His Glu Asn Met Leu Gly Lys Asp Ser
        290                 295                 300

Glu Met Val Lys Lys Trp Arg Ser Ala Leu Phe Asp Val Ala Asn Leu
305                 310                 315                 320

Lys Gly Phe Tyr Leu Lys Thr Gly Tyr Glu Tyr Glu Phe Ile Asp Lys
                325                 330                 335

Ile Val Glu Met Ala Ser Lys Ile
            340
```

```
<210> SEQ ID NO 37
<211> LENGTH: 1104
<212> TYPE: DNA
<213> ORGANISM: Glycine soja

<400> SEQUENCE: 37
atgtcgaatg aactagaaaa ctacgatgtt tttctcagtt ttcatggcca agattcccgt      60
tacaccttca ctggtactct ctataatgct ttgcgcagca agagaatcaa gacctttttc     120
acagaacatg aatatgatcg taaactacac actgatgaca gccaaattcc accctctact     180
cttaaagcaa ttaaggaatc aaggatttcg gtggttgttt tgtcggaaaa ctatgcatcc     240
tcctcaagat gtcttgatga acttgtggcc atccttgagt gtaacaggac gataaaccaa     300
ctggtgtggc ccatctttta cgaagtgtat ccgtggcacg taaggcagca gagaggtagc     360
tatgaagcac ccatgtctaa atttgaagaa atatttggag attccaatga gagggtgaag     420
caatggagag cagctttatt tgaagtcacc aacttgaatg gatggtgtta caaaactggg     480
acgtcccagt acgaatatga attgatcgaa aagatcgtgg aatcaaccgt gcaagccttg     540
cccggatatg atgttttttct gagttttacc ggagaggata cccgctacac tttcacaggt     600
```

-continued

```
tttctctata atgcctttcg ccgagaggga ttcaaaatct tcatggatga tgaggaattg        660
gagagtggga accaaatttc acagaagctt atgggagcaa ttgagagttc aaagatttca        720
attgttgtgc tctctgaaaa ctatgcatat tccacctggt gtcttgatga acttgccaag        780
atcattgagt gtatgaagac caacaatcaa atggtttggc caatatttta caatgtgcaa        840
aagtcggatg tatgcaatca aacaaaaagt tatggtgaag ccatgactga acatgaaaaa        900
agatttggaa aggactctga gaaagtgcag aaatggaggc tgctttgtc tgaaatcaac        960 aacttggaag agaccatgt caaacaaat gagtaccaac atgaattaat cgaaaggatt       1020
gtggaaaagg tcattaaaat tgaaggtagc aagcatacag caaatccttt cctttatcc       1080 catgacagct acgaggaaga atga                                             1104
```

<210> SEQ ID NO 38
<211> LENGTH: 1092
<212> TYPE: DNA
<213> ORGANISM: Phaseolus vulgaris

<400> SEQUENCE: 38

```
atgtccaatg aaccaaaaaa ctatgatgtt tttctgagtc ttggtggtga agatgttcgc         60
tacaccttca ctggtagtct cttcagtgct ttgtgcagca agagaatcaa gacgtttttc        120
agagaacatg aagaagatcc tgagccatac actaatgaca ccaatatttc accctcttct        180
cttaaagcaa tacaagagtc aaagatttcc atcgttgttt tctcccaagg atatgcatcc        240
tcctcaagat gtctcgatga acttgtggcc atccttgact gttggatgaa gagcgaccaa        300
cttgtctggc caatctatta cggagtggat ccgagtgagg taagaactca gaaaggtgga        360
tttggacaag ccatgttcag agttagaaa aggtattcca cagagaggat gaacaaatgg        420
agagaagctt tggttgaggt tagcagattc agtggatggg tttaccaaat ggggtccaag        480
tacgaataca aattcatccg aaagattgtg gaagcagccc tgcaatccct gccaagatat        540 gatgttttc tgagtttttg tggagaggat acgcgccata ctctcactgg ttttctcttt        600
gatgccattc gccgagaggg attcaaaatc ttcatggacg atgaagaatt ggagggtggg        660
aaccaaattt ctgaaacgct catgggagca attcaaagtt caaggatttc cattgttgtg        720
ttctctgaaa actatggata ttccacttgg tgtcttgatg aacttgccaa gatcactgag        780
tgtatgaaca ccaagaatca gaaggtttgg ccaatatttt acaatgtgga gaagttggat        840
gtgtgcaatc agacaaaaag ttatggtgaa gccatgactg cacatgaaaa aagatttgga        900
aaggactctg agaaggtgct gaaatggagg tctgctttgt ctcaaatcac caacttggat        960
ggagagcatc tcagtgaaaa tgagttccaa catgaatcta tcgaaaggat tgtggaacgg       1020
ctcattaata ttgaagatgg gaagcatata gcaagtcctt tccttattca agacaacaat       1080
ggagaagaat ga                                                           1092
```

<210> SEQ ID NO 39
<211> LENGTH: 819
<212> TYPE: DNA
<213> ORGANISM: Pisum sativum

<400> SEQUENCE: 39

```
atgcagatcc ttgtgaccgc acgttgccaa caagaatgtg atttgatgta ctgtcaaagg         60
gatgttcaac ttgatccctt atctaaagag gaggcttgga ctttgtttga aaaacattcg        120
ggcattcatg acgaggactg ctcctcctcg cccgacttat cgaatgtcgc acgtgaagtt        180
```

```
gcttttgaat gtgaagggggt gcctagatta attaaagatg tggcgtcttc cttaagaaat      240
aaaccaattg atgaatggaa agcatcacta gatagtctca aacattcaat ggctaaatgg      300 caaattttc ttagttttcg aggagaagat acgcgttacg cgtttacagg ttctctttat       360
caatctttac gtcaagggggg attcaagacc tttatggatg atggaggatt ggagacgggga     420 gaccaaattt caccatctct tctaaatgcc attgaagcgt cgaggctttc gattattgtt      480
ttatctgaaa actatgcaaa ttcgacgtgg tgtctggatg agcttgtcaa gattctcgag      540
tgtaagaaat tgaagaatca attggtttgg ccaatctttt ataaagtgga tccatctgat      600
atcagacata tgagaaaatg ttatggaaaa gacatggctc gacatgaaaa tagatttgga      660
attgattctg agagagtaca aaaatggaag tcagctttag atgaagtgtg taatttgtcc      720
ggaaaggctt attcaatcgg gtatgaatat gaatttattc agaagattgt ggaacatgcc      780
aatctcatta gaagtcgttt gcaaataaga aacatatag                             819
```

<210> SEQ ID NO 40
<211> LENGTH: 1068
<212> TYPE: DNA
<213> ORGANISM: Glycine max

<400> SEQUENCE: 40

```
atgtcgaatg aactaaaaaa ctatgatgtt tttctcaatt ttcatggcaa agattccggt      60
tacaccttca ctggtactct ctataatgct ttgcgcagca agagaatcaa gacctttttc      120
acaaaacatg aatatggtcg taaactacac actgatgaca gccacattcc acccttact       180 cttaaagcaa ttaaggaatc aaggatttcg gtggttgttt tgtcggaaaa ctatgcatcc      240
tcctcaagat gtcttgatga acttgtggcc atccttgagt gtaaaaggac gataaaccaa       300
ctggtgtggc ccatctttta caaagtggat ccgtcgcaag taaggcacca gaaaggtagc       360
tatggagaac acatttgtaa ttttaaaaaa attttttagag attacaacga ttccaatgag      420
agggtgaagc aatggagagc agctttatct gaagtcagca aattgagtgg atggctttac       480
aatgatcgga ggtcccagta cgaatatgaa ttcatcgaaa ggatcgtgga atcaaccgtg      540
caagccttgc ccggatatga tgtttttctg agttttaccg agaggatac ccgctacact        600 ttcacaggtt ttctctataa tgcctttcgc cgagaggggat tcaaaatctt catggatgat      660
gaggaattgg agagtgggaa ccaaatttca cagaagctta tgagagcaat tgagagttca       720
aagatttcaa ttgttgtgct ctctgaaaac tatgcatatt ccacctggtg tcttgatgaa      780
cttgccaaga tcattgagtg tatgaagacc aacaatcaaa tggtttggcc aatattttac      840
aatgtgcaaa agtcggatgt atgcaatcaa acaaaaagtt atggtgaagc catgactgaa       900
catgaaaaaa gatttggaaa ggactctgag aaggtgcaga aatggaggtc tgctttgtct      960
gaaatcaaaa acttggaagg agaccatgtc aaacaaaatg agtacgtaat gctttaatt      1020 aattacttaa tatatgcttc cctcttaagt gtttttgacc atctttga                 1068
```

<210> SEQ ID NO 41
<211> LENGTH: 1113
<212> TYPE: DNA
<213> ORGANISM: Glycine max

<400> SEQUENCE: 41

```
atgtcgaatg aactaaaaaa ctatgatgtt tttctcaatt ttcatggcaa agattccggt      60
tacaccttca ctggtactct ctataatgct ttgcgcagca agagaatcaa gacctttttc      120
acaaaacatg aatatggtcg taaactacac actgatgaca gccacattcc acccttact       180
```

-continued

```
cttaaagcaa ttaaggaatc aaggatttcg gtggttgttt tgtcggaaaa ctatgcatcc        240
tcctcaagat gtcttgatga acttgtggcc atccttgagt gtaaaaggac gataaaccaa        300
ctggtgtggc ccatctttta caaagtggat ccgtcgcaag taaggcacca gaaaggtagc        360
tatggagaac acatttgtaa tttttaaaaaa atttttagag attacaacga ttccaatgag       420
agggtgaagc aatggagagc agctttatct gaagtcagca aattgagtgg atggctttac        480
aatgatcgga ggtcccagta cgaatatgaa ttcatcgaaa ggatcgtgga atcaaccgtg        540
caagccttgc ccggatatga tgttttttctg agttttaccg gagaggatac ccgctacact       600
ttcacaggtt ttctctataa tgcctttcgc cgagagggat tcaaaatctt catggatgat        660
gaggaattgg agagtgggaa ccaaatttca cagaagctta tgagagcaat tgagagttca        720
aagatttcaa ttgttgtgct ctctgaaaac tatgcatatt ccacctggtg tcttgatgaa        780
cttgccaaga tcattgagtg tatgaagacc aacaatcaaa tggtttggcc aatattttac        840
aatgtgcaaa agtcggatgt atgcaatcaa acaaaaagtt atggtgaagc catgactgaa        900
catgaaaaaa gatttggaaa ggactctgag aaggtgcaga aatggaggtc tgctttgtct        960
gaaatcaaaa acttggaagg agaccatgtc aaacaaaatg agtaccaaca tgaattaatc       1020
gaaaggattg tggaaaaggt cattaaaatt gaaggtagca agcatacagc aaatcctttc       1080
cttttatcca atgacagcta cgaggaagaa tga                                   1113
```

<210> SEQ ID NO 42
<211> LENGTH: 1098
<212> TYPE: DNA
<213> ORGANISM: Vigna radiata

<400> SEQUENCE: 42

```
atgtcttgtg aaccaaaaag ctatgatgtt tttctcagtc ttggtggaaa agatgttcgt         60
tacaccttca ctggtaatct ctttaatgct ttgcgcagca agagaattaa gacccttttc        120
agagaacatg aatatgaacc tgagctacac actcatcaaa ctaatatttc accctctgtt        180
cttaaagcac tacaaacgtc aaagatttcc atcgttgttt tctccccaga atatgcatcc        240
tcctcaagac gtctcgatga acttgtggcc atccttgagt gtaggatgag gaccaaccaa        300
ctcgtatggc caatctttta cggagtggaa cccactgacg taagatttca gagaggtaga        360
tatgaacaag ccatgaatac atttgaagaa agatattccc cagagaggat gaataaatgg        420
agatcagctt tggctgaagt cagcaacttg agtggatggt tttaccaaaa ggagcacaaa        480
tacgaatata aattcatcag aaagattgtg gaagcagccg tgcaatccct gtcaagatat        540 gatgttttttt tgagtttttg tggagaggat acccgctaca ctctcacagg ttttctatac       600 aatgcccctta gccgagaggg attcaaaatc ttcatggacg atgaagaatt ggagggtggg       660
aaccaaattt ctcaaaagct aatgggagca atagaaagtt caagggtttc aattgttgtg        720
ttctctgaaa actatggata ttccacctgg tgtcttgatg aactggccaa gatcactgag        780
tgtatgaaga ccaagaatca gatggtttgg ccaatatttt acaatgtgga aaagtcggat        840
gtatgcaatc aaacaaaaag ttatggtgag gccatgactg cacatgaaaa aaggtttggg        900
aaggactccg agaaggtgca aaaatggagg tctgctttgt ctcaaatcac caacttggaa        960
ggagagcatc tcagtgaaaa tgagttccaa catgaatcta tcgaaaagat tgtggaacgg       1020
ctcattaata ttgaagatgg gaagcatata gcaagtcctt ccttgttcc aatgacagct        1080 acggagaaca atgaatga                                                   1098
```

-continued

```
<210> SEQ ID NO 43
<211> LENGTH: 513
<212> TYPE: DNA
<213> ORGANISM: Pisum sativum

<400> SEQUENCE: 43
atgtctcttc caaagtatga cgtcttcatc agctttagag gagacgacac tcgtgacaac      60
ttcacgagtc atctttatgc agaattgcgt aggaaaaata ttgaaacatt catagattat     120
agacttggca gagggaaga gattttccca actctgtgca aagcaataga agaatcagct       180
atttatgtgg ttattttgtc agaacactat gcttcttcca cttggtgttt ggaagaactc     240
acaaagatac tcgaatgtaa ggagagacat ggaaggaaag tgattcctgt cttctacaag     300
gtggatccgt caactgttag acatcagaca cagagttatg cagatgattt tgttaaacat     360
caacaacgat ttggcgacaa agtggatgca tggaaggctg ctctaaccca aatagctaat     420
ctttctggca tggattcaca caaaatcagg gatgacctaa acggagctgg aatgcctgtt     480
ttccacccta attctagttg tattaagttg tga                                 513

<210> SEQ ID NO 44
<211> LENGTH: 1098
<212> TYPE: DNA
<213> ORGANISM: Phaseolus vulgaris

<400> SEQUENCE: 44
atgtccaatg aaccaaaaaa ctatgatgtt tttctgagtc ttggtggtga agatgttcgc      60
tacaccttca ctggtaatct cttttatgct ttgtgcagca agagaatcaa gacgtttttc     120
agagaacatg aacatgatcc tgagctatac actaatgaca ccaatatttc accctctgct     180
cttaaagcaa tacaagagtc aaagatttcc atggttgttt tctcccaaca atatgcatcc     240
tcctcaagat gtctcgatga acttgtggcc atccttgact gtaggatgaa gagcgaccaa     300
cttgtctggc caatctatta tggagtggat ccgagtgacc tagtaactca cgaaggtaga     360
ttcggacagg ccatgtgcag agttgaagaa aaatattcca cagagaggat aaacaaatgg     420
agagaagctt tggttcaagt tggccaatta agtggatggg tttatcaaag gaggttcaag     480
tacgaatata aattcatccg aaagatcgtg aaagcagctg tgcaatccct gccaagatat     540
gatgtttttc tgagcttttg tggagaggat acccgctaca ctcttgcagg ttttctctat     600
aatgccatta gccgagaggg attcaaaatc ttcatggacg atgaagaatt ggagggtggg     660
aaccaaattt ctgaaacgct catgggagca attgaaagtt caaggatttc aattgttgtg     720
ttctctgaaa actatggata ttccacttgg tgtcttgatg aacttgccaa gatcactgag     780
tgtatgaaca ccaagaatca gaaggtttgg ccaatatttt acaatgtgga gaagatggat     840
gtgtgcaatc aaacaaaaag ttatggtgag gccatgactg cacatggaaa aatgtttgga     900
aaggagtctg agaaggtgca gaaatggaag tctgctttgt ctcagatcac caacttggat     960
ggagagcatc tcattgaaaa tgagttccaa catgaatcta tcgaaaggat tgtggaacag    1020
ctcattaata ttgaagatgg gaagcatata gcaagtcctt tccttgttcc aacgacagct    1080
gctgagagga atgaatga                                                 1098

<210> SEQ ID NO 45
<211> LENGTH: 1059
<212> TYPE: DNA
<213> ORGANISM: Glycine max

<400> SEQUENCE: 45
```

-continued

```
atgtcgaatg aactagaaaa ctacgatgtt tttctcagtt ttcatggcca agattcccgt        60
tacaccttca ctggtactct ctataatgct ttgcgcagca agagaatcaa gaccttttc        120 acagaacatg aatatgatcg taaactacac actgatgaca gccaaattcc accctctact       180
cttaaagcaa ttaaggaatc aaggatttcg gtggttgttt tctcggaaaa ctatgcatcc       240
tcctcaagat gtcttgatga acttgtggcc atccttgagt gtaacaggac gataaaccaa       300
ctggtgtggc ccatctttta cgaagtgtat ccgtggcacg taaggcagca gagaggtagc       360
tatgaagcac ccatgtctaa atttgaagaa atatttggag attccaatga gagggtgaag       420
caatggagag cagctttatt tgaagtcacc aacttgaatg gatggtgtta caaaactggg       480
acgtcccagt acgaatatga attcatcgaa aagatcgtgg aatcaaccgt gcaagccttg       540
cccggatatg atgtttttct gagttttacc ggagaggata cccgctacac tttcacaggt       600
tttctctatg atgcctttcg ccgagaggga ttcaaaatct tcatggatga tgaggaattg       660
gagagtggga accaaatttc acagaagctt atgggagcaa ttgagagttc aaagatttca       720
attgttgtgc tctctgaaaa ctatgcatat tccacctggt gtcttgatga acttgccaag       780
atcattgagt gtatgaagac caacaatcaa atggtttggc caatatttta caatgtgcaa       840
aagtcggatg tatgcaatca aacaaaaagt tatggtgaag ccatgactga acatgaaaaa       900
agatttggaa aggactctga gaaggtgcag aaatggaggt ctgctttgtc tgaaatcaac       960
aacttggaag gagaccatgt caaacaaaat gagtacgtaa tgcttttaat taattactta      1020
atatatgctt ccctcttaag tgtttttgaa catctgtga                              1059
```

<210> SEQ ID NO 46
<211> LENGTH: 1113
<212> TYPE: DNA
<213> ORGANISM: Glycine max

<400> SEQUENCE: 46

```
atgtcgaatg aactaaaaaa ctatgatgtt tttctcaatt ttcatggcaa agattccggt        60
tacaccttca ctggtactct ctataatgct ttgcgcagca agagaatcaa gaccttttc        120 acaaaacatg aatatggtcg taaactacac actgatgaca gccacattcc acccttact        180 cttaaagcaa ttaaggaatc aaggatttcg gtggttgttt tgtcggaaaa ctatgcatcc       240
tcctcaagat gtcttgatga acttgtggcc atccttgagt gtaaaaggac gataaaccaa       300
ctggtgtggc ccatctttta caaagtggat ccgtcgcaag taaggcacca gaaaggtagc       360 tatgagaac acatttgtaa tttaaaaaaa aattttagag attacaacga ttccaatgag        420
agggtgaagc aatggagagc agctttatct gaagtcagca aattgagtgg atggctttac       480
aatgatcgga ggtcccagta cgaatatgaa ttcatcgaaa ggatcgtgga atcaaccgtg       540
caagccttgc ccggatatga tgttttctg agttttaccg gagaggatac ccgctacact       600
ttcacaggtt ttctctataa tgcctttcgc cgagagggat tcaaaatctt catggatgat       660
gaggaattgg agagtgggaa ccaaatttca cagaagctta tgagagcaat tgagagttca       720
aagatttcaa ttgttgtgct ctctgaaaac tatgcatatt ccacctggtg tcttgatgaa       780
cttgccaaga tcattgagtg tatgaagacc aacaatcaaa tggtttggcc aatattttac       840
aatgtgcaaa agtcggatgt atgcaatcaa acaaaaagtt atggtgaagc catgactgaa       900
catgaaaaaa gatttggaaa ggactctgag aaggtgcaga aatggaggtc tgctttgtct       960
gaaatcaaaa acttggaagg agaccatgtc aaacaaaatg agtaccaaca tgaattaatc      1020
```

```
gaaaggattg tggaaaaggt catcaaaatt gaaggtagca agcatacagc aaatcctttc    1080
cttttatcca atgacagcta cgaggaagaa tga                                 1113
```

<210> SEQ ID NO 47
<211> LENGTH: 1113
<212> TYPE: DNA
<213> ORGANISM: Glycine soja

<400> SEQUENCE: 47

```
atgtcgaatg aactaaaaaa ctatgatgtt tttctcaatt ttcatggcaa agattccggt      60
tacaccttca ctggtactct ctataatgct ttgcgcagca agagaatcaa gaccttttc     120 acaaaacatg aatatggtcg taaactacac actgatgaca gccacattcc accctttact    180
cttaaagcaa ttaaggaatc aaggatttcg gtggttgttt tgtcggaaaa ctatgcatcc    240
tcctcaagat gtcttgatga acttgtggcc atccttgagt gtaaaaggac gataaaccaa    300
ctggtgtggc ccatctttta caaagtggat ccgtcgcaag taaggcacca gaaaggtagc    360
tatggagaac acatttgtaa ttttaaaaat tttttttagag attacaacga ttccaatgag    420
agggtgaagc aatggagagc agctttatct gaagtcagca aattgagtgg atggctttac    480
aatgatcgga ggtcccagta cgaatatgaa ttcatcgaaa ggatcgtgga atcaaccgtg    540
caagccttgc ccggatatga tgtttttctg agttttaccg agaggatac ccgctacact      600 ttcacaggtt ttctctataa tgcctttcgc cgagagggat tcaaaatctt catggatgat     660
gaggaattgg agagtgggaa ccaaatttca cagaagctta tgagagcaat tgagagttca    720
aagatttcaa ttgttgtgct ctctgaaaac tatgcatatt ccacctggtg tcttgatgaa    780
cttgccaaga tcattgagtg tatgaagacc aacaatcaaa tggtttggcc aatattttac    840
aatgtgcaaa agtcggatgt atgcaatcaa acaaaaagtt atggtgaagc catgactgaa     900
catgaaaaaa gatttggaaa ggactctgag aaggtgcaga aatggaggtc tgctttgtct    960
gaaatcaaaa acttggaagg agaccatgtc aaacaaaatg agtaccaaca tgaattaatc    1020
gaaaggattg tggaaaaggt cattaaaatt gaaggtagca agcatacagc aaatcctttc    1080
cttttatcca atgacagcta cgaggaagaa tga                                 1113
```

<210> SEQ ID NO 48
<211> LENGTH: 367
<212> TYPE: PRT
<213> ORGANISM: Glycine soja

<400> SEQUENCE: 48

```
Met Ser Asn Glu Leu Glu Asn Tyr Asp Val Phe Leu Ser Phe His Gly
1               5                   10                  15

Gln Asp Ser Arg Tyr Thr Phe Thr Gly Thr Leu Tyr Asn Ala Leu Arg
            20                  25                  30

Ser Lys Arg Ile Lys Thr Phe Phe Thr Glu His Glu Tyr Asp Arg Lys
        35                  40                  45

Leu His Thr Asp Asp Ser Gln Ile Pro Pro Ser Thr Leu Lys Ala Ile
    50                  55                  60

Lys Glu Ser Arg Ile Ser Val Val Val Leu Ser Glu Asn Tyr Ala Ser
65                  70                  75                  80

Ser Ser Arg Cys Leu Asp Glu Leu Val Ala Ile Leu Glu Cys Asn Arg
                85                  90                  95

Thr Ile Asn Gln Leu Val Trp Pro Ile Phe Tyr Glu Val Tyr Pro Trp
            100                 105                 110
```

-continued

```
His Val Arg Gln Gln Arg Gly Ser Tyr Glu Ala Pro Met Ser Lys Phe
        115                 120                 125

Glu Glu Ile Phe Gly Asp Ser Asn Glu Arg Val Lys Gln Trp Arg Ala
        130                 135                 140

Ala Leu Phe Glu Val Thr Asn Leu Asn Gly Trp Cys Tyr Lys Thr Gly
145                 150                 155                 160

Thr Ser Gln Tyr Glu Tyr Glu Leu Ile Glu Lys Ile Val Glu Ser Thr
                165                 170                 175

Val Gln Ala Leu Pro Gly Tyr Asp Val Phe Leu Ser Phe Thr Gly Glu
                180                 185                 190

Asp Thr Arg Tyr Thr Phe Thr Gly Phe Leu Tyr Asn Ala Phe Arg Arg
                195                 200                 205

Glu Gly Phe Lys Ile Phe Met Asp Asp Glu Glu Leu Glu Ser Gly Asn
        210                 215                 220

Gln Ile Ser Gln Lys Leu Met Gly Ala Ile Glu Ser Ser Lys Ile Ser
225                 230                 235                 240

Ile Val Val Leu Ser Glu Asn Tyr Ala Tyr Ser Thr Trp Cys Leu Asp
                245                 250                 255

Glu Leu Ala Lys Ile Ile Glu Cys Met Lys Thr Asn Asn Gln Met Val
                260                 265                 270

Trp Pro Ile Phe Tyr Asn Val Gln Lys Ser Asp Val Cys Asn Gln Thr
                275                 280                 285

Lys Ser Tyr Gly Glu Ala Met Thr Glu His Glu Lys Arg Phe Gly Lys
        290                 295                 300

Asp Ser Glu Lys Val Gln Lys Trp Arg Ser Ala Leu Ser Glu Ile Asn
305                 310                 315                 320

Asn Leu Glu Gly Asp His Val Lys Gln Asn Glu Tyr Gln His Glu Leu
                325                 330                 335

Ile Glu Arg Ile Val Glu Lys Val Ile Lys Ile Glu Gly Ser Lys His
                340                 345                 350

Thr Ala Asn Pro Phe Leu Leu Ser His Asp Ser Tyr Glu Glu Glu
        355                 360                 365

<210> SEQ ID NO 49
<211> LENGTH: 363
<212> TYPE: PRT
<213> ORGANISM: Phaseolus vulgaris

<400> SEQUENCE: 49

Met Ser Asn Glu Pro Lys Asn Tyr Asp Val Phe Leu Ser Leu Gly Gly
1               5                   10                  15

Glu Asp Val Arg Tyr Thr Phe Thr Gly Ser Leu Phe Ser Ala Leu Cys
                20                  25                  30

Ser Lys Arg Ile Lys Thr Phe Phe Arg Glu His Glu Glu Asp Pro Glu
        35                  40                  45

Pro Tyr Thr Asn Asp Thr Asn Ile Ser Pro Ser Ser Leu Lys Ala Ile
        50                  55                  60

Gln Glu Ser Lys Ile Ser Ile Val Val Phe Ser Gln Gly Tyr Ala Ser
65                  70                  75                  80

Ser Ser Arg Cys Leu Asp Glu Leu Val Ala Ile Leu Asp Cys Trp Met
                85                  90                  95

Lys Ser Asp Gln Leu Val Trp Pro Ile Tyr Tyr Gly Val Asp Pro Ser
            100                 105                 110

Glu Val Arg Thr Gln Lys Gly Gly Phe Gly Gln Ala Met Phe Arg Val
        115                 120                 125
```

```
Arg Glu Arg Tyr Ser Thr Glu Arg Met Asn Lys Trp Arg Glu Ala Leu
    130                 135                 140

Val Glu Val Ser Arg Phe Ser Gly Trp Val Tyr Gln Met Gly Ser Lys
145                 150                 155                 160

Tyr Glu Tyr Lys Phe Ile Arg Lys Ile Val Glu Ala Ala Leu Gln Ser
                165                 170                 175

Leu Pro Arg Tyr Asp Val Phe Leu Ser Phe Cys Gly Glu Asp Thr Arg
                180                 185                 190

His Thr Leu Thr Gly Phe Leu Phe Asp Ala Ile Arg Arg Glu Gly Phe
            195                 200                 205

Lys Ile Phe Met Asp Asp Glu Glu Leu Glu Gly Gly Asn Gln Ile Ser
    210                 215                 220

Glu Thr Leu Met Gly Ala Ile Gln Ser Ser Arg Ile Ser Ile Val Val
225                 230                 235                 240

Phe Ser Glu Asn Tyr Gly Tyr Ser Thr Trp Cys Leu Asp Glu Leu Ala
                245                 250                 255

Lys Ile Thr Glu Cys Met Asn Thr Lys Asn Gln Lys Val Trp Pro Ile
                260                 265                 270

Phe Tyr Asn Val Glu Lys Leu Asp Val Cys Asn Gln Thr Lys Ser Tyr
                275                 280                 285

Gly Glu Ala Met Thr Ala His Glu Lys Arg Phe Gly Lys Asp Ser Glu
    290                 295                 300

Lys Val Leu Lys Trp Arg Ser Ala Leu Ser Gln Ile Thr Asn Leu Asp
305                 310                 315                 320

Gly Glu His Leu Ser Glu Asn Glu Phe Gln His Glu Ser Ile Glu Arg
                325                 330                 335

Ile Val Glu Arg Leu Ile Asn Ile Glu Asp Gly Lys His Ile Ala Ser
                340                 345                 350

Pro Phe Leu Ile Gln Asp Asn Asn Gly Glu Glu
    355                 360
```

```
<210> SEQ ID NO 50
<211> LENGTH: 272
<212> TYPE: PRT
<213> ORGANISM: Pisum sativum

<400> SEQUENCE: 50
```

```
Met Gln Ile Leu Val Thr Ala Arg Cys Gln Gln Glu Cys Asp Leu Met
1               5                   10                  15

Tyr Cys Gln Arg Asp Val Gln Leu Asp Pro Leu Ser Lys Glu Glu Ala
                20                  25                  30

Trp Thr Leu Phe Glu Lys His Ser Gly Ile His Asp Glu Asp Cys Ser
            35                  40                  45

Ser Ser Pro Asp Leu Ser Asn Val Ala Arg Glu Val Ala Phe Glu Cys
    50                  55                  60

Glu Gly Val Pro Arg Leu Ile Lys Asp Val Ala Ser Ser Leu Arg Asn
65                  70                  75                  80

Lys Pro Ile Asp Glu Trp Lys Ala Ser Leu Asp Ser Leu Lys His Ser
                85                  90                  95

Met Ala Lys Trp Gln Ile Phe Leu Ser Phe Arg Gly Glu Asp Thr Arg
                100                 105                 110

Tyr Ala Phe Thr Gly Ser Leu Tyr Gln Ser Leu Arg Gln Gly Gly Phe
            115                 120                 125

Lys Thr Phe Met Asp Asp Gly Gly Leu Glu Thr Gly Asp Gln Ile Ser
```

-continued

```
         130              135              140

Pro Ser Leu Leu Asn Ala Ile Glu Ala Ser Arg Leu Ser Ile Ile Val
145                 150              155              160

Leu Ser Glu Asn Tyr Ala Asn Ser Thr Trp Cys Leu Asp Glu Leu Val
                165              170              175

Lys Ile Leu Glu Cys Lys Lys Leu Lys Asn Gln Leu Val Trp Pro Ile
                180              185              190

Phe Tyr Lys Val Asp Pro Ser Asp Ile Arg His Met Arg Lys Cys Tyr
            195              200              205

Gly Lys Asp Met Ala Arg His Glu Asn Arg Phe Gly Ile Asp Ser Glu
            210              215              220

Arg Val Gln Lys Trp Lys Ser Ala Leu Asp Glu Val Cys Asn Leu Ser
225              230              235              240

Gly Lys Ala Tyr Ser Ile Gly Tyr Glu Tyr Glu Phe Ile Gln Lys Ile
                245              250              255

Val Glu His Ala Asn Leu Ile Arg Ser Arg Leu Gln Ile Arg Asn Ile
            260              265              270
```

```
<210> SEQ ID NO 51
<211> LENGTH: 355
<212> TYPE: PRT
<213> ORGANISM: Glycine max

<400> SEQUENCE: 51
```

```
Met Ser Asn Glu Leu Lys Asn Tyr Asp Val Phe Leu Asn Phe His Gly
1               5               10              15

Lys Asp Ser Gly Tyr Thr Phe Thr Gly Thr Leu Tyr Asn Ala Leu Arg
            20              25              30

Ser Lys Arg Ile Lys Thr Phe Phe Thr Lys His Glu Tyr Gly Arg Lys
        35              40              45

Leu His Thr Asp Asp Ser His Ile Pro Pro Phe Thr Leu Lys Ala Ile
    50              55              60

Lys Glu Ser Arg Ile Ser Val Val Val Leu Ser Glu Asn Tyr Ala Ser
65              70              75              80

Ser Ser Arg Cys Leu Asp Glu Leu Val Ala Ile Leu Glu Cys Lys Arg
                85              90              95

Thr Ile Asn Gln Leu Val Trp Pro Ile Phe Tyr Lys Val Asp Pro Ser
            100             105             110

Gln Val Arg His Gln Lys Gly Ser Tyr Gly Glu His Ile Cys Asn Phe
            115             120             125

Lys Lys Ile Phe Arg Asp Tyr Asn Asp Ser Asn Glu Arg Val Lys Gln
            130             135             140

Trp Arg Ala Ala Leu Ser Glu Val Ser Lys Leu Ser Gly Trp Leu Tyr
145             150             155             160

Asn Asp Arg Arg Ser Gln Tyr Glu Tyr Glu Phe Ile Glu Arg Ile Val
                165             170             175

Glu Ser Thr Val Gln Ala Leu Pro Gly Tyr Asp Val Phe Leu Ser Phe
            180             185             190

Thr Gly Glu Asp Thr Arg Tyr Thr Phe Thr Gly Phe Leu Tyr Asn Ala
            195             200             205

Phe Arg Arg Glu Gly Phe Lys Ile Phe Met Asp Asp Glu Glu Leu Glu
            210             215             220

Ser Gly Asn Gln Ile Ser Gln Lys Leu Met Arg Ala Ile Glu Ser Ser
225             230             235             240
```

-continued

```
Lys Ile Ser Ile Val Val Leu Ser Glu Asn Tyr Ala Tyr Ser Thr Trp
                245                 250                 255

Cys Leu Asp Glu Leu Ala Lys Ile Ile Glu Cys Met Lys Thr Asn Asn
            260                 265                 270

Gln Met Val Trp Pro Ile Phe Tyr Asn Val Gln Lys Ser Asp Val Cys
            275                 280                 285

Asn Gln Thr Lys Ser Tyr Gly Glu Ala Met Thr Glu His Glu Lys Arg
        290                 295                 300

Phe Gly Lys Asp Ser Glu Lys Val Gln Lys Trp Arg Ser Ala Leu Ser
305                 310                 315                 320

Glu Ile Lys Asn Leu Glu Gly Asp His Val Lys Gln Asn Glu Tyr Val
                325                 330                 335

Met Leu Leu Ile Asn Tyr Leu Ile Tyr Ala Ser Leu Leu Ser Val Phe
            340                 345                 350

Asp His Leu
        355

<210> SEQ ID NO 52
<211> LENGTH: 370
<212> TYPE: PRT
<213> ORGANISM: Glycine max

<400> SEQUENCE: 52

Met Ser Asn Glu Leu Lys Asn Tyr Asp Val Phe Leu Asn Phe His Gly
1               5                   10                  15

Lys Asp Ser Gly Tyr Thr Phe Thr Gly Thr Leu Tyr Asn Ala Leu Arg
            20                  25                  30

Ser Lys Arg Ile Lys Thr Phe Phe Thr Lys His Glu Tyr Gly Arg Lys
        35                  40                  45

Leu His Thr Asp Asp Ser His Ile Pro Pro Phe Thr Leu Lys Ala Ile
    50                  55                  60

Lys Glu Ser Arg Ile Ser Val Val Val Leu Ser Glu Asn Tyr Ala Ser
65                  70                  75                  80

Ser Ser Arg Cys Leu Asp Glu Leu Val Ala Ile Leu Glu Cys Lys Arg
            85                  90                  95

Thr Ile Asn Gln Leu Val Trp Pro Ile Phe Tyr Lys Val Asp Pro Ser
            100                 105                 110

Gln Val Arg His Gln Lys Gly Ser Tyr Gly Glu His Ile Cys Asn Phe
        115                 120                 125

Lys Lys Ile Phe Arg Asp Tyr Asn Asp Ser Asn Glu Arg Val Lys Gln
        130                 135                 140

Trp Arg Ala Ala Leu Ser Glu Val Ser Lys Leu Ser Gly Trp Leu Tyr
145                 150                 155                 160

Asn Asp Arg Arg Ser Gln Tyr Glu Tyr Glu Phe Ile Glu Arg Ile Val
                165                 170                 175

Glu Ser Thr Val Gln Ala Leu Pro Gly Tyr Asp Val Phe Leu Ser Phe
            180                 185                 190

Thr Gly Glu Asp Thr Arg Tyr Thr Phe Thr Gly Phe Leu Tyr Asn Ala
            195                 200                 205

Phe Arg Arg Glu Gly Phe Lys Ile Phe Met Asp Asp Glu Glu Leu Glu
        210                 215                 220

Ser Gly Asn Gln Ile Ser Gln Lys Leu Met Arg Ala Ile Glu Ser Ser
225                 230                 235                 240

Lys Ile Ser Ile Val Val Leu Ser Glu Asn Tyr Ala Tyr Ser Thr Trp
                245                 250                 255
```

```
Cys Leu Asp Glu Leu Ala Lys Ile Ile Glu Cys Met Lys Thr Asn Asn
            260                 265                 270

Gln Met Val Trp Pro Ile Phe Tyr Asn Val Gln Lys Ser Asp Val Cys
            275                 280                 285

Asn Gln Thr Lys Ser Tyr Gly Glu Ala Met Thr Glu His Glu Lys Arg
            290                 295                 300

Phe Gly Lys Asp Ser Glu Lys Val Gln Lys Trp Arg Ser Ala Leu Ser
305                 310                 315                 320

Glu Ile Lys Asn Leu Glu Gly Asp His Val Lys Gln Asn Glu Tyr Gln
                325                 330                 335

His Glu Leu Ile Glu Arg Ile Val Glu Lys Val Ile Lys Ile Glu Gly
            340                 345                 350

Ser Lys His Thr Ala Asn Pro Phe Leu Leu Ser Asn Asp Ser Tyr Glu
            355                 360                 365

Glu Glu
    370

<210> SEQ ID NO 53
<211> LENGTH: 365
<212> TYPE: PRT
<213> ORGANISM: Vigna radiata

<400> SEQUENCE: 53

Met Ser Cys Glu Pro Lys Ser Tyr Asp Val Phe Leu Ser Leu Gly Gly
1               5                   10                  15

Lys Asp Val Arg Tyr Thr Phe Thr Gly Asn Leu Phe Asn Ala Leu Arg
            20                  25                  30

Ser Lys Arg Ile Lys Thr Leu Phe Arg Glu His Glu Tyr Glu Pro Glu
        35                  40                  45

Leu His Thr His Gln Thr Asn Ile Ser Pro Ser Val Leu Lys Ala Leu
    50                  55                  60

Gln Thr Ser Lys Ile Ser Ile Val Val Phe Ser Pro Glu Tyr Ala Ser
65                  70                  75                  80

Ser Ser Arg Arg Leu Asp Glu Leu Val Ala Ile Leu Glu Cys Arg Met
                85                  90                  95

Arg Thr Asn Gln Leu Val Trp Pro Ile Phe Tyr Gly Val Glu Pro Thr
            100                 105                 110

Asp Val Arg Phe Gln Arg Gly Arg Tyr Glu Gln Ala Met Asn Thr Phe
            115                 120                 125

Glu Glu Arg Tyr Ser Pro Glu Arg Met Asn Lys Trp Arg Ser Ala Leu
        130                 135                 140

Ala Glu Val Ser Asn Leu Ser Gly Trp Phe Tyr Gln Lys Glu His Lys
145                 150                 155                 160

Tyr Glu Tyr Lys Phe Ile Arg Lys Ile Val Glu Ala Ala Val Gln Ser
                165                 170                 175

Leu Ser Arg Tyr Asp Val Phe Leu Ser Phe Cys Gly Glu Asp Thr Arg
            180                 185                 190

Tyr Thr Leu Thr Gly Phe Leu Tyr Asn Ala Leu Ser Arg Glu Gly Phe
            195                 200                 205

Lys Ile Phe Met Asp Asp Glu Glu Leu Glu Gly Gly Asn Gln Ile Ser
        210                 215                 220

Gln Lys Leu Met Gly Ala Ile Glu Ser Ser Arg Val Ser Ile Val Val
225                 230                 235                 240

Phe Ser Glu Asn Tyr Gly Tyr Ser Thr Trp Cys Leu Asp Glu Leu Ala
```

-continued

```
                    245                 250                 255

Lys Ile Thr Glu Cys Met Lys Thr Lys Asn Gln Met Val Trp Pro Ile
            260                 265                 270

Phe Tyr Asn Val Glu Lys Ser Asp Val Cys Asn Gln Thr Lys Ser Tyr
            275                 280                 285

Gly Glu Ala Met Thr Ala His Glu Lys Arg Phe Gly Lys Asp Ser Glu
            290                 295                 300

Lys Val Gln Lys Trp Arg Ser Ala Leu Ser Gln Ile Thr Asn Leu Glu
305                 310                 315                 320

Gly Glu His Leu Ser Glu Asn Glu Phe Gln His Glu Ser Ile Glu Lys
                325                 330                 335

Ile Val Glu Arg Leu Ile Asn Ile Glu Asp Gly Lys His Ile Ala Ser
                340                 345                 350

Pro Phe Leu Val Pro Met Thr Ala Thr Glu Asn Asn Glu
                355                 360                 365

<210> SEQ ID NO 54
<211> LENGTH: 170
<212> TYPE: PRT
<213> ORGANISM: Pisum sativum

<400> SEQUENCE: 54

Met Ser Leu Pro Lys Tyr Asp Val Phe Ile Ser Phe Arg Gly Asp Asp
1               5                   10                  15

Thr Arg Asp Asn Phe Thr Ser His Leu Tyr Ala Glu Leu Arg Arg Lys
                20                  25                  30

Asn Ile Glu Thr Phe Ile Asp Tyr Arg Leu Gly Arg Gly Glu Glu Ile
            35                  40                  45

Phe Pro Thr Leu Cys Lys Ala Ile Glu Glu Ser Ala Ile Tyr Val Val
            50                  55                  60

Ile Leu Ser Glu His Tyr Ala Ser Ser Thr Trp Cys Leu Glu Glu Leu
65                  70                  75                  80

Thr Lys Ile Leu Glu Cys Lys Glu Arg His Gly Arg Lys Val Ile Pro
                85                  90                  95

Val Phe Tyr Lys Val Asp Pro Ser Thr Val Arg His Gln Thr Gln Ser
            100                 105                 110

Tyr Ala Asp Asp Phe Val Lys His Gln Gln Arg Phe Gly Asp Lys Val
            115                 120                 125

Asp Ala Trp Lys Ala Ala Leu Thr Gln Ile Ala Asn Leu Ser Gly Met
            130                 135                 140

Asp Ser His Lys Ile Arg Asp Asp Leu Asn Gly Ala Gly Met Pro Val
145                 150                 155                 160

Phe His Pro Asn Ser Ser Cys Ile Lys Leu
                165                 170

<210> SEQ ID NO 55
<211> LENGTH: 365
<212> TYPE: PRT
<213> ORGANISM: Phaseolus vulgaris

<400> SEQUENCE: 55

Met Ser Asn Glu Pro Lys Asn Tyr Asp Val Phe Leu Ser Leu Gly Gly
1               5                   10                  15

Glu Asp Val Arg Tyr Thr Phe Thr Gly Asn Leu Phe Tyr Ala Leu Cys
                20                  25                  30

Ser Lys Arg Ile Lys Thr Phe Phe Arg Glu His Glu His Asp Pro Glu
```

-continued

```
                35                    40                    45

Leu Tyr Thr Asn Asp Thr Asn Ile Ser Pro Ser Ala Leu Lys Ala Ile
    50                    55                    60

Gln Glu Ser Lys Ile Ser Met Val Val Phe Ser Gln Gln Tyr Ala Ser
65                    70                    75                    80

Ser Ser Arg Cys Leu Asp Glu Leu Val Ala Ile Leu Asp Cys Arg Met
                85                    90                    95

Lys Ser Asp Gln Leu Val Trp Pro Ile Tyr Tyr Gly Val Asp Pro Ser
                100                   105                   110

Asp Leu Val Thr His Glu Gly Arg Phe Gly Gln Ala Met Cys Arg Val
                115                   120                   125

Glu Glu Lys Tyr Ser Thr Glu Arg Ile Asn Lys Trp Arg Glu Ala Leu
    130                   135                   140

Val Gln Val Gly Gln Leu Ser Gly Trp Val Tyr Gln Arg Arg Phe Lys
145                   150                   155                   160

Tyr Glu Tyr Lys Phe Ile Arg Lys Ile Val Lys Ala Ala Val Gln Ser
                165                   170                   175

Leu Pro Arg Tyr Asp Val Phe Leu Ser Phe Cys Gly Glu Asp Thr Arg
                180                   185                   190

Tyr Thr Leu Ala Gly Phe Leu Tyr Asn Ala Ile Ser Arg Glu Gly Phe
                195                   200                   205

Lys Ile Phe Met Asp Asp Glu Glu Leu Glu Gly Gly Asn Gln Ile Ser
    210                   215                   220

Glu Thr Leu Met Gly Ala Ile Glu Ser Ser Arg Ile Ser Ile Val Val
225                   230                   235                   240

Phe Ser Glu Asn Tyr Gly Tyr Ser Thr Trp Cys Leu Asp Glu Leu Ala
                245                   250                   255

Lys Ile Thr Glu Cys Met Asn Thr Lys Asn Gln Lys Val Trp Pro Ile
                260                   265                   270

Phe Tyr Asn Val Glu Lys Met Asp Val Cys Asn Gln Thr Lys Ser Tyr
                275                   280                   285

Gly Glu Ala Met Thr Ala His Gly Lys Met Phe Gly Lys Glu Ser Glu
    290                   295                   300

Lys Val Gln Lys Trp Lys Ser Ala Leu Ser Gln Ile Thr Asn Leu Asp
305                   310                   315                   320

Gly Glu His Leu Ile Glu Asn Glu Phe Gln His Glu Ser Ile Glu Arg
                325                   330                   335

Ile Val Glu Gln Leu Ile Asn Ile Glu Asp Gly Lys His Ile Ala Ser
                340                   345                   350

Pro Phe Leu Val Pro Thr Thr Ala Ala Glu Arg Asn Glu
                355                   360                   365

<210> SEQ ID NO 56
<211> LENGTH: 352
<212> TYPE: PRT
<213> ORGANISM: Glycine max

<400> SEQUENCE: 56

Met Ser Asn Glu Leu Glu Asn Tyr Asp Val Phe Leu Ser Phe His Gly
1                     5                     10                    15

Gln Asp Ser Arg Tyr Thr Phe Thr Gly Thr Leu Tyr Asn Ala Leu Arg
                20                    25                    30

Ser Lys Arg Ile Lys Thr Phe Phe Thr Glu His Glu Tyr Asp Arg Lys
    35                    40                    45
```

-continued

Leu His Thr Asp Asp Ser Gln Ile Pro Pro Ser Thr Leu Lys Ala Ile
    50                  55                  60

Lys Glu Ser Arg Ile Ser Val Val Val Phe Ser Glu Asn Tyr Ala Ser
65                  70                  75                  80

Ser Ser Arg Cys Leu Asp Glu Leu Val Ala Ile Leu Glu Cys Asn Arg
                85                  90                  95

Thr Ile Asn Gln Leu Val Trp Pro Ile Phe Tyr Glu Val Tyr Pro Trp
            100                 105                 110

His Val Arg Gln Gln Arg Gly Ser Tyr Glu Ala Pro Met Ser Lys Phe
            115                 120                 125

Glu Glu Ile Phe Gly Asp Ser Asn Glu Arg Val Lys Gln Trp Arg Ala
    130                 135                 140

Ala Leu Phe Glu Val Thr Asn Leu Asn Gly Trp Cys Tyr Lys Thr Gly
145                 150                 155                 160

Thr Ser Gln Tyr Glu Tyr Glu Phe Ile Glu Lys Ile Val Glu Ser Thr
                165                 170                 175

Val Gln Ala Leu Pro Gly Tyr Asp Val Phe Leu Ser Phe Thr Gly Glu
            180                 185                 190

Asp Thr Arg Tyr Thr Phe Thr Gly Phe Leu Tyr Asp Ala Phe Arg Arg
            195                 200                 205

Glu Gly Phe Lys Ile Phe Met Asp Asp Glu Glu Leu Glu Ser Gly Asn
    210                 215                 220

Gln Ile Ser Gln Lys Leu Met Gly Ala Ile Glu Ser Ser Lys Ile Ser
225                 230                 235                 240

Ile Val Val Leu Ser Glu Asn Tyr Ala Tyr Ser Thr Trp Cys Leu Asp
                245                 250                 255

Glu Leu Ala Lys Ile Ile Glu Cys Met Lys Thr Asn Asn Gln Met Val
            260                 265                 270

Trp Pro Ile Phe Tyr Asn Val Gln Lys Ser Asp Val Cys Asn Gln Thr
            275                 280                 285

Lys Ser Tyr Gly Glu Ala Met Thr Glu His Glu Lys Arg Phe Gly Lys
    290                 295                 300

Asp Ser Glu Lys Val Gln Lys Trp Arg Ser Ala Leu Ser Glu Ile Asn
305                 310                 315                 320

Asn Leu Glu Gly Asp His Val Lys Gln Asn Glu Tyr Val Met Leu Leu
                325                 330                 335

Ile Asn Tyr Leu Ile Tyr Ala Ser Leu Leu Ser Val Phe Glu His Leu
            340                 345                 350

<210> SEQ ID NO 57
<211> LENGTH: 370
<212> TYPE: PRT
<213> ORGANISM: Glycine max

<400> SEQUENCE: 57

Met Ser Asn Glu Leu Lys Asn Tyr Asp Val Phe Leu Asn Phe His Gly
1               5                   10                  15

Lys Asp Ser Gly Tyr Thr Phe Thr Gly Thr Leu Tyr Asn Ala Leu Arg
                20                  25                  30

Ser Lys Arg Ile Lys Thr Phe Phe Thr Lys His Glu Tyr Gly Arg Lys
            35                  40                  45

Leu His Thr Asp Asp Ser His Ile Pro Pro Phe Thr Leu Lys Ala Ile
    50                  55                  60

Lys Glu Ser Arg Ile Ser Val Val Val Leu Ser Glu Asn Tyr Ala Ser
65                  70                  75                  80

-continued

```
Ser Ser Arg Cys Leu Asp Glu Leu Val Ala Ile Leu Glu Cys Lys Arg
            85                  90                  95

Thr Ile Asn Gln Leu Val Trp Pro Ile Phe Tyr Lys Val Asp Pro Ser
            100                 105                 110

Gln Val Arg His Gln Lys Gly Ser Tyr Gly Glu His Ile Cys Asn Leu
            115                 120                 125

Lys Lys Asn Phe Arg Asp Tyr Asn Asp Ser Asn Glu Arg Val Lys Gln
            130                 135                 140

Trp Arg Ala Ala Leu Ser Glu Val Ser Lys Leu Ser Gly Trp Leu Tyr
145                 150                 155                 160

Asn Asp Arg Arg Ser Gln Tyr Glu Tyr Glu Phe Ile Glu Arg Ile Val
                165                 170                 175

Glu Ser Thr Val Gln Ala Leu Pro Gly Tyr Asp Val Phe Leu Ser Phe
            180                 185                 190

Thr Gly Glu Asp Thr Arg Tyr Thr Phe Thr Gly Phe Leu Tyr Asn Ala
            195                 200                 205

Phe Arg Arg Glu Gly Phe Lys Ile Phe Met Asp Asp Glu Glu Leu Glu
    210                 215                 220

Ser Gly Asn Gln Ile Ser Gln Lys Leu Met Arg Ala Ile Glu Ser Ser
225                 230                 235                 240

Lys Ile Ser Ile Val Val Leu Ser Glu Asn Tyr Ala Tyr Ser Thr Trp
                245                 250                 255

Cys Leu Asp Glu Leu Ala Lys Ile Ile Glu Cys Met Lys Thr Asn Asn
            260                 265                 270

Gln Met Val Trp Pro Ile Phe Tyr Asn Val Gln Lys Ser Asp Val Cys
            275                 280                 285

Asn Gln Thr Lys Ser Tyr Gly Glu Ala Met Thr Glu His Glu Lys Arg
    290                 295                 300

Phe Gly Lys Asp Ser Glu Lys Val Gln Lys Trp Arg Ser Ala Leu Ser
305                 310                 315                 320

Glu Ile Lys Asn Leu Glu Gly Asp His Val Lys Gln Asn Glu Tyr Gln
                325                 330                 335

His Glu Leu Ile Glu Arg Ile Val Glu Lys Val Ile Lys Ile Glu Gly
            340                 345                 350

Ser Lys His Thr Ala Asn Pro Phe Leu Leu Ser Asn Asp Ser Tyr Glu
            355                 360                 365

Glu Glu
    370
```

```
<210> SEQ ID NO 58
<211> LENGTH: 370
<212> TYPE: PRT
<213> ORGANISM: Glycine soja

<400> SEQUENCE: 58
```

```
Met Ser Asn Glu Leu Lys Asn Tyr Asp Val Phe Leu Asn Phe His Gly
1               5                   10                  15

Lys Asp Ser Gly Tyr Thr Phe Thr Gly Thr Leu Tyr Asn Ala Leu Arg
            20                  25                  30

Ser Lys Arg Ile Lys Thr Phe Phe Thr Lys His Glu Tyr Gly Arg Lys
        35                  40                  45

Leu His Thr Asp Asp Ser His Ile Pro Pro Phe Thr Leu Lys Ala Ile
    50                  55                  60

Lys Glu Ser Arg Ile Ser Val Val Val Leu Ser Glu Asn Tyr Ala Ser
```

-continued

```
65            70            75            80

Ser Ser Arg Cys Leu Asp Glu Leu Val Ala Ile Leu Glu Cys Lys Arg
            85            90            95

Thr Ile Asn Gln Leu Val Trp Pro Ile Phe Tyr Lys Val Asp Pro Ser
            100           105           110

Gln Val Arg His Gln Lys Gly Ser Tyr Gly Glu His Ile Cys Asn Phe
            115           120           125

Lys Asn Phe Phe Arg Asp Tyr Asn Asp Ser Asn Glu Arg Val Lys Gln
    130           135           140

Trp Arg Ala Ala Leu Ser Glu Val Ser Lys Leu Ser Gly Trp Leu Tyr
145           150           155           160

Asn Asp Arg Arg Ser Gln Tyr Glu Tyr Glu Phe Ile Glu Arg Ile Val
            165           170           175

Glu Ser Thr Val Gln Ala Leu Pro Gly Tyr Asp Val Phe Leu Ser Phe
            180           185           190

Thr Gly Glu Asp Thr Arg Tyr Thr Phe Thr Gly Phe Leu Tyr Asn Ala
            195           200           205

Phe Arg Arg Glu Gly Phe Lys Ile Phe Met Asp Asp Glu Glu Leu Glu
    210           215           220

Ser Gly Asn Gln Ile Ser Gln Lys Leu Met Arg Ala Ile Glu Ser Ser
225           230           235           240

Lys Ile Ser Ile Val Val Leu Ser Glu Asn Tyr Ala Tyr Ser Thr Trp
            245           250           255

Cys Leu Asp Glu Leu Ala Lys Ile Ile Glu Cys Met Lys Thr Asn Asn
            260           265           270

Gln Met Val Trp Pro Ile Phe Tyr Asn Val Gln Lys Ser Asp Val Cys
            275           280           285

Asn Gln Thr Lys Ser Tyr Gly Glu Ala Met Thr Glu His Glu Lys Arg
    290           295           300

Phe Gly Lys Asp Ser Glu Lys Val Gln Lys Trp Arg Ser Ala Leu Ser
305           310           315           320

Glu Ile Lys Asn Leu Glu Gly Asp His Val Lys Gln Asn Glu Tyr Gln
            325           330           335

His Glu Leu Ile Glu Arg Ile Val Glu Lys Val Ile Lys Ile Glu Gly
            340           345           350

Ser Lys His Thr Ala Asn Pro Phe Leu Leu Ser Asn Asp Ser Tyr Glu
    355           360           365

Glu Glu
370
```

<210> SEQ ID NO 59
<211> LENGTH: 2778
<212> TYPE: DNA
<213> ORGANISM: Cajanus cajan

<400> SEQUENCE: 59

```
atggcagaca gtgtggtttc ctttgtttta gatcacttgt cccaactggt ggaacatgaa        60
gcaaggttgc taagtggcgt ggaagacaag gtgaagtccc tcgagaggga gcttcagatg       120
atcaacgtca tcctaagaac cacaaacagc aacaacgaca ttcagaaaac agtggtgagc       180
caaatcagag atgtggccca tgaagctgag gatgtcattg acacgtacgt tgccaaagtg       240
gccctgcaca acaggagaac catgctgggg aggctactcc atggagttga ccaaacaaag       300
ttgctccatg acgtatccga gaaaatagac gagatcataa caactctcaa ccagatacgt       360
```

-continued

```
gaaaacaaga tcaaatacag cgagttccaa gaaagaaatc atcaatccat agcagaagag    420
gaggaggagg agaaggagag ggagaggtta cttcacaagc taagaagaaa tgtagaggag    480
gaacatgtag tgggtttttat ccgtggatct caagcaatca tcaagctact caaggaaggt    540
ggctcacggc gtaatgtggt ctccatcatc ggcatggggg ggttgggcaa gaccaccctt    600
gcccgaaaag tttataatga tagcaaggtg aaacaaggct ttagttgttg tgtttgggtg    660
tacgtgtcaa acgagtgtag agctaaggag cttttgctta gtcttcttaa gcatttgagg    720
ccaaacctcg aaactgaact tcaagaagaa aacaacaaag gaaaaaaatt cactgaagaa    780
caagacattt ttaacttgag tgtggaggag ctgaagaaac tggtgcggca atacttggag    840
aggaaaacaa ggtatctggt ggtcctcgat gacttgtgga aaacacaaga ttgggacgag    900
gtgcaagatg cttttcccga caacaacaga ggcaacagaa tattgatcac tagtcgtttg    960
aaagaggtgg ccttgcatac tagtcttcat cctccatact accttcaatt tctcagccaa   1020
gaagaaagct gggagctctt tcgtaggaaa gtgtttagag gggaagaatg ccctttttgaa   1080 ctagagcctc taggcaaaca aatagtggca agttgtcgcg gtttgccact ctctattgtt   1140
gtattagcag gattgctagc caacaaggaa aagtcacaca gggaatggtc caaagtggtg   1200
ggtcacgtca actggtatct tactcaagac gagactcaag tgaaggatat agttctgaag   1260
ctcagttatg ataacttgcc aagaagattg aaaccatgct ttctatattt tgggatattc   1320
cctgaagact ttgaaatccc tgttaggcca ttactacaac aatgggttgc agaagggttt   1380
atacaagaaa caagaaatag agacccagat gatgtggcag aagactactt gtacgagctc   1440
attgatcgta gtttggtcca agtagcagca ataaagacta gtggaggtgt gaaaacttgt   1500
cacatccatg atcttctccg agatctttgt gtatcgcaga gcaaagggga caagattttt   1560
gaagtctgct cagataatga cattcaaatt ctaacaaaac ctcgcaggtt gtccttccat   1620
tgtgacatgg gccactacat ttcttcaagc aacaaagacc attcatgtat ccgttctttg   1680
ttcttctttg gaatatattc caattttact gggaacgagt gggaatggct tttcaaaggc   1740
ttcaaattgg ttcgagtgtt agagcttgga aaaaaccatt gcgcaggaaa gatcccatct   1800
aatttggggg actttatcca cttaaggtat ttgagaattg actcgaattt tggtataatt   1860
attccaactt ccatacttac ccttcagaat ttacaaacag tagatttagg taattggttt   1920
agggaaatcc caatttgttt ccctgctcaa atgtggaagc tcaaacattt aaggcacctg   1980
tatgggcaag gacctgtgaa gcttcaaggc cactattcag gatcaaatga ggttatgtgg   2040
aatctccgaa ccatcttccc cattgatatt gatacacaaa cattgtctct gatgaagaaa   2100
ggaagcttcc ccaatcttgt gaaattgggg ttgtcaatca attcggaccg ccaaggtaag   2160
tggccaaagt tgttgcagag cttacaagaa ttaagtcatt tgaatatctt aaagatttgc   2220
ctccgagggg attttgatgc ttcaataggc acagtgtcaa gcatatggcg gtttggttgt   2280
gagccacagg agctattaca aagcctaggg ttgttgactc atataactac gttgaaaatc   2340
accaatatct gcagccttat gataacggtt cctccaaatg tcaccaagtt aacattgcgt   2400
ggtattagta gcatcactag ggaggggctg aatgcgttga gaaatcacac caaactccaa   2460
attttgagtc tatatggaga ctatggctct aacattaacc tcaattgtgt tgtaggcggc   2520
tttccacaac tgcaagtatt gcaattgaaa aagttcacct ctgtaaattg gaaattaggc   2580
aatggtgcaa tgccacgtct tcacactcta gtcatcatca actgtcaaag tttagatgat   2640
cttccaaatg aattgtggtc tctcactgcc ttcagaaaac tgcatgtaaa acaaccctca   2700
caaccaatgc ttcgtatgct acgggatttg aaaataaagg ataggggttca agtcatagtc   2760
```
gatgatcatg acaactag                                                    2778

<210> SEQ ID NO 60
<211> LENGTH: 925
<212> TYPE: PRT
<213> ORGANISM: Cajanus cajan

<400> SEQUENCE: 60

Met Ala Asp Ser Val Val Ser Phe Val Leu Asp His Leu Ser Gln Leu
1               5                   10                  15

Val Glu His Glu Ala Arg Leu Leu Ser Gly Val Glu Asp Lys Val Lys
                20                  25                  30

Ser Leu Glu Arg Glu Leu Gln Met Ile Asn Val Ile Leu Arg Thr Thr
            35                  40                  45

Asn Ser Asn Asn Asp Ile Gln Lys Thr Val Val Ser Gln Ile Arg Asp
        50                  55                  60

Val Ala His Glu Ala Glu Asp Val Ile Asp Thr Tyr Val Ala Lys Val
65                  70                  75                  80

Ala Leu His Asn Arg Arg Thr Met Leu Gly Arg Leu Leu His Gly Val
                85                  90                  95

Asp Gln Thr Lys Leu Leu His Asp Val Ser Glu Lys Ile Asp Glu Ile
            100                 105                 110

Ile Thr Thr Leu Asn Gln Ile Arg Glu Asn Lys Ile Lys Tyr Ser Glu
        115                 120                 125

Phe Gln Glu Arg Asn His Gln Ser Ile Ala Glu Glu Glu Glu Glu Glu
        130                 135                 140

Lys Glu Arg Glu Arg Leu Leu His Lys Leu Arg Arg Asn Val Glu Glu
145                 150                 155                 160

Glu His Val Val Gly Phe Ile Arg Gly Ser Gln Ala Ile Ile Lys Leu
                165                 170                 175

Leu Lys Glu Gly Gly Ser Arg Arg Asn Val Val Ser Ile Ile Gly Met
            180                 185                 190

Gly Gly Leu Gly Lys Thr Thr Leu Ala Arg Lys Val Tyr Asn Asp Ser
            195                 200                 205

Lys Val Lys Gln Gly Phe Ser Cys Cys Val Trp Val Tyr Val Ser Asn
        210                 215                 220

Glu Cys Arg Ala Lys Glu Leu Leu Leu Ser Leu Leu Lys His Leu Arg
225                 230                 235                 240

Pro Asn Leu Glu Thr Glu Leu Gln Glu Glu Asn Asn Lys Gly Lys Lys
                245                 250                 255

Phe Thr Glu Glu Gln Asp Ile Phe Asn Leu Ser Val Glu Glu Leu Lys
            260                 265                 270

Lys Leu Val Arg Gln Tyr Leu Glu Arg Lys Thr Arg Tyr Leu Val Val
            275                 280                 285

Leu Asp Asp Leu Trp Lys Thr Gln Asp Trp Asp Glu Val Gln Asp Ala
        290                 295                 300

Phe Pro Asp Asn Asn Arg Gly Asn Arg Ile Leu Ile Thr Ser Arg Leu
305                 310                 315                 320

Lys Glu Val Ala Leu His Thr Ser Leu His Pro Pro Tyr Tyr Leu Gln
                325                 330                 335

Phe Leu Ser Gln Glu Glu Ser Trp Glu Leu Phe Arg Arg Lys Val Phe
            340                 345                 350

Arg Gly Glu Glu Cys Pro Phe Glu Leu Glu Pro Leu Gly Lys Gln Ile
            355                 360                 365

-continued

```
Val Ala Ser Cys Arg Gly Leu Pro Leu Ser Ile Val Val Leu Ala Gly
    370                 375             380

Leu Leu Ala Asn Lys Glu Lys Ser His Arg Glu Trp Ser Lys Val Val
385                 390             395                 400

Gly His Val Asn Trp Tyr Leu Thr Gln Asp Glu Thr Gln Val Lys Asp
                405             410                 415

Ile Val Leu Lys Leu Ser Tyr Asp Asn Leu Pro Arg Arg Leu Lys Pro
                420             425             430

Cys Phe Leu Tyr Phe Gly Ile Phe Pro Glu Asp Phe Glu Ile Pro Val
            435             440             445

Arg Pro Leu Leu Gln Gln Trp Val Ala Glu Gly Phe Ile Gln Glu Thr
    450             455             460

Arg Asn Arg Asp Pro Asp Asp Val Ala Glu Asp Tyr Leu Tyr Glu Leu
465             470             475                 480

Ile Asp Arg Ser Leu Val Gln Val Ala Ala Ile Lys Thr Ser Gly Gly
                485             490             495

Val Lys Thr Cys His Ile His Asp Leu Leu Arg Asp Leu Cys Val Ser
            500             505             510

Gln Ser Lys Gly Asp Lys Ile Phe Glu Val Cys Ser Asp Asn Asp Ile
    515             520             525

Gln Ile Leu Thr Lys Pro Arg Arg Leu Ser Phe His Cys Asp Met Gly
    530             535             540

His Tyr Ile Ser Ser Ser Asn Lys Asp His Ser Cys Ile Arg Ser Leu
545             550             555             560

Phe Phe Phe Gly Ile Tyr Ser Asn Phe Thr Gly Asn Glu Trp Glu Trp
                565             570             575

Leu Phe Lys Gly Phe Lys Leu Val Arg Val Leu Glu Leu Gly Lys Asn
            580             585             590

His Cys Ala Gly Lys Ile Pro Ser Asn Leu Gly Asp Phe Ile His Leu
    595             600             605

Arg Tyr Leu Arg Ile Asp Ser Asn Phe Gly Ile Ile Ile Pro Thr Ser
    610             615             620

Ile Leu Thr Leu Gln Asn Leu Gln Thr Val Asp Leu Gly Asn Trp Phe
625             630             635             640

Arg Glu Ile Pro Ile Cys Phe Pro Ala Gln Met Trp Lys Leu Lys His
                645             650             655

Leu Arg His Leu Tyr Gly Gln Gly Pro Val Lys Leu Gln Gly His Tyr
            660             665             670

Ser Gly Ser Asn Glu Val Met Trp Asn Leu Arg Thr Ile Phe Pro Ile
    675             680             685

Asp Ile Asp Thr Gln Thr Leu Ser Leu Met Lys Lys Gly Ser Phe Pro
    690             695             700

Asn Leu Val Lys Leu Gly Leu Ser Ile Asn Ser Asp Arg Gln Gly Lys
705             710             715                 720

Trp Pro Lys Leu Leu Gln Ser Leu Gln Glu Leu Ser His Leu Asn Ile
            725             730             735

Leu Lys Ile Cys Leu Arg Gly Asp Phe Asp Ala Ser Ile Gly Thr Val
            740             745             750

Ser Ser Ile Trp Arg Phe Gly Cys Glu Pro Gln Glu Leu Leu Gln Ser
    755             760             765

Leu Gly Leu Leu Thr His Ile Thr Thr Leu Lys Ile Thr Asn Ile Cys
770             775             780
```

-continued

```
Ser Leu Met Ile Thr Val Pro Pro Asn Val Thr Lys Leu Thr Leu Arg
785             790             795             800

Gly Ile Ser Ser Ile Thr Arg Glu Gly Leu Asn Ala Leu Arg Asn His
                805             810             815

Thr Lys Leu Gln Ile Leu Ser Leu Tyr Gly Asp Tyr Gly Ser Asn Ile
            820             825             830

Asn Leu Asn Cys Val Val Gly Gly Phe Pro Gln Leu Gln Val Leu Gln
        835             840             845

Leu Lys Lys Phe Thr Ser Val Asn Trp Lys Leu Gly Asn Gly Ala Met
        850             855             860

Pro Arg Leu His Thr Leu Val Ile Ile Asn Cys Gln Ser Leu Asp Asp
865             870             875             880

Leu Pro Asn Glu Leu Trp Ser Leu Thr Ala Phe Arg Lys Leu His Val
            885             890             895

Lys Gln Pro Ser Gln Pro Met Leu Arg Met Leu Arg Asp Leu Lys Ile
            900             905             910

Lys Asp Arg Val Gln Val Ile Val Asp Asp His Asp Asn
        915             920             925
```

POLYNUCLEOTIDES AND METHODS FOR TRANSFERRING RESISTANCE TO ASIAN SOYBEAN RUST

CROSS REFERENCE TO RELATED APPLICATIONS

This application is a national stage entry under 35 USC § 371(b) of PCT/US2021/064348, filed on Dec. 20, 2021, which claims the benefit of U.S. Provisional Application No. 63/130,261, filed Dec. 23, 2020, both of which is are hereby incorporated herein in its their entirety by reference.

REFERENCE TO SEQUENCE LISTING SUBMITTED ELECTRONICALLY

The official copy of the sequence listing is submitted electronically via EFS-Web as an ASCII formatted sequence listing with a file named "RTS21584B-WO-PCT_Sequence-Listing_ST25" created on Dec. 3, 2021, and having a size of 163 kilobytes and is filed concurrently with the specification. The sequence listing contained in this ASCII formatted document is part of the specification and is herein incorporated by reference in its entirety.

FIELD

The present disclosure relates to compositions and methods useful in enhancing pathogen resistance in legume plants, and more particularly in soybean plants, by providing to the plants a gene or gene(s) that are associated with resistance to the causal agent of Asian soybean rust (ASR). The disclosure further relates to polynucleotides capable of enhancing resistance in legumes to ASR and methods of using these polynucleotide sequences to make a transgenic legume plant that is resistant to ASR.

BACKGROUND

Soybeans (*Glycine max*), a major industrial use crop, are also one of the most important protein source crops and are considered a key food group for preventing disease and optimizing health by many public health organizations including the American Diabetes Association, the American Heart Association and the American Cancer Society. Asian soybean rust (ASR) is a major crop disease affecting soybeans and can negatively affect growth and yield. It is caused by the obligate biotrophic fungus *Phakopsora pachyrhizi* and, to a lesser extent, the closely related fungus *Phakopsora meibomiae*. The disease can cause yield losses ranging from 10-90%.

SUMMARY

The present disclosure relates to compositions and methods for identifying ASR resistance genes from legume species and transforming those genes into legume crops or a legume crop species, such as *Glycine max*, to generate plants that are resistant to ASR.

Disclosed herein are isolated polynucleotides comprising a nucleotide sequence that encodes one or more of the legume-derived, binary CcRpp2-R1 and CcRpp2-R3 polypeptides having at least 90% amino acid sequence identity to a legume sequence disclosed herein. In one embodiment the polynucleotide is a recombinant sequence comprising a heterologous promoter operably linked to a nucleotide sequence that encodes one or more of the legume-derived, binary CcRpp2-R1 and CcRpp2-R3 polypeptides. Soybean plants transformed with polynucleotides that express such binary polynucleotides have been demonstrated to display enhanced resistance to Asian soybean rust when compared to a susceptible plant and/or a non-transformed plant. Also disclosed are recombinant DNA constructs comprising the polynucleotides described herein, wherein the CcRpp2-R1 and CcRpp2-R3 coding sequences are operably linked to heterologous regulatory elements for expressing the CcRpp2-R1 and CcRpp2-R3 gene products in a plant cell.

Disclosed herein are useful polynucleotides which can comprise, or alternatively consist of or consist essentially of, a nucleic acid sequence of SEQ ID NOs: 1 or 3, and variants thereof. The polypeptides encoded thereby are capable of functioning as a binary polypeptide and are useful in compositions and methods for conferring resistance in a legume crop to ASR.

Disclosed herein are methods of conferring disease resistance in a legume crop species (e.g., soybean), the method comprising transforming a legume crop species with nucleic acid sequences that encode heterologous legume-derived binary CcRpp2-R1 and CcRpp2-R3 polynucleotides that confer disease resistance to a legume crop species disease (e.g., ASR).

In accordance with one embodiment a transgenic plant cell is provided wherein the plant cell comprises a recombinant polynucleotide that encodes a polypeptide that confers disease resistance to a legume crop species disease (e.g., ASR), wherein the encoded polypeptide has at least 65%, 75%, 85%, 90%, 95% or 99% sequence identity with an amino acid sequence selected from the group consisting of SEQ ID NOs: 2 and 21-36, and/or an amino acid sequence selected from the group consisting of SEQ ID NOs: 4 and 48-58.

Disclosed herein is a transgenic legume crop plant stably transformed with a recombinant DNA construct that comprises polynucleotides encoding one or more legume-derived CcRpp2-R1 and CcRpp2-R3 genes. In an aspect, the polynucleotide comprises one or more non-legume-derived CcRpp2-R1 and CcRpp2-R3 resistance genes and optionally additional non-CcRpp2-R1 and CcRpp2-R3 resistance genes that confer resistance to a plant disease. The polynucleotides described herein can also comprise any combination of resistance genes. The transgenic legume crop plant can comprise one or more input traits and/or agronomic traits. Obtaining the seeds from such transgenic legume crop plants is also contemplated. Further, the present disclosure also features a transgenic legume crop plant that is stably transformed that comprises the legume-derived binary CcRpp2-R1 and CcRpp2-R3 polynucleotides that have at least 90% or 95% sequence identity to a sequence described herein, including for example SEQ ID NOs 1, 3, 5-20 and 37-47.

Disclosed herein are methods of identifying one or more resistance genes conferring resistance to a plant disease (e.g., ASR). As disclosed herein are methods for detecting CcRpp2-R1 and CcRpp2-R3 resistance genes in a biological sample wherein said method comprises screening nucleic sequences recovered from the biological sample using primers or probes specific for the CcRpp2-R1 and CcRpp2-R3 resistance gene sequences, optionally wherein the primers and probes hybridize under stringent wash conditions to a nucleic acid sequence selected from SEQ ID NOs 1, 3, 5-20 and 37-47.

Disclosed herein are methods of producing an ASR resistant plant (e.g., a legume species) by introducing CcRpp2-R1 and CcRpp2-R3 resistance genes into a previous ASR susceptible plant lineage. In one embodiment, the method comprises transforming a plant cell with legume-derived binary CcRpp2-R1 and CcRpp2-R3 resistance genes. In one embodiment the method comprises transforming a plant cell with nucleic acid sequences comprising a sequence selected from the group consisting of SEQ ID NO: 1, SEQ ID NOs: 5-12 and 14-20 and SEQ ID NO: 13 and a sequence selected from the group consisting of SEQ ID NO: 3, SEQ ID NOs: 37-46 and SEQ ID NO: 47. The method can further comprise regenerating a transformed plant from the transformed plant cell. In an aspect, the method comprises growing the transformed plant such that the expression of the legume-derived CcRpp2-R1 and CcRpp2-R3 resistance gene produces a transformed plant that displays enhanced resistance to ASR disease.

In one embodiment, transgenic plants are produced that comprise either one of the CcRpp2-R1 and CcRpp2-R3 resistance genes. In this embodiment an plant exhibiting enhanced resistance to ASR is produced by crossing a first plant that comprises a CcRpp2-R1 gene with a second plant that comprises a CcRpp2-R3 gene and selecting ASR resistant progeny plants that comprise both the CcRpp2-R1 and CcRpp2-R3 resistance genes.

Disclosed herein are methods of producing a legume plant that is a progeny from a cross with a legume plant comprising legume-derived CcRpp2-R1 and CcRpp2-R3 binary resistance genes described herein, wherein progeny are selected that retain the CcRpp2-R1 and CcRpp2-R3 binary resistance genes.

Disclosed herein are methods of assaying a legume plant for disease resistance to a plant disease (e.g., ASR). In an aspect, the method comprises exposing a portion of the legume plant to a plant pathogen (e.g., *Phakopsora pachyrhizi*); measuring plant disease symptoms on the legume plant exposed to the plant pathogen; and comparing the plant disease symptoms to a reference standard for disease resistance.

Disclosed herein are methods of enhancing plant resistance to ASR disease. In an aspect, the method comprises conferring resistance to an ASR pathogen (e.g., *Phakopsora pachyrhizi*) by introgression of legume-derived CcRpp2-R1 and CcRpp2-R3 binary resistance genes into germplasm (e.g., a legume crop species) in a breeding program for resistance to ASR. The method features legume-derived CcRpp2-R1 and CcRpp2-R3 binary resistance genes that encode CcRpp2-R1 and CcRpp2-R3 polypeptides. In an aspect, the CcRpp2-R1 and CcRpp2-R3 polypeptides comprise an amino acid sequence having at least 90% homology to legume-derived CcRpp2-R1 and CcRpp2-R3 polypeptides disclosed herein. The method described herein also features a plant transformed with the polypeptide that displays enhanced resistance to ASR when compared to a susceptible plant.

BRIEF DESCRIPTION OF THE DRAWINGS

FIG. 1 is a schematic drawing of the Fine-mapping of CcRpp2 with reference *C. cajan scaffold* LGCc02. With gain and loss of function recombinant on the distal side (left) and 3 loss of function recombinants on the proximal side (right), the interval was delimited to 121,252 bp. Rd BAC library that was screened using the three markers located in this interval: Rdint_264620; dCAPS_393933 and Rdint_385686.

DETAILED DESCRIPTION

Definitions

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "plant" includes a whole plant and any descendant, cell, tissue, or part of a plant.

The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks. A harvestable part of a plant may be any useful part of a plant, including, for example and without limitation: flower; pollen; seedling; tuber; leaf; stem; fruit; seed; and root.

A plant cell is the structural and physiological unit of the plant. Plant cells, as used herein, includes protoplasts and protoplasts with a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant part" in embodiments herein.

The term "protoplast", as used herein, refers to a plant cell that had its cell wall completely or partially removed, with the lipid bilayer membrane thereof naked. Typically, a protoplast is an isolated plant cell without cell walls which has the potency for regeneration into cell culture or a whole plant.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

As used herein, "endogenous sequence" defines the native form of a polynucleotide, gene or polypeptide in its natural location in the organism or in the genome of an organism.

The term "exogenous sequence" as used herein is any nucleic acid sequence that has been introduced into a cell wherein at least a portion of the introduced nucleic acid sequence is not native to that host cell. For example, an exogenous DNA sequence may comprise a sequence from another species.

The term "heterologous sequence" as used herein is any nucleic acid sequence that has been removed from its native location and inserted into a new location altering the sequences that flank the nucleic acid sequence that has been moved. The heterologous sequence may be an exogenous sequence that originates from a foreign species or, if from the same species, is substantially modified from its native form in composition and/or genomic locus by deliberate human intervention. For example a heterologous promoter is a promoter sequence that has been operably linked to a coding sequence not natively linked to the promoter thus forming a recombinant nucleic acid sequence.

The term "isolated" as used herein means having been removed from its natural environment.

The term "purified", as used herein relates to the isolation of a molecule or compound in a form that is substantially free of contaminants normally associated with the molecule or compound in a native or natural environment and means having been increased in purity as a result of being separated from other components of the original composition. The term "purified nucleic acid" is used herein to describe a nucleic acid sequence which has been separated from other compounds including, but not limited to polypeptides, lipids and carbohydrates.

The terms "polypeptide", "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Complement" is used herein to refer to a nucleic acid sequence that is complementary to a given nucleic acid sequence such that it can hybridize to the given nucleic acid sequence to thereby form a stable duplex. In some embodiments, the nucleic acid sequence is fully complementary having 100% sequence identity.

"Polynucleotide sequence variants" is used herein to refer to a nucleic acid sequence that except for the degeneracy of the genetic code encodes the same polypeptide.

The term "sequence identity" or "identity," as used herein in the context of two nucleic acid or polypeptide sequences, refers to the residues in the two sequences that are the same when aligned for maximum correspondence over a specified comparison window.

As used herein, the term "percentage of sequence identity" refers to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988)

Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10. The National Center for Biotechnology Information (NCBI) Basic Local Alignment Search Tool (BLAST™; Altschul et al. (1990)) is available from several sources, including the National Center for Biotechnology Information (Bethesda, MD), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method. Those skilled in the art can determine appropriate parameters for aligning sequences, including any algorithms needed to achieve maximal alignment over the full length of the sequences being compared.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na+ and/or Mg++ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) Molecular Cloning: A Laboratory Manual, 2nd ed., vol. 1-3, Cold Spring Harbor Laboratory Press, Cold Spring Harbor, NY, 1989, chapters 9 and 11; and Hames and Higgins (eds.) Nucleic Acid Hybridization, IRL Press, Oxford, 1985. Further detailed instruction and guidance with regard to the hybridization of nucleic acids may be found, for example, in Tijssen, "Overview of principles of hybridization and the strategy of nucleic acid probe assays," in Laboratory Techniques in Biochemistry and Molecular Biology-Hybridization with Nucleic Acid Probes, Part I, Chapter 2, Elsevier, NY, 1993; and Ausubel et al., Eds., Current Protocols in Molecular Biology, Chapter 2, Greene Publishing and Wiley-Interscience, NY, 1995.

As used herein, "stringent conditions" encompass conditions under which hybridization will only occur if there is less than 20% mismatch between the hybridization molecule and a sequence within the target nucleic acid molecule. "Stringent conditions" include further particular levels of stringency. Thus, as used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize. The following are representative, non-limiting hybridization conditions.

High Stringency condition (detects sequences that share at least 90% sequence identity): Hybridization in 5×SSC buffer (wherein the SSC buffer contains a detergent such as SDS, and additional reagents like salmon sperm DNA, EDTA, etc.) at 65° C. for 16 hours; wash twice in 2×SSC buffer (wherein the SSC buffer contains a detergent such as SDS, and additional reagents like salmon sperm DNA, EDTA, etc.) at room temperature for 15 minutes each; and wash twice in 0.5×SSC buffer (wherein the SSC buffer contains a detergent such as SDS, and additional reagents like salmon sperm DNA, EDTA, etc.) at 65° C. for 20 minutes each.

Moderate Stringency condition (detects sequences that share at least 80% sequence identity): Hybridization in 5×-6×SSC buffer (wherein the SSC buffer contains a detergent such as SDS, and additional reagents like salmon sperm DNA, EDTA, etc.) at 65-70° C. for 16-20 hours; wash twice in 2×SSC buffer (wherein the SSC buffer contains a detergent such as SDS, and additional reagents like salmon sperm DNA, EDTA, etc.) at room temperature for 5-20 minutes each; and wash twice in 1×SSC buffer (wherein the SSC buffer contains a detergent such as SDS, and additional reagents like salmon sperm DNA, EDTA, etc.) at 55-70° C. for 30 minutes each.

Non-stringent control condition (sequences that share at least 50% sequence identity will hybridize): Hybridization in 6×SSC buffer (wherein the SSC buffer contains a detergent such as SDS, and additional reagents like salmon sperm DNA, EDTA, etc.) at room temperature to 55° C. for 16-20 hours; wash at least twice in 2×-3×SSC buffer (wherein the SSC buffer contains a detergent such as SDS, and additional reagents like salmon sperm DNA, EDTA, etc.) at room temperature to 55° C. for 20-30 minutes each.

Operably linked: A first nucleotide sequence is "operably linked" with a second nucleotide sequence when the first nucleotide sequence is in a functional relationship with the second nucleotide sequence. For instance, a promoter is operably linked to a coding sequence if the promoter affects the transcription or expression of the coding sequence. When recombinantly produced, operably linked nucleotide sequences are generally contiguous and, where necessary to join two protein-coding regions, in the same reading frame. However, nucleotide sequences need not be contiguous to be operably linked.

The term, "operably linked," when used in reference to a regulatory sequence and a coding sequence, means that the regulatory sequence affects the expression of the linked coding sequence. "Regulatory sequences," "regulatory elements", or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

When used in reference to two or more amino acid sequences, the term "operably linked" means that the first amino acid sequence is in a functional relationship with at least one of the additional amino acid sequences.

The term "resistance" is used herein to mean an absence or reduction of one or more disease symptoms in a plant caused by a plant pathogen. Resistance can mean that disease symptoms, such as, for example, number of lesions, defoliation, and associated yield loss, are reduced, minimized or lessened, when compared to a plant that is susceptible to the disease or a plant that does not contain an effective resistance gene, such as, for example, CcRpp2-R1 and CcRpp2-R3 genes that reduce one or more disease symptom. Further, resistance can include the prevention or delay of proliferation of a pathogen (e.g., fungi).

"Plant pathogen" or "fungal pathogen" can be used herein to mean fungal pathogens of, for example, the genus *Phakopsora,* including the species *Phakopsora pachyrhizi* and *Phakopsora meibomide.* These species are known to cause ASR in plants. A plant disease or a legume crop species disease, for example, can be ASR.

The term "disease resistance gene" or "resistance gene" is used herein to mean a gene that encodes a protein or polypeptide capable of enhancing or improving a defense or immune system response in a plant.

In the present disclosure, "nucleic acid" refers to a deoxy-ribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The term "encode" is used herein to mean that the nucleic acid comprises the required information, specified by the use of codons to direct translation of the nucleotide sequence (e.g., a legume sequence) into a specified protein. A nucleic acid encoding a protein can comprise non-translated sequences (e.g., introns) within translated regions of the nucleic acid or can lack such intervening non-translated sequences (e.g., as in cDNA).

Aspects of the disclosure encompass isolated or recombinant polynucleotide or protein compositions. An "isolated" or "recombinant" nucleic acid molecule (or DNA) is used herein to refer to a nucleic acid sequence (or DNA) that is no longer in its natural environment, for example in an in vitro or in a heterologous recombinant bacterial or plant host cell. An isolated or recombinant nucleic acid molecule, or biologically active portion thereof, is substantially free of other cellular material or culture medium when produced by recombinant techniques, or substantially free of chemical precursors or other chemicals when chemically synthesized.

The terms "inhibit," "inhibition," "inhibiting", "reduced", "reduction" and the like as used herein to mean any decrease in the expression or function of a target gene product, including any relative decrease in expression or function up to and including complete abrogation of expression or function of the target gene product.

The terms "increase," "increasing," "enhance," "enhancing" and the like are used herein to mean any boost or gain or rise in the expression, function or activity of a target gene (e.g., TIR gene) product providing an increased resistance to one or more pathogens (e.g., *Phakopsora* spp.) or to a disease (e.g., ASR) compared to a susceptible plant. Further, the terms "induce" or "increase" as used herein can mean higher expression of a target gene product, such that the level is increased 10% or more, 50% or more or 100% relative to a cell or plant lacking the target gene or protein of the present disclosure.

The term "expression" as used herein refers to the biosynthesis or process by which a polynucleotide, for example, is produced, including the transcription and/or translation of a gene product. For example, a polynucleotide of the present disclosure can be transcribed from a DNA template (such as into an mRNA or other RNA transcript) and/or the process by which a transcribed mRNA is subsequently translated into a polypeptide or protein.

The term "gene product" can refer to for example, transcripts and encoded polypeptides. Inhibition of (or increase in) expression or function of a gene product (i.e., a gene product of interest) can be in the context of a comparison between any two plants, for example, expression or function of a gene product in a genetically altered plant versus the expression or function of that gene product in a corresponding, but susceptible wild-type plant or other susceptible plant. The expression level of a gene product in a wild-type plant can be absent. For example, a "wild-type" plant can be a plant, plant cell or plant part that does not express an exogenous CcRpp2-R1 and/or CcRpp2-R3 nucleic acid or exogenous CcRpp2-R1 and/or CcRpp2-R3 protein.

Alternatively, inhibition of (or increase in) expression or function of the target gene product can be in the context of a comparison between plant cells, organelles, organs, tissues, or plant parts within the same plant or between plants, and includes comparisons between developmental or temporal stages within the same plant or between plants. Any method or composition that down-regulates expression of a target gene product, either at the level of transcription or translation, or down-regulates functional activity of the target gene product can be used to achieve inhibition of expression or function of the target gene product. Similarly, any method or composition that induces or up-regulates expression of a target gene product, either at the level of transcription or translation, or increases or activates or up-regulates functional activity of the target gene product can be used to achieve increased expression or function of the target gene or protein. Methods for inhibiting or enhancing gene expression are well known in the art.

The term "introducing" as used herein defines a process of altering the content of a cell/plant through the use of traditional breeding or recombinant transformation techniques. When using recombinant transformation techniques a nucleic acid or protein is passed across a plant cell membrane or cell wall into the interior of a plant cell. Methods for introducing polynucleotides into plants are known in the art, including procedures resulting in stable transformation methods or transient transformation methods. These include the use of calcium phosphate transfection, polybrene, protoplast fusion, PEG, electroporation, ultrasonic methods (e.g., sonoporation), liposomes, microinjection, naked DNA, plasmid vectors, viral vectors, both episomal and integrative, and any of the other well-known methods for introducing cloned genomic DNA, cDNA, synthetic DNA or other foreign genetic material into a host cell.

"Stable transformation" or "stably transformed" means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant.

The term "transformation" is used herein to mean the transfer of, for example, a nucleic acid fragment into the genome of a host organism, resulting in genetically stable inheritance. Host organisms containing the transformed nucleic acid fragments are referred to as "transgenic" organisms. The term "host cell" refers to the cell into which transformation of the recombinant DNA construct takes place and can include a yeast cell, a bacterial cell, and/or a plant cell. Examples of methods of plant transformation include Agrobacterium-mediated transformation and particle-bombardment. Transformed plant cells can then be used to regenerate a transformed plant by methods known to one skilled in the art.

The term "transgenic" is used herein to refer to a plant, including any part derived from a plant, such as a cell, tissue, or organ in which an exogenous nucleic acid (e.g., recombinant construct, vector or expression cassette including one or more nucleic acids) is integrated into the genome by a genetic engineering method, such as Agrobacteria transformation. By carrying out a gene technology method, the exogenous nucleic acid is stably integrated into a chromosome, so that successive generations may also be transgenic. As used herein, "transgenic" also encompasses biological processes including the crossing of plants and/or natural recombination.

EMBODIMENTS

Crop diseases cause serious crop management issues and can sometimes lead to total crop failure. Asian soybean rust is a threat to world soybean production and is currently addressed by the use of foliar fungicides. Stable and reliable genetic resistance in commercial plant lines is an important feature associated with soybean crop yields, and presently, commercially grown soybean cultivars that are fully resistant to Asian soybean rust caused by *Phakopsora pachyrhizi,* are not available. The causal agents of ASR, *Phakopsora pachyrhizi* and *Phakopsora meibomiae,* infect leaf tissue from a broad range of leguminous plants (at least 31 species in 17 genera; Slaminko et al. (2008) Plant Dis., 92:797-771 ; and at least 42 species in 19 genera; Frederick et al. (2002) Mycology, 92:217-227, respectively). In total, a further 152 species in other genera have been described to be potential hosts of *Phakopsora pachyrhizi* (Bonde et al. (2008) Plant Dis., 92:30-38; Goellner et al. (2010) Molecular Plant Pathology, 11 : 169-177; Ono et al. (1992) Mycol. Res., 96(10):825-850; and Slaminko et al. (2008) Plant Dis., 92:797-771). Currently, fungicide applications are the only commercially-available method to mitigate ASR. Besides fungicides, another management strategy can be used in South American countries such as Brazil for mitigating ASR. In particular, the use of short-cycle varieties planted at the beginning of the growing season (allowing crops to avoid disease favorable conditions) and host-free period, decreases the amount of primary inoculum.

Presently, no commercially grown soybean (*Glycine max*) cultivars are available that are fully resistant to *Phakopsora pachyrhizi.* Resistance to *Phakopsora pachyrhizi* in soybeans is rare; USDA evaluated the entire USA soybean germplasm collection and found that fewer than 5% were resistant or partially resistant to *Phakopsora pachyrhizi.* Furthermore, the genes available in these soybean accessions only provide resistance that is isolate-specific; therefore these sources are not able to provide durable resistance under field conditions such as where multiple races are present.

Given that ASR is a major threat to soybean production, it is beneficial to identify sources of resistance genes and incorporate these transgenic genes into legume germplasm, such as *Glycine max,* for enhanced protection. To identify novel resistance genes, several non-*Glycine max* legume species were screened for variation in resistance to *Phakopsora pachyrhizi.* Dominant resistance genes were identified and confirmed to be members of the TIR-TIR class of resistance (R) genes. When transferred to soybeans, the binary CcRpp2-R1 and CcRpp2-R3 resistance genes disclosed herein can provide resistance to *Phakopsora pachyrhizi* via heterologous expression.

Plants can defend themselves through a variety of cellular mechanisms. It is currently understood that the plant immune system is made up of receptors on the outside (often called the first tier immunity) and the inside of a cell (often referred to as the second tier immunity). Both sets of receptors can detect and respond to a pathogen. The first tier responds to primary elements of a pathogen resulting in activation of pathogen-associated molecular pattern (PAMP)-triggered immunity. Successful pathogens overcome PAMP-triggered immunity by secreting molecules called "effector proteins" or "effectors" that are either localized to the plant apoplast or are taken up into the plant cell. Effectors manipulate host cell functions to suppress host immune responses in order to facilitate the establishment of infection or to otherwise enhance growth conditions for the pathogen, e.g. by ensuring availability to nutrients. Plants have, in some cases, evolved a second tier of immunity in which R gene products recognize the activity of specific effectors resulting in an effector-triggered immunity. R genes typically encode proteins that feature C-terminal leucine-rich repeats (LRRs) and nucleotide-binding site (NBS) domains. Such nucleic acid binding LRRs are designated nucleotide-binding LRR (NLR) proteins. The NBS domain functions as a molecular switch depending on the bound nucleotide: ADP-bound in the resting state and ATP-bound in the active state. The LRR domain is generally thought to be involved in effector recognition and autoinhibition (Ting et al., Immunity, 28 (2008), pp. 285-287). Typical plant NLRs almost universally feature the additional coiled-coil (CC) or Toll/interleukin-1 receptor (TIR) N-terminal domain. These N-terminal domains are used to sort plant NLRs into two main groups termed CNLs (CC-NLRs) and TNLs (TIR-NLRs). Both CC and TIR domains have been demonstrated to play key roles in the formation of dimers and oligomers.

In plants, the TIR domain occurs at the N terminus of a major subclass of the (TIR-NLR) family resistance receptors (R proteins), which trigger defense responses after perception of pathogen effectors (Dodds and Rathjen, Nat Rev Genet. 2010;11:539-548). Recent findings indicate that TIR domain in R proteins functions as an NAD+-cleaving enzyme to trigger localized cell death, known as the hypersensitive response (HR). See: TIR-only protein regulates cell death in plants Proceedings of the National Academy of Sciences March 2017, 114 (10) E2053-E2062; DOI: 10.1073/pnas.1620973114 2) and TIR domains of plant immune receptors are NAD+-cleaving enzymes that promote cell death. SCIENCE 23 AUG 2019: 799-803. The LRR domain of plant R proteins appears to be the major determinant of recognition specificity. The NB domain is shared with mammalian nucleotide-binding oligomerization domain (NOD)-like receptors (NLRs), which also function as regulators of innate immune responses and apoptosis. Evidence suggests the NB domain can bind and hydrolyse nucleotides, and the presence of bound ATP or ADP may determine whether the R protein is in an active or inactive signaling state. However, in plant R proteins, the mechanism by which effector recognition is linked to the activation of defense signaling is poorly understood.

As a result of the "arms race" between host and pathogen, pathogen effectors can have either an avirulence or virulence effect. The virulence activity of effectors is associated with the manipulation of normal host cell functions or the suppression of host immune responses by the pathogen in order to establish successful infection. In avirulence, recognition by the corresponding plant R protein activates a host immune or defense response, resulting in programmed cell death and resistance to the pathogen.

The nucleic acids and polypeptides disclosed herein are useful in generating transgenic plants exhibiting fungal resistance and in methods for conferring or enhancing or increasing fungal resistance to a plant (e.g., a legume crop species). Methods and compositions disclosed herein may comprise the following polypeptide and polynucleotides sequences:

SEQ ID NO: 1 CcRpp2-R1Aa coding sequence from *Cajanus cajan* (polynucleotide sequence).

SEQ ID NO: 2: CcRpp2-R1Aa (polypeptide sequence).

SEQ ID NO: 3: CcRpp2-R3Aa coding sequence from *Cajanus cajan* (polynucleotide sequence).

SEQ ID NO: 4: CcRpp2-R3Aa (polypeptide sequence).

In another embodiment the CcRpp2-R1 polynucleotides of SEQ ID NOs: 5-20 and the CcRpp2-R3 polynucleotides of SEQ ID NOs: 37-47, and the respective CcRpp2-R1 polypeptides of SEQ ID NOs: 21-36 and CcRpp2-R3 polypeptides of SEQ ID NOs: 48-58 disclosed herein are useful in generating transgenic plants exhibiting fungal resistance and in methods for conferring or enhancing or increasing fungal resistance to a plant (e.g., a legume crop species).

In some embodiments, a CcRpp2-R1 polypeptide is provided that has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to any one of SEQ ID NOs: 2 and 21-36, as well as amino acid substitutions, deletions, insertions, fragments thereof, and combinations thereof.

In some embodiments, the CcRpp2-R3 polypeptide is provided that has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to any one of SEQ ID NOs: 4 and 48-58, as well as amino acid substitutions, deletions, insertions, fragments thereof, and combinations thereof.

Polypeptides of the present disclosure can be produced either from a nucleic acid disclosed herein, or by the use of standard molecular biology techniques. For example, a CcRpp2-R1 and/or CcRpp2-R3 protein of the present disclosure can be produced by expression of a recombinant nucleic acid of the embodiments in an appropriate host cell, or alternatively by a combination of ex vivo procedures.

Compositions and methods disclosed herein are useful in protecting plants from fungal pathogens. The interactions between a host and a pathogen can be described in a continuum of "immunity" to "susceptibility." The terms "immunity" or "immune" are used herein to mean the absence of any macroscopically visible disease symptom(s). The term " resistance" is used herein to mean the presence of macroscopically visible lesions with no or limited sporulation, and/or a reduction in the extent or degree and/or a delay in the progression of any disease symptom(s) and can be, for example, manifested as reduced number of lesions or lesions with a reduction in sporulation. As used herein, the term "susceptibility" or the phrase "lack of resistance" to ASR refers to the occurrence of lesions with sporulation levels equal to or above the sporulation level observed in a reference standard, such as, for example, cultivars Williams or Peking.

Methods of the present disclosure can be carried out, for example, to provide enhanced resistance by *Glycine max* to the obligate biotrophic fungus *Phakopsora pachyrhizi,* the main causal agent of ASR, or to *Phakopsora meibomiae.* For example, increased or enhanced resistance to a fungal pathogen may be compared to the response of a susceptible plant, such as, for example, Williams or Peking. Resistance can vary and is related to the proportion (i.e., percent) of disease symptoms (e.g., lesions) observed on a plant or plant part (e.g., leaf). A numerical score or value for immunity, resistance and susceptibility can be given. For example, a numerical score for resistance represents the degree of resistance a plant exhibits to a plant disease (e.g., ASR). The numerical scores can also be used to compare the degree of resistance, for example, between a plant of interest (e.g., a transgenic legume crop plant) to that of a susceptible plant (e.g., Williams or Peking) or a reference standard.

Methods and compositions for resistance disclosed herein relate to the isolation of one or more resistance genes from a legume species, and the subsequent transfer of one or more of these resistance genes to another plant, soybeans, for example, to provide resistance to *Phakopsora* spp. via homologous or heterologous expression. An aspect of the present disclosure comprises the transfer of functioning TIR genes to a sexually compatible or incompatible species to produce disease resistance. Polypeptides and TIR genes (e.g., CcRpp2-R1 and CcRpp2-R3 polypeptides and CcRpp2-R1 and CcRpp2-R3 genes) described herein can be used alone or in a stack with other resistance genes such as R genes (including NB-LRR resistance genes) or in a stack with non-R genes (including non-NB-LRR resistance genes) to provide resistance to ASR.

The transgenic approach of the present disclosure therefore can be used alone or in combination with other strategies to produce or confer ASR resistance in plants. Other useful strategies include, but are not limited to, blocking the functional activity of effectors, inhibiting the uptake of a pathogen or pathogen factors (e.g., fungi) into the host cell (e.g., plant cell) and/or conventional breeding for resistance.

In one embodiment, the transgenic approach of the present disclosure may be used in combination with the transgenic expression of a CcRpp1 polynucleotide (for example SEQ ID NO: 59) and the polypeptide encoded thereby (SEQ ID NO: 60) (See also the NB-LRR2 polynucleotide and the polypeptide encoded thereby as disclosed in U.S. Patent Application Publication No. US2018-0103600, incorporated herein by reference in its entirety). Such approach may be by way of either a breeding stack or a molecular stack containing a CcRpp1 gene and a binary of the CcRpp2-R1 and CcRpp2-R3 genes disclosed herein.

Methods of the present disclosure can provide or enhance the resistance of a plant, such that the causal agents of a disease, such as ASR, can no longer reproduce. The term "enhance" means to improve, increase, amplify, multiply, elevate and/or raise, thereby reducing one or more disease symptoms. Accordingly, plants (e.g., soybean) exhibit an increased resistance to a disease (e.g., ASR) when compared to plants that are susceptible or tolerant to *Phakopsora* spp. In an aspect, methods described herein can reduce one or more symptoms (i.e., disease symptoms) of a legume plant disease (e.g., ASR). A method can comprise exposing a transgenic legume crop plant (e.g., soybean) to a legume plant disease resulting in the transgenic legume crop plant having enhanced resistance to the plant disease. In some aspects, the transgenic legume crop plant comprises a CcRpp2-R1 and CcRpp2-R3 polynucleotide. One or more legume-derived CcRpp2-R1 and CcRpp2-R3 polynucleotides may have at least 90% sequence identity to a sequence as disclosed herein.

In an aspect, the plant, plant part, or plant cell is derived from a plant including but not limited to, alfalfa, clover, peas, beans, lentils, lupins, mesquite, carob, soybeans, peanuts, and tamarind. Progeny, variants, and mutants of disease resistant plants disclosed herein are within the scope of the present disclosure, provided that these progeny, variants, and mutants comprise the original/modified polynucleotides of the parent plant.

In one embodiment, the plant is a legume. In another embodiment, the CcRpp2-R1 and CcRpp2-R3 polypeptides, CcRpp2-R1 and CcRpp2-R3 polynucleotides, and/or CcRpp2-R1 and CcRpp2-R3 resistance genes are derived from a legume. Examples of legumes include, but are not limited to, the genus *Phaseolus* (e.g., French bean, dwarf bean, climbing bean (*Phaseolus vulgaris*), Lima bean (*Phaseolus lunatus*), Tepary bean (*Phaseolus acutifolius*), runner bean (*Phaseolus coccineus*)); the genus *Glycine* (e.g., *Glycine soja,* soybeans (*Glycine max* (L.))); pea (*Pisum*) (e.g., shelling peas (sometime called smooth or roundseeded peas; *Pisum sativum*); marrowfat pea (*Pisum sativum*), sugar pea (*Pisum sativum*), also called snow pea, edible-podded pea or mangetout, (*Pisum granda*)); peanut (*Arachis hypogaea*), clover (*Trifolium* spp.), medick (*Medicago*), kudzu vine (*Pueraria lobata*), common lucerne, alfalfa (*Medicago sativa*), chickpea (*Cicer*), lentils (*Lens culinaris*), lupins (*Lupinus*); vetches (*Vicia*), field bean, broad bean (*Vicia faba*), vetchling (*Lathyrus*) (e.g., chickling pea (*Lathyrus sativus*), heath pea (*Lathyrus tuberosus*)); genus *Vigna* (e.g., moth bean (*Vigna aconiti folia*), adzuki bean (*Vigna angularis*), urd bean (*Vigna mungo*), mung bean (*Vigna radiata*), bambara groundnut (*Vigna subterrane*), rice bean (*Vigna umbellata*), *Vigna vexillata, Vigna unguiculata* (also known as asparagus bean, cowpea)); pigeon pea (*Cajanus cajari; Cajanus cajan*), the genus *Macrotyloma* (e.g., geocarpa groundnut (*Macrotyloma geocarpum*), horse bean (*Macrotyloma uniflorum;* goa bean (*Psophocarpus tetragonolobus,* African yam bean (*Sphenostylis stenocarpa*), Egyptian black bean, lablab bean (*Lablab purpureus*), yam bean (*Pachyrhizus erosus*), guar bean (*Cyamopsis tetragonolobus*); and/or the genus *Canavalia* (e.g., jack bean (*Canavalia ensiformis*)), sword bean (*Canavalia gladiata*).

Compositions and methods described herein can result in an agronomically desirable line or variety. Agronomic characteristics or traits include, but are not limited to, herbicide tolerance, increased yield, insect control, weed control, pest control, pathogen disease resistance (e.g., fungal, virus, bacterial), high protein production, germination and seedling growth control, enhanced nutrition, environmental stress resistance, increased digestibility, male sterility, flowering time, or transformation technology traits such as cell cycle regulation and/or gene targeting.

The present disclosure provides a method for screening or assaying legume plants for resistance, immunity, or susceptibility to a plant disease. General methods for determination of resistance, immunity, or susceptibility of a plant to a particular pathogen are known to one skilled in the art. For example, a method for screening or assaying legume plants for resistance, immunity or susceptibility to a plant disease may comprise exposing a plant cell, tissue or organ (e.g., leaf) to a pathogen (e.g., *Phakopsora pachyrhizi*) and then determining and/or measuring in the exposed plant, the degree of resistance, immunity and/or susceptibility to a plant disease (e.g., ASR) caused by the pathogen. The method can further comprise measuring any observable plant disease symptoms on the plant exposed to the plant pathogen and then comparing the plant disease symptoms to a reference standard to determine the degree or extent of disease resistance.

Methods of exposing a plant cell, tissue or organ to a pathogen are known in the art. Methods of measuring, comparing, and determining the level of resistance, immunity and/or susceptibility (e.g., plant disease symptoms) to a disease, such as, for example, ASR, caused by the pathogen are also known in the art. The exposed plants can be further assessed to isolate polynucleotides, amino acid sequences and/or genetic markers that are associated with, linked to, and/or confer resistance, immunity or susceptibility of a plant to a particular pathogen or disease. Further assessments include, but are not limited to, isolating polynucleotides, nucleic acids, or amino acids sequences from the exposed plant, carrying out an assay of the isolated polynucleotides or nucleic acids, for example, to detect one or more biological or molecular markers associated with one or more agronomic characteristics or traits, including but not limited to, resistance, immunity and/or susceptibility. The information gleaned from such methods can be used, for example, in a breeding program.

In one embodiment an isolated or recombinant nucleic acid is provided that is free of sequences (optimally protein encoding sequences) that naturally flank the nucleic acid (i.e., sequences located at the 5' and 3' ends of the nucleic acid) in the genomic DNA of the organism from which the nucleic acid is derived. For example, in some embodiments of the disclosure, the isolated polynucleotide sequence encoding the resistance proteins disclosed herein can contain less than about 5 kb, about 4 kb, about 3 kb, about 2 kb, about 1 kb, about 0.5 kb, or about 0.1 kb of nucleotide sequence that naturally flank the polynucleotide in genomic DNA of the cell from which the polynucleotide is derived. A protein that is substantially free of cellular material includes preparations of protein having less than about 30%, about 20%, about 10%, about 5%, or about 1% (by dry weight) of contaminating protein. When the protein of the embodiments, or a biologically active portion thereof, is recombinantly produced, optimally culture medium represents less than about 30%, about 20%, about 10%, about 5%, or about 1% (by dry weight) of chemical precursors or non-protein-of-interest chemicals.

Fragments and variants relating to the nucleotide sequences and proteins encoded are within the scope of the present disclosure. A "fragment" refers to a portion of the nucleotide sequence or a portion of the amino acid sequence and thus the protein encoded thereby. Fragments of a nucleotide sequence can encode protein fragments that retain the biological activity of the native protein and have the ability to confer resistance (i.e., fungal resistance) upon a plant. Alternatively, fragments of a nucleotide sequence, that are useful as hybridization probes, do not necessarily encode fragment proteins retaining biological activity. Thus, fragments of a nucleotide sequence can range from at least about 15 nucleotides, about 50 nucleotides, about 100 nucleotides, and up to the full-length nucleotide sequence encoding the polypeptides of the present disclosure. "Functional fragment," "fragment that is functionally equivalent," and "functionally equivalent fragment" are used interchangeably herein. These terms refer to a portion or subsequence of a polypeptide sequence of the present disclosure in which its native ability is retained.

A fragment of a nucleotide sequence that encodes a biologically active portion of a polypeptide of the present disclosure can encode at least about 15, about 25, about 30, about 40, or 45 to about 50 contiguous amino acids, or up to the total number of amino acids present in a full-length polypeptide of the embodiments (for example, 341 amino acids for the peptide encoded by SEQ ID NO: 2).

Fragments of a nucleotide sequence that are useful as hybridization probes or PCR primers generally need not encode a biologically active portion of a protein.

In some embodiments, the CcRpp2-R1 polypeptide fragment is an N-terminal truncation of at least 1, 2, 3, 4, 5, 6, 7, 8, 9, 10, 11, 12, 13, 14, 15, 16, 17, 18, 19, 20, 21, 22, 23, 24 or more amino acids from the N-terminus of CcRpp2-R1 polypeptides of SEQ ID NOs: 2 and 21-36.

In some embodiments, the CcRpp2-R3 polypeptide fragment is an N-terminal truncation of at least 1, 2, 3, 4, 5, 6, 7, 8, 9, 10, 11, 12, 13, 14, 15, 16, 17, 18, 19, 20, 21, 22, 23, 24 or more amino acids from the N-terminus of CcRpp2-R3 polypeptides of SEQ ID NOs: 4 and 48-58.

In some embodiments, the CcRpp2-R1 polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or more amino acids from the N-terminus and/or C-terminus relative to CcRpp2-R1 polypeptides of SEQ ID NOs: 2 and 21-36.

In some embodiments, the CcRpp2-R3 polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or more amino acids from the N-terminus and/or C-terminus relative to CcRpp2-R3 polypeptides of SEQ ID NOs: 4 and 48-58.

In some embodiments, a CcRpp2-R1 polypeptide comprises an amino acid sequence having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of any one of the CcRpp2-R1 polypeptides of SEQ ID NOs: 2 and 21-36, wherein the CcRpp2-R1 polypeptide has fungal resistance activity.

In some embodiments, a CcRpp2-R3 polypeptide comprises an amino acid sequence having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of any one of the CcRpp2-R3 polypeptides of SEQ ID NOs: 4 and 48-58, wherein the CcRpp2-R3 polypeptide has fungal resistance activity.

In some embodiments, a CcRpp2-R1 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of any one of the CcRpp2-R1 polypeptides of SEQ ID NOs: 2 and 21-36.

In some embodiments, a CcRpp2-R3 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of any one of the CcRpp2-R3 polypeptides of SEQ ID NOs: 4 and 48-58.

In some embodiments, the polypeptide fragment is an N-terminal and/or a C-terminal truncation of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more amino acids from the N-terminus and/or C-terminus, by proteolysis, by insertion of a start codon, by deletion of the codons encoding the deleted amino acids and concomitant insertion of a start codon, and/or insertion of a stop codon.

The term "full-length sequence," when referring to a specified polynucleotide, means having the entire nucleic acid sequence of a native sequence. In one embodiment fragments of the polynucleotide sequences disclosed herein, including SEQ ID NOs: 1 and 3 are provided. Such fragments can be used as hybridization probes or PCR primers, and do not necessarily encode fragment proteins retaining biological activity. Thus, fragments of a nucleotide sequence can range from at least about 15 nucleotides, about 50 nucleotides, about 100 nucleotides, and up to the full-length nucleotide sequence encoding the polypeptides of the present disclosure.

In accordance with one embodiment a method of identifying plants comprising a CcRpp2-R1 and/or CcRpp2-R3 gene of the disclosure is provided. The method comprises obtaining a nucleic acid sample from one or more plants, and contacting said nucleic acid sample with a nucleic acid sequence that specifically binds to a CcRpp2-R1 and/or CcRpp2-R3 gene of the disclosure, and detecting the specific binding of the nucleic acid to its target sequence. For example, the method can detect the target sequence through the use of a labeled probe or by conducting a PCR reaction with suitable PCR primers that only produce an amplicon in the presence of the target sequence. In one embodiment the method comprises obtaining a nucleic acid sample from one or more plants, and contacting the nucleic acid sample with either i) a polynucleotide that comprises a sequence of at least 8 nucleotides that are identical or have at least 90-95% sequence identity to a contiguous sequence selected from the group consisting of SEQ ID NOs: 1, 3, 5-20 and 37-47, or complements thereof; wherein said method further comprises subjecting said sample and said polynucleotide to stringent hybridization conditions; and assaying said sample for hybridization of said polynucleotide to said DNA; or ii) a pair of PCR primers, wherein a first and second PCR primer each specifically bind to a sequence selected from the group consisting of SEQ ID NOs: 1, 3, 5-20 and 37-47, wherein said first and second PCR primers are capable of producing an amplicon when bound to their target complementary sequences and subjected to standard PCR reaction conditions; subjecting said sample to polymerase chain reaction conditions; and assaying for an amplicon generated between said first and second primers.

In some embodiments, fusion proteins are provide comprising a CcRpp2-R1 polypeptide and/or CcRpp2-R3 polypeptide of the disclosure represented by a formula selected from the group consisting of:

R1-L-R2, R2-L-R1, R1-R2 or R2-R1 wherein RI is a CcRpp2-R1 polypeptide, chimeric CcRpp2-R1 polypeptide of the disclosure, or a protein of interest and R2 is a CcRpp2-R3 polypeptide, chimeric CcRpp2-R3 polypeptide of the disclosure, or a protein of interest. The R1 polypeptide is fused either directly or through a linker (L) segment to the R2 polypeptide. The term "directly" defines fusions in which the polypeptides are joined without a peptide linker. Thus "L" represents a chemical bound or polypeptide segment to which both R1 and R2 are fused in frame, most commonly L is a linear peptide to which R1 and R2 are bound by amide bonds linking the carboxy terminus of R1 to the amino terminus of L and carboxy terminus of L to the amino terminus of R2. By "fused in frame" is meant that there is no translation termination or disruption between the reading frames of R1 and R2. The linking group (L) is generally a polypeptide of between 1 and 500 amino acids in length.

A fragment of a nucleotide sequence of the present disclosure can encode a biologically active portion of a polypeptide, or it can be a fragment that can be used as a hybridization probe or PCR primer using methods disclosed below. A biologically active portion of a polypeptide conferring resistance can be prepared by isolating a portion of one of the nucleotide sequences of the embodiments, expressing the encoded portion of the protein and assessing the ability of the encoded portion of the protein to confer or enhance fungal resistance in a plant. Nucleic acid molecules that are fragments of a nucleotide sequence of the embodiments comprise at least about 15, about 20, about 50, about 75, about 100, or about 150 nucleotides, or up to one less than the total number of nucleotides present in a full-length nucleotide sequence disclosed herein (for example, 5210 nucleotides for SEQ ID NO: 8).

One source of polynucleotides that encode CcRpp2-R1 and/or CcRpp2-R3 polypeptides or related proteins is a species selected from, but not limited to, *Arachis, Cercis, Cajanus, Glycine, Medicago, Phaseolus, Pisum* or *Vigna* species, which contains a homologous CcRpp2-R1 polynucleotide or CcRpp2-R3 polynucleotide.

The polynucleotides of SEQ ID NOs: 1 and 5-20 and 3 and 37-47 can be used to express CcRpp2-R1 and CcRpp2-R3 polypeptides, respectively, in legume host plants that include but are not limited to alfalfa, clover, pea, bean lentil, lupin, mesquite, carob, soybean, peanut or tamarind.

The polynucleotides are also useful as probes for isolating homologous or substantially homologous polynucleotides that encode CcRpp2-R1 and CcRpp2-R3 polypeptides or related proteins. Such probes can be used to identify homologous or substantially homologous polynucleotides derived from species selected from, but not limited to, *Arachis, Cercis, Cajanus, Glycine, Medicago, Phaseolus, Pisum* or *Vigna*.

Polynucleotides that encode CcRpp2-R1 and CcRpp2-R3 polypeptides can also be synthesized de novo from a CcRpp2-R1 or CcRpp2-R3 polypeptide sequence. The sequence of the polynucleotide gene can be deduced from a CcRpp2-R1 or CcRpp2-R3 polypeptide sequence through use of the genetic code. Computer programs such as "Back-Translate" (GCG™ Package, Acclerys, Inc. San Diego, Calif.) can be used to convert a peptide sequence to the corresponding nucleotide sequence encoding the peptide. Examples of CcRpp2-R1 or CcRpp2-R3 polypeptide sequences that can be used to obtain corresponding nucleotide encoding sequences include, but are not limited to the CcRpp2-R1 or CcRpp2-R3 polypeptides of SEQ ID NOs: 2, 4, 21-36 and 48-58.

In some embodiments, the nucleic acid molecule encoding a CcRpp2-R1 or CcRpp2-R3 polypeptide is a polynucleotide having the sequence set forth in one of SEQ ID NOs:

1, 3, 5-20 and 37-47, and variants, fragments and complements thereof. Nucleic acid sequences that are complementary to a nucleic acid sequence of the embodiments or that hybridize to a sequence of the embodiments are also encompassed. The nucleic acid sequences can be used in DNA constructs or expression cassettes for transformation and expression in organisms, including microorganisms and plants. The nucleotide or amino acid sequences may be synthetic sequences that have been designed for expression in an organism including, but not limited to, a plant.

In some embodiments, the nucleic acid molecule encoding a CcRpp2-R1 or CcRpp2-R3 polypeptide is a non-genomic nucleic acid sequence.

In some embodiments, the nucleic acid molecule encoding a CcRpp2-R1 or CcRpp2-R3 polypeptide is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to any one of the nucleic acid sequences of SEQ ID NOs: 1, 3, 5-20 and 37-47, wherein the encoded CcRpp2-R1 or CcRpp2-R3 polypeptide has fungal resistance activity.

In some embodiments, the CcRpp2-R1 polynucleotide encodes a CcRpp2-R1 polypeptide having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to any one of SEQ ID NOs: 2 and 21-36, and has at least one amino acid substitution, deletion, insertion or combination therefore, compared to the native sequence.

In some embodiments, the CcRpp2-R3 polynucleotide encodes a CcRpp2-R3 polypeptide having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to any one of SEQ ID NOs: 4 and 48-58, and has at least one amino acid substitution, deletion, insertion or combination therefore, compared to the native sequence.

In some embodiments, the nucleic acid molecule encodes a CcRpp2-R1 polypeptide comprising an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of any one of the amino acid sequences of SEQ ID NOs: 2 and 21-36.

In some embodiments, the nucleic acid molecule encodes a CcRpp2-R3 polypeptide comprising an amino acid sequence having at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of any one of the amino acid sequences of SEQ ID NOs: 4 and 48-58.

In some embodiments, the nucleic acid molecule encodes a CcRpp2-R1 polypeptide comprising an amino acid sequence of any one of SEQ ID NOs: 2 and 21-36 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35 or more amino acid substitutions, deletions and/or insertions compared to the amino acid at the corresponding position of the respective SEQ ID NO: 2 and 21-36.

In some embodiments, the nucleic acid molecule encodes a CcRpp2-R3 polypeptide comprising an amino acid sequence of any one of SEQ ID NOs: 4 and 48-58 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35 or more amino acid substitutions, deletions and/or insertions compared to the amino acid at the corresponding position of the respective SEQ ID NO: 4 and 48-58.

The polynucleotide coding sequences can be modified to add a codon at the position following the methionine start codon to create a restriction enzyme site for recombinant cloning purposes and/or for expression purposes. In some embodiments, the CcRpp2-R1 and/or CcRpp2-R3 polypeptide further comprises an alanine residue at the position after the translation initiator methionine.

"Variant" is intended to mean a protein or polypeptide derived from a native protein or polypeptide by deletion or addition of one or more amino acids at one or more internal sites in the native protein or polypeptide and/or substitution of one or more amino acids at one or more sites in a native protein or polypeptide. Variants encompassed by the present disclosure exhibit a biological activity of the native protein or polypeptide sequence. For polynucleotides, a variant comprises a polynucleotide having a deletion (i.e., truncations) at the 5' and/or 3' end and/or a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. One of skill in the art can recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Naturally occurring allelic variants such as these can be identified with the use of well-known molecular biology techniques, as, for example, with polymerase chain reaction (PCR) and hybridization techniques as outline below. Variant polynucleotides also include synthetically derived polynucleotides, such as those generated, for example, by using site-directed mutagenesis but which still encode a protein of the embodiments. Generally, variants of a particular polynucleotide of the present disclosure can have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs known in the art.

Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs known in the art. Where any given pair of polynucleotides of the present disclosure is evaluated by comparison of the percent sequence identity shared by the two polypeptides they encode, wherein the percent sequence identity between the two encoded polypeptides is at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity.

"Variant protein" means a protein derived from the native protein by deletion or addition of one or more amino acids at one or more sites in the native protein and/or substitution of one or more amino acids at one or more sites in the native protein. Variant proteins encompassed by some aspects of the present disclosure are biologically active, that is they continue to possess the desired biological activity of the native protein, which is, the ability to confer or enhance plant resistance (i.e., plant fungal pathogen resistance) as described herein. Such variants can result, for example, from genetic polymorphism or from human manipulation. Biologically active variants of a native protein of the embodiments can have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the amino acid sequence for the native protein as determined by sequence alignment programs known in the art. A biologically active variant of a protein of the present disclosure can differ from that protein by as few as about 1-15 amino acid residues, as few as about 1-10, such as about 6-10, as few as about 5, as few as 4, 3, 2, or even 1 amino acid residue.

The proteins disclosed herein can be altered, for example, by including amino acid substitutions, deletions, truncations, and insertions. Methods for such manipulations are known in the art. For example, amino acid sequence variants and fragments of the resistance proteins can be prepared by mutations in the DNA. Methods for mutagenesis and poly-nucleotide alterations are known in the art.

Variant polynucleotides and proteins also encompass sequences and proteins derived from mutagenic or recombi-nogenic procedures, including and not limited to procedures such as DNA shuffling. Libraries of recombinant polynucle-otides can be generated from a population of related sequence polynucleotides comprising sequence regions that have substantial sequence identity and can be homologously recombined in vitro or in vivo. For example, using this approach, sequence motifs encoding a domain of interest can be shuffled between the protein gene of the present disclosure and other known protein genes to obtain a new gene coding for a protein with an improved property of interest, such as increased ability to confer or enhance plant resistance to a fungal pathogen. Strategies for such DNA shuffling are known in the art.

Variants may be made by making random mutations or the variants may be designed. In the case of designed mutants, there is a high probability of generating variants with similar activity to the native polypeptide when amino acid identity is maintained in critical regions of the polypeptide which account for biological activity or are involved in the deter-mination of three-dimensional configuration which ulti-mately is responsible for the biological activity. A high probability of retaining activity will also occur if substitu-tions are conservative. Amino acids may be placed in the following classes: non-polar, uncharged polar, basic, and acidic. Conservative substitutions whereby an amino acid of one class is replaced with another amino acid of the same type are least likely to materially alter the biological activity of the variant. Table 1 provides a listing of examples of amino acids belonging to each class.

TABLE 1

| Classes of amino acids | |
| --- | --- |
| Class of Amino Acid | Examples of Amino Acids |
| Nonpolar Side Chains | Ala (A), Val (V), Leu (L), Ile (I), Pro (P), Met (M), Phe (F), Trp (W) |
| Uncharged Polar Side Chains | Gly (G), Ser (S), Thr (T), Cys (C), Tyr (Y), Asn (N), Gln (Q) |
| Acidic Side Chains | Asp (D), Glu (E) |
| Basic Side Chains | Lys (K), Arg (R), His (H) |
| Beta-branched Side Chains | Thr, Val, Ile |
| Aromatic Side Chains | Tyr, Phe, Trp, His |

The polynucleotides described herewith can be used to isolate corresponding sequences from other organisms, par-ticularly other plants. In this manner, methods such as PCR or hybridization can be used to identify such sequences based on their sequence identity to the sequences set forth herein. Sequences isolated based on their sequence identity to the entire sequences set forth herein or to variants and fragments thereof are encompassed by the present disclo-sure. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share at least about 60%, about 70%, about 75%, about 80%, about 85%, about 90%, about 91%, about 92%, about 93%, about 94%, about 95%, about 96%, about 97%, about 98%, about 99%, or greater sequence identity. Func-tions of orthologs are often highly conserved among species. Thus, isolated polynucleotides that encode for a protein that confers or enhances fungal plant pathogen resistance and that hybridize to the sequences disclosed herein, or to variants or fragments thereof, are encompassed by the present disclosure.

In a PCR approach, oligonucleotide primers can be designed for use in PCR reactions to amplify corresponding DNA sequences from cDNA or genomic DNA extracted from any organism of interest. Methods for designing PCR primers and PCR cloning are known in the art and are disclosed in Sambrook et al. (1989) Molecular Cloning: A Laboratory Manual (2d ed., Cold Spring Harbor Laboratory Press, Plainview, N.Y.). Known methods of PCR include, and are not limited to, methods using paired primers, nested primers, single specific primers, degenerate primers, gene-specific primers, vector-specific primers, partially-mis-matched primers, and the like.

In hybridization techniques, all or part of a known poly-nucleotide is used as a probe that selectively hybridizes to other corresponding polynucleotides present in a population of cloned genomic DNA fragments or cDNA fragments (i.e., genomic or cDNA libraries) from a chosen organism. The hybridization probes can be genomic DNA fragments, cDNA fragments, RNA fragments, or other oligonucle-otides, and can be labeled with a detectable group such as $^{32}P$, or any other detectable marker. Thus, for example, probes for hybridization can be made by labeling synthetic oligonucleotides based on the polynucleotides of the embodiments. Methods for preparation of probes for hybrid-ization and for construction of cDNA and genomic libraries are known in the art.

Various procedures can be used to check for the presence or absence of a particular sequence of DNA, RNA, or a protein. These include, for example, Southern blots, northern blots, western blots, and ELISA analysis. These techniques are well known in the art.

The compositions and methods of the present disclosure are useful for modulating the levels of one or more proteins in a plant. The term "modulate" is used herein to mean an increase or decrease in the level of a protein within a genetically altered (i.e., transformed) plant relative to the level of that protein from the corresponding non-transformed plant (i.e., a plant not genetically altered in accordance with the methods of the present disclosure).

The genes and polynucleotides of the present disclosure include naturally occurring sequences as well as mutant or altered forms. The proteins disclosed herein also encompass naturally occurring proteins as well as variations, fragments and modified forms thereof. Such variants and fragments will continue to possess the desired ability to confer or enhance plant fungal pathogen resistance. In an aspect, mutations made in the DNA encoding the variant or fragments thereof generally do not place the sequence out of the reading frame and optimally will not create complementary regions that could produce secondary mRNA structure.

The gene or genes of the present disclosure can be expressed as a transgene in order to make plants resistant to ASR. The use of different promoters described herein or known to those of skill in the art will allow the gene's expression to be modulated in different circumstances (i.e., the promoters can be selected based on the desired outcome). For instance, higher levels of expression in a particular tissue system or organ (e.g., leaves) may be desired to enhance resistance. The entire gene can be inserted (e.g., both native promoter and coding sequence), as a transgene, permitting quick combination with other traits, such as insect or herbicide resistance.

In accordance with one embodiment a polynucleotide encoding a polypeptide having at least 85%, 90%, 95% or 99% sequence identity with a sequence selected from the group consisting of SEQ ID NOs: 2, 4, 21-36 and 48-58 is provided, wherein the polypeptide when expressed in the cells of a plant confers resistance to Asian Soybean Rust (ASR) disease for said plant. In a further embodiment the polynucleotide is selected from the group consisting of SEQ ID NOs: 1, 3, 5-20 and 37-47 or a polynucleotide having at least 85%, 90%, 95% or 99% sequence identity to SEQ ID NOs: 1, 3, 5-20 and 37-47. In one embodiment these polynucleotide sequences can be operably linked to heterologous regulatory elements necessary for expressing the encoded CcRpp2-R1 and CcRpp2-R3 gene products in a plant cell. For example, the regulatory elements can include promoters; translation leader sequences; enhancers; termination sequences; and polyadenylation recognition sequences. In one embodiment a recombinant polynucleotide is provided wherein a heterologous plant promoter is operably linked to a CcRpp2-R1 or CcRpp2-R3 coding sequence selected from the group consisting of SEQ ID NOs: 1, 3, 5-20 and 37-47 or a polynucleotide having at least 85%, 90%, 95% or 99% sequence identity to SEQ ID NOs: 1, 3, 5-20 and 37-47. In one embodiment a recombinant polynucleotide is provided wherein a heterologous plant promoter is operably linked to a CcRpp2-R1 or CcRpp2-R3 coding sequence selected from the group consisting of SEQ ID NOs: 1 or 3 or a polynucleotide having at least 85%, 90%, 95% or 99% sequence identity to SEQ ID NOs: 1 or 3. In one embodiment a recombinant polynucleotide is provided wherein a heterologous plant promoter is operably linked to a CcRpp2-R1 or CcRpp2-R3 coding sequence selected from the group consisting of SEQ ID NOs: 1 or 3.

In some aspects of the present disclosure, the nucleic acid sequences can be stacked with any combination of polynucleotide sequences of interest in order to create plants with a desired phenotype. This stacking can be accomplished by a combination of genes within a DNA construct, or by crossing one or more plants having transgenes with another plant line that comprises a desired combination. For example, the polynucleotides of the present disclosure or fragments thereof can be stacked with any other polynucleotides of the disclosure, or with other genes. The combinations generated can also include multiple copies of any one of the polynucleotides of interest. The polynucleotides of the present disclosure can also be stacked with any other gene or combination of genes to produce plants with a variety of desired trait combinations including and not limited to traits desirable for animal feed such as high oil genes, balanced amino acids, increased digestibility, insect, disease or herbicide resistance, avirulence and disease resistance genes, agronomic traits (e.g, male sterility, flowering time) and/or transformation technology traits (e.g., cell cycle regulation or gene targeting).

These stacked combinations can be created by any method including and not limited to cross breeding plants by any conventional or known methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that can suppress the expression of the polynucleotide of interest. This can be combined with any combination of other suppression cassettes or overexpression cassettes to generate the desired combination of traits in the plant.

In one embodiment, the stacked combination includes one or more genes encoding pesticidal proteins including, but not limited to: insecticidal proteins from *Pseudomonas* sp. such as PSEEN3174 (Monalysin; (2011) PLOS Pathogens 7:1-13); from *Pseudomonas protegens* strain CHA0 and Pf-5 (previously fluorescens) (Pechy-Tarr, (2008) Environmental Microbiology 10:2368-2386; GenBank Accession No. EU400157); from *Pseudomonas taiwanensis* (Liu, et al., (2010) J. Agric. Food Chem., 58:12343-12349) and from *Pseudomonas pseudoalcaligenes* (Zhang, et al., (2009) Annals of Microbiology 59:45-50 and Li, et al., (2007) Plant Cell Tiss. Organ Cult. 89:159-168); insecticidal proteins from *Photorhabdus* sp. and *Xenorhabdus* sp. (Hinchliffe, et al., (2010) The Open Toxicology Journal, 3:101-118 and Morgan, et al., (2001) Applied and Envir. Micro. 67:2062-2069); U.S. Pat. Nos. 6,048,838, and 6,379,946; a PIP-1 polypeptide of U.S. Pat. No. 9,688,730; an AflP-1A and/or AflP-1B polypeptide of U.S. Pat. No. 9,475,847; a PIP-47 polypeptide of US Publication Number US20160186204; an IPD045 polypeptide, an IPD064 polypeptide, an IPD074 polypeptide, an IPD075 polypeptide, and an IPD077 polypeptide of International Patent Application Publication Number WO 2016/114973; an IPD080 polypeptide of PCT Serial Number PCT/US17/56517; an IPD078 polypeptide, an IPD084 polypeptide, an IPD085 polypeptide, an IPD086 polypeptide, an IPD087 polypeptide, an IPD088 polypeptide, and an IPD089 polypeptide of Serial Number PCT/US17/54160; PIP-72 polypeptide of US Patent Publication Number US20160366891; a PtIP-50 polypeptide and a PtIP-65 polypeptide of US Publication Number US20170166921; an IPD098 polypeptide, an IPD059 polypeptide, an IPD108 polypeptide, an IPD109 polypeptide of US Serial number 62/521084; a PtIP-83 polypeptide of US Publication Number US20160347799; a PtIP-96 polypeptide of US Publication Number US20170233440; an IPD079 polypeptide of PCT Publication Number WO2017/23486; an IPD082 polypeptide of PCT Publication Number WO 2017/105987, an IPD090 polypeptide of Serial Number PCT/US17/30602, an IPD093 polypeptide of U.S. Ser. No. 62/434,020; an IPD103 polypeptide of Serial Number PCT/US17/39376; an IPD101 polypeptide of U.S. Ser. No. 62/438,179; an IPD121 polypeptide of U.S. Ser. No. 62/508, 514; and δ-endotoxins including, but not limited to a Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry46, Cry47, Cry49, Cry50, Cry51, Cry52, Cry53, Cry54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry 72 classes of δ-endotoxin polypeptides and the *B. thuringiensis* cytolytic cyt1 and cyt2 genes. Members of these classes of *B. thuringiensis* insecticidal proteins can be found in Crickmore, et al., "*Bacillus thuringiensis* toxin nomenclature" (2011), at life-sci.sussex.ac.uk/home/Neil_Crickmore/Bt/ which can be accessed on the world-wide web using the "www" prefix).

In another embodiment, the stacked combination includes a polynucleotide encoding resistance to an herbicide that inhibits the growing point or meristem, such as an imidazolinone or a sulfonylurea. Exemplary genes in this category code for mutant ALS and AHAS enzyme as described, for example, by Lee, et al., (1988) EMBO J. 7:1241 and Miki, et al., (1990) Theor. Appl. Genet. 80:449, respectively. See also, U.S. Pat. Nos. 5,605,011; 5,013,659; 5,141,870; 5,767, 361; 5,731,180; 5,304,732; 4,761,373; 5,331,107; 5,928,937 and 5,378,824; U.S. patent application Ser. No. 11/683,737 and International Publication WO 1996/33270.

In another embodiment, the stacked combination includes a polynucleotide encoding a protein for resistance to Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876; 6,040,497; 5,804,425; 5,633,435; 5,145,783; 4,971,908; 5,312,910; 5,188,642; 5,094,945; 4,940,835; 5,866,775; 6,225,114; 6,130,366; 5,310,667; 4,535,060; 4,769,061; 5,633,448; 5,510,471; Re. 36,449; RE 37,287 and 5,491,288 and International Publications EP 1173580; WO 2001/66704; EP 1173581 and EP 1173582, which are incorporated herein by reference for this purpose. Glyphosate resistance is also imparted to plants that express a gene encoding a glyphosate oxido-reductase enzyme as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyl-transferase. See, for example, U.S. Pat. Nos. 7,462,481; 7,405,074 and US Patent Application Publication Number US 2008/0234130. A DNA molecule encoding a mutant aroA gene can be obtained under ATCC® Accession Number 39256, and the nucleotide sequence of the mutant gene is disclosed in U.S. Pat. No. 4,769,061 to Comai. EP Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in EP Application Numbers 0 242 246 and 0 242 236 to Leemans, et al.; De Greef, et al., (1989) Bio/Technology 7:61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 and 5,879,903, which are incorporated herein by reference for this purpose. Exemplary genes conferring resistance to phenoxy proprionic acids and cyclohexones, such as sethoxydim and haloxyfop, are the Acc1-S1, Acc1-S2 and Acc1-S3 genes described by Marshall, et al., (1992) Theor. Appl. Genet. 83:435.

In another embodiment, the stacked combination includes a polynucleotide encoding a protein for resistance to herbicide that inhibits photosynthesis, such as a triazine (psbA and gs+genes) and a benzonitrile (nitrilase gene). Przibilla, et al., (1991) Plant Cell 3:169, describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC® Accession Numbers 53435, 67441 and 67442. Cloning and expression of DNA coding for a glutathione S-transferase is described by Hayes, et al., (1992) Biochem. J. 285:173.

In another embodiment, the stacked combination includes a polynucleotide encoding a protein for resistance to Aceto-hydroxy acid synthase, which has been found to make plants that express this enzyme resistant to multiple types of herbicides, has been introduced into a variety of plants (see, e.g., Hattori, et al., (1995) Mol Gen Genet. 246:419). Other genes that confer resistance to herbicides include: a gene encoding a chimeric protein of rat cytochrome P4507A1 and yeast NADPH-cytochrome P450 oxidoreductase (Shiota, et al., (1994) Plant Physiol 106:17), genes for glutathione reductase and superoxide dismutase (Aono, et al., (1995) Plant Cell Physiol 36:1687) and genes for various phosphotransferases (Datta, et al., (1992) Plant Mol Biol 20:619).

In another embodiment, the stacked combination includes a polynucleotide encoding resistance to an herbicide targeting Protoporphyrinogen oxidase (protox) which is necessary for the production of chlorophyll. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,83 and 5,767,373 and International Publication WO 2001/12825.

In another embodiment, the stacked combination includes an aad-1 gene (originally from *Sphingobium herbicido-*

*vorans*) encoding the aryloxyalkanoate dioxygenase (AAD-1) protein. The trait confers tolerance to 2,4-dichlorophenoxyacetic acid and aryloxyphenoxypropionate (commonly referred to as "fop" herbicides such as quizalofop) herbicides. The aad-1 gene, itself, for herbicide tolerance in plants was first disclosed in WO 2005/107437 (see also, US 2009/0093366). The aad-12 gene, derived from Delftia acidovorans, which encodes the aryloxyalkanoate dioxygenase (AAD-12) protein that confers tolerance to 2,4-dichlorophenoxyacetic acid and pyridyloxyacetate herbicides by deactivating several herbicides with an aryloxyalkanoate moiety, including phenoxy auxin (e.g., 2,4-D, MCPA), as well as pyridyloxy auxins (e.g., fluroxypyr, triclopyr).

In another embodiment, the stacked combination includes a polynucleotide encoding an herbicide resistant dicamba monooxygenase disclosed in US Patent Application Publication 2003/0135879 for imparting dicamba tolerance.

In another embodiment, the stacked combination includes a polynucleotide encoding bromoxynil nitrilase (Bxn) disclosed in U.S. Pat. No. 4,810,648 for imparting bromoxynil tolerance.

In another embodiment, the stacked combination includes a polynucleotide encoding phytoene (crtl) described in Misawa, et al., (1993) Plant J. 4:833-840 and in Misawa, et al., (1994) Plant J. 6:481-489 for norflurazon tolerance.

In another embodiment, the stacked combination includes a polynucleotide encoding a protein that confers or contributes to an altered grain characteristic, such as altered fatty acids, for example, by:
- (1) Down-regulation of stearoyl-ACP to increase stearic acid content of the plant. See, Knultzon, et al., (1992) Proc. Natl. Acad. Sci. USA 89:2624 and WO 1999/64579 (Genes to Alter Lipid Profiles in Corn).
- (2) Elevating oleic acid via FAD-2 gene modification and/or decreasing linolenic acid via FAD-3 gene modification (see, U.S. Pat. Nos. 6,063,947; 6,323,392; 6,372,965 and WO 1993/11245).
- (3) Altering conjugated linolenic or linoleic acid content, such as in WO 2001/12800.
- (4) Altering LEC1, AGP, Dek1, Supera11, mi1 ps, and various Ipa genes such as Ipa1, Ipa3, hpt or hggt. For example, see, WO 2002/42424, WO 1998/22604, WO 2003/011015, WO 2002/057439, WO 2003/011015, U.S. Pat. Nos. 6,423,886, 6,197,561, 6,825,397 and US Patent Application Publication Numbers US 2003/0079247, US 2003/0204870 and Rivera-Madrid, et al., (1995) Proc. Natl. Acad. Sci. 92:5620-5624.
- (5) Genes encoding delta-8 desaturase for making long-chain polyunsaturated fatty acids (U.S. Pat. Nos. 8,058,571 and 8,338,152), delta-9 desaturase for lowering saturated fats (U.S. Pat. No. 8,063,269), Primula Δ6-desaturase for improving omega-3 fatty acid profiles.
- (6) Isolated nucleic acids and proteins associated with lipid and sugar metabolism regulation, in particular, lipid metabolism protein (LMP) used in methods of producing transgenic plants and modulating levels of seed storage compounds including lipids, fatty acids, starches or seed storage proteins and use in methods of modulating the seed size, seed number, seed weights, root length and leaf size of plants (EP 2404499).
- (7) Altering expression of a High-Level Expression of Sugar-Inducible 2 (HSI2) protein in the plant to increase or decrease expression of HSI2 in the plant. Increasing expression of HSI2 increases oil content while decreasing expression of HSI2 decreases abscisic acid sensitivity and/or increases drought resistance (US Patent Application Publication Number 2012/0066794).
- (8) Expression of cytochrome b5 (Cb5) alone or with FAD2 to modulate oil content in plant seed, particularly to increase the levels of omega-3 fatty acids and improve the ratio of omega-6 to omega-3 fatty acids (US Patent Application Publication Number 2011/0191904).
- (9) Nucleic acid molecules encoding wrinkled1-like polypeptides for modulating sugar metabolism (U.S. Pat. No. 8,217,223).

A feature of the present disclosure are methods comprising introducing a polynucleotide into a plant. In some aspects of the present disclosure, the polynucleotide can be presented in such a manner that the sequence gains access to the interior of a cell of the plant, including its potential insertion into the genome of a plant. The methods of the present disclosure do not depend on a particular method for introducing a sequence into a plant, only that the polynucleotide gains access to the interior of at least one cell of the plant.

A polynucleotide can be transiently or stably introduced into a host cell and can be maintained non-integrated, for example, as a plasmid.

Transformation methods as well as methods for introducing polynucleotide sequences into plants can depend on the type of plant or plant cell, i.e., monocot or dicot, targeted for transformation. Suitable methods of introducing polypeptides and polynucleotides into plant cells include, but are not limited to, microinjection, electroporation, direct gene transfer, Lecl transformation and ballistic particle acceleration. As newer methods become available, they can also be applied to the present disclosure as the method of transformation or transfection is not critical.

The cells that have been transformed can be grown into plants in accordance with conventional ways. These plants can then be grown, and either pollinated with the same transformed strain or different strains, and the resulting progeny having constitutive expression of the desired phenotypic characteristic identified. Two or more generations can be grown to ensure that expression of the desired phenotypic characteristic is stably maintained and inherited and then seeds harvested to ensure expression of the desired phenotypic characteristic has been achieved. In some aspects of the present disclosure, the transformed seed or transgenic seed having a nucleotide construct or an expression cassette is stably incorporated into their genome.

In an aspect, the present disclosure encompasses seeds comprising a polynucleotide sequence disclosed herein that can develop into or can be used to develop a plant or plants with increased or enhanced resistance to a pathogen (e.g., fungi) or infection caused by a pathogen as compared to, for example, a wild-type variety of the plant seed. In an aspect, the present disclosure features seeds from transgenic legume crop plants wherein the seed comprises a polynucleotide disclosed herein.

The present disclosure can be used for transformation of any plant species, including, but not limited to, monocots and dicots. Examples of plants of interest include, but are not limited to, corn (*Zea mays*), *Brassica* spp. (e.g., *Brassica napus, Brassica rapa, Brassica juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Per sea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

In an aspect, plants of interest include, a legume crop species, including, but not limited to, alfalfa (*Medicago sativa*); clover or trefoil (*Trifolium* spp.); pea, including (*Pisum satinum*), pigeon pea (*Cajanus cajan*), cowpea (*Vigna unguiculata*) and *Lathyrus* spp.; bean (Fabaceae or Leguminosae); lentil (*Lens culinaris*); lupin (*Lupinus* spp.); mesquite (*Prosopis* spp.); carob (*Ceratonia siliqua*), soybean (*Glycine max*), peanut (*Arachis hypogaea*) or tamarind (*Tamarindus indica*). The terms "legume species" and "legume crop species" are used herein to refer to plants, and can be for example, a plant of interest. In some aspects, the legume species or legume crop species is a plant, plant part or plant cell.

In an aspect, constructs or vectors or expression cassettes are not present in the genome of the original plant or are present in the genome of the transgenic plant, but not at their natural locus of the genome of the original plant.

The compositions disclosed herein can be generated or maintained through the process of introgressing. Introgressing is sometimes called "backcrossing" when the process is repeated two or more times. In introgressing or backcrossing, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the FI generation; the term "BC1" then refers to the second use of the recurrent parent, and "BC2" refers to the third use of the recurrent parent, and so on.

Accordingly, an aspect of the present disclosure is a method of enhancing plant resistance to a plant disease, such as ASR. The method can comprise conferring resistance to a pathogen, for example, a pathogen that causes ASR, by introgression of legume-derived CcRpp2-R1 and CcRpp2-R3 binary resistance genes, or homologs thereof, into germplasm in a breeding program (i.e., a breeding program for resistance to ASR).

The term "germplasm" is used herein to mean genetic material of or from an individual (e.g., a plant), a group of individuals (e.g., a plant line, variety or family), or a clone derived from a line, variety, species, or culture. The germplasm can be part of an organism or cell, or can be separate from the organism or cell. The germplasm provides genetic material with a specific molecular makeup that provides a physical foundation for some or all of the hereditary qualities of an organism or cell culture. Germplasm in the context of the present disclosure includes cells, seed or tissues from which new plants can be grown, or plant parts, such as leaves, stems, pollen, or cells, that can be cultured into a whole plant.

Aspects of the present disclosure comprise methods for identification of germplasm as a source of resistance including, but not limited to, germplasm in one or more of the following genus: *Glycine, Vigna,* and *Lablab.*

In one embodiment, the legume crop species or legume-derived gene is derived from the genus *Glycine.* Examples of *Glycine* species include, but are not limited to, *Glycine arenaria, Glycine argyrea, Glycine cyrtoloba, Glycine canescens, Glycine clandestine, Glycine curvata, Glycine falcata, Glycine latifolia, Glycine microphylla, Glycine pescadrensis, Glycine stenophita, Glycine syndetica, Glycine soja, Glycine tabacina* and *Glycine tomentella.*

In another embodiment, the legume crop species or legume-derived gene is derived from the genus *Vigna. Vigna* is a pantropic genus that comprises approximately 100 species. It is a taxonomic group subdivided into the subgenera *Vigna, Haydonia, Plectotropis* (African), *Ceratotropis* (Asian), *Sigmoidotropis,* and *Lasiopron.* The genus includes economically relevant species such as *Vigna unguiculata* (L.) *Walp* (cowpea), *Vigna radiata* (L.) Wilczek (mung bean), *Vigna angularis* (Willd.) Ohwi and Ohashi (azuki bean), *Vigna mungo* (L.) Hepper (black gram), and *Vigna umbellata* (Thunb.) Ohwi and Ohashi (rice bean). Four subspecies are recognized within *Vigna unguiculata:* dendtiana, a wild relative of cultivated subspecies; cylindrica, cultivated catjang; sesquipedalis, cultivated yardlong bean; and unguiculata, cultivated black-eyed pea. *Vigna unguiculata* ssp. *unguiculata* is further divided into cultivar groups *Unguiculata,* grown as a pulse; *Biflora* or *Cilindrica* (catjang), mainly used as a forage; *Sesquipedalis* (yardlong or asparagus bean), grown as a vegetable; *Textilis,* cultivated for the fibres of its long floral peduncles; and *Melanophthalmus* (black-eyed pea). Susceptibility of several *Vigna* species, including *Vigna radiata, Vigna mungo* and *Vigna unguiculata* to *Phakopsora pachyrhizi* has been reported under field and greenhouse conditions.

In another embodiment, the legume crop species or legume-derived gene is derived from the genus *Lablab. Lablab purpureus* (L.) Sweet is a *leguminous* species (Verdcourt (1971) Flora of Tropical East Africa, pp. 696-699, Crown Agents, London, UK; and Duke et al. (1981) Handbook of Legumes of World Economic Importance, pp. 102-106, Plenum Press, New York, USA and London, UK) native to Asia and Africa (Pengelly and Maass, (2001) Gen. resour. crop ev. 48: 261-272). It is commonly known as lablab bean, hyacinth bean, bonavist bean, field bean, Egyptian bean, poor man's bean, Tonga bean (English) and by at least 20 additional vernacular names. It is grown in Africa, Asia, and the Caribbean as either a pulse crop or as a green vegetable (Duke et al. (1981) Handbook of Legumes of World Economic Importance, pp. 102-106, Plenum Press, New York, USA and London, UK); and Pengelly and Maass, (2001) Gen. resour. crop ev. 48: 261-272).

*Lablab purpureas* has been reported as an alternative host for *Phakopsora pachyrhizi* (Perez-Hernandez, (2007) Alternative hosts of *Phakopsora pachyrhizi* in the Americas: An analysis of their role in the epidemiology of Asian soybean rust in the continental U.S. M.Sc. thesis. Iowa State University. Ames, Iowa. U.S.A.; Vakili (1981) Plant Dis. 65: 817-819; and Poonpolgul and Surin, (1980) Soybean Rust Newsletter, 3: 30-31).

In an aspect, the legume crop species or legume-derived gene is derived from the genus *Cicer, Cajanus, Medicago, Phaseolus, Pisum, Pueraria,* or *Trifolium.* Examples of *Cicer* species include, but are not limited to, *Cicer arietinum, Cicer echinospermum, Cicer reticulatum* and *Cicer pinnatifldum.* An example of the *Cajanus* species include, but is not limited to *Cajanus cajan.* Examples of the *Medicago* species include, but are not limited to, *Medicago truncatula* and *Medicago sativa.* Examples of the *Phaseolus* species include, but are not limited to, *Phaseolus vulgaris, Phaseolus lunatus, Phaseolus acutifolius* and *Phaseolus coccineus.* Examples of the *Pisum* species include, but are not limited to, *Pisum abyssinicum, Pisum sativum, Pisum elatius, Pisum fulvum, Pisum transcaucasium* and *Pisum humile.* An example of the *Pueraria* species includes, but is not limited to, *Pueraria lobata.* Examples of the *Trifolium* species include, but are not limited to, *Trifolium aureum* and *Trifolium occidentale.*

The present disclosure also comprises sequences described herein that can be provided in expression cassettes or DNA constructs for expression in the plant of interest. In an aspect, the cassette can include 5' and 3' heterologous regulatory sequences operably linked to a sequence disclosed herein. "Operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation. Such regulatory sequences are well known in the art and include those that direct constitutive expression of a nucleotide sequence in many types of host cells and those that direct expression of the nucleotide sequence in certain host cells or under certain conditions. The design of the vector can depend on, for example, the type of the host cell to be transformed or the level of expression of nucleic acid desired. The cassette can contain one or more additional genes to be co-transformed into the plant. And, any additional gene(s) can be provided on multiple expression cassettes.

Expression cassettes of the present disclosure can include many restriction sites for insertion of the nucleotide sequence to be under the transcriptional regulation of the regulatory regions. The expression cassette can also contain selectable marker genes.

An expression cassette can further include in the 5'-3' direction of transcription, a transcriptional and translational initiation region, a DNA sequence of the disclosure, and a transcriptional and translational termination region functional in plants. The transcriptional initiation region, the promoter, can be native or analogous or foreign or heterologous to the plant host. Additionally, the promoter can be the natural sequence or alternatively a synthetic sequence. The term "foreign" means that the transcriptional initiation region is not found in the native plant into which the transcriptional initiation region is introduced. As used herein, a chimeric gene comprises a coding sequence operably linked to a transcription initiation region that is heterologous to the coding sequence. Examples of promoters include, but are not limited to, the Cauliflower Mosaic Virus 35S and soybean Ubiquitin 6.

While it may be preferable to express the sequences using heterologous promoters, homologous promoters or native promoter sequences can be used. Such constructs would change expression levels in the host cell (i.e., plant or plant cell). Thus, the phenotype of the host cell (i.e., plant or plant cell) is altered.

A termination region can be native with the transcriptional initiation region, native with the operably linked DNA sequence of interest, or derived from another source. Convenient termination regions are available from the Ti-plasmid of *Agrobacterium tumefaciens,* such as the octopine synthase and nopaline synthase termination regions.

In an aspect, endogenous or transgenic resistance orthologs can be altered by homologous or non-homologous recombinatory methods, such as, for example, by genome editing. Such alterations refer to a nucleotide sequence having at least one modification when compared to its non-modified sequence and include, for example: (i) replacement of at least one nucleotide, (ii) deletion of at least one nucleotide, (iii) insertion of at least one nucleotide, or (iv) any combination of (i)-(iii).

In some embodiments, the disclosed CcRpp2-R1 and CcRpp2-R3 polynucleotide compositions can be introduced into the genome of a plant using genome editing technologies, or previously introduced CcRpp2-R1 and CcRpp2-R3 polynucleotides in the genome of a plant may be edited using genome editing technologies.

For example, the disclosed polynucleotides can be introduced into a desired location in the genome of a plant through the use of double-stranded break technologies such as TALENs, meganucleases, zinc finger nucleases, CRISPR-Cas, and the like. For example, the disclosed polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

"Target site," "target sequence," "target DNA," "target locus," "genomic target site," "genomic target sequence," and "genomic target locus" are used interchangeably herein and refer to a polynucleotide sequence, for example in the genome (including chloroplastic and mitochondrial DNA) of a cell, to which an endonuclease is recruited, and optionally nicks or cleaves the DNA of the target site. The target site can be an endogenous site in the plant genome, or alternatively, the target site can be heterologous to the plant and thereby not be naturally occurring in the genome, or the target site can be found in a heterologous genomic location compared to where it occurs in nature.

In some embodiments, where the disclosed CcRpp2-R1 and CcRpp2-R3 polynucleotides have previously been introduced into a genome or are endogenous homologs of CcRpp2-R1 and CcRpp2-R3 in other legume species, genome editing technologies may be used to alter or modify the introduced polynucleotide sequences or the endogenous homologs. Site specific modifications that can be introduced into the disclosed CcRpp2-R1 and CcRpp2-R3 polynucleotide compositions include those produced using any method for introducing site specific modification, including, but not limited to, through the use of gene repair oligonucleotides (e.g. U.S. Patent Application Publication No. 2013/0019349), or through the use of double-stranded break technologies such as TALENs, meganucleases, zinc finger nucleases, CRISPR-Cas, and the like. Such technologies can be used to modify the previously introduced polynucleotides through the insertion, deletion or substitution of nucleotides within the introduced polynucleotides. Alternatively, double-stranded break technologies can be used to add additional nucleotide sequences to the introduced polynucleotides. Additional sequences that may be added include, additional expression elements, such as enhancer and promoter sequences. In another embodiment, genome editing technologies may be used to position coding sequences for additional ASR resistance proteins in close proximity to the disclosed CcRpp2-R1 and CcRpp2-R3 polynucleotide compositions disclosed herein within the genome of a plant, in order to generate molecular stacks of ASR-resistance proteins.

An "altered target site," "altered target sequence," "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

The gene(s) can be optimized for increased expression in the transformed plant as needed. In other words, the genes can be synthesized using plant-preferred codons for improved expression. Methods for synthesizing plant-preferred genes are known in the art.

Additional sequence modifications are known to enhance gene expression in a cellular host. These include elimination of sequences encoding spurious polyadenylation signals, exon-intron splice site signals, transposon-like repeats, and other such well-characterized sequences that can be deleterious to gene expression. The G-C content of the sequence can be adjusted to levels average for a given cellular host, as calculated by reference to known genes expressed in the host cell. When possible, the sequence is modified to avoid predicted hairpin secondary mRNA structures.

The expression cassettes can additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region); potyvirus leaders, for example, TEV leader (Tobacco Etch Virus), and human immunoglobulin heavy chain binding protein (BiP); untranslated leader from the coat protein mRNA of alfalfa mosaic virus (AMV RNA 4); tobacco mosaic virus leader (TMV); and maize chlorotic mottle virus leader (MCMV) (Lommel et al. (1991) Virology 81:382 385). Other methods known to enhance translation can also be utilized, such as, introns.

The various DNA fragments can be manipulated while preparing the expression cassette, to ensure that the DNA sequences are in the proper orientation and, as appropriate, in the proper reading frame. Toward this end, adapters or linkers can be employed to join the DNA fragments. Alternatively, other manipulations can be used to provide for convenient restriction sites, removal of superfluous DNA, or removal of restriction sites. For this purpose, in vitro mutagenesis, primer repair, restriction, annealing, resubstitutions, e.g., transitions and transversions, can be involved.

Generally, the expression cassette can comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, imidazolinones, and 2,4-dichlorophenoxyacetate (2,4-D). The above list of selectable marker genes is not meant to be limiting. Any selectable marker gene can be used in the present disclosure.

For expression of a target gene and/or protein (e.g., one or more CcRpp2-R1 and CcRpp2-R3 genes and/or one or more CcRpp2-R1 and CcRpp2-R3 proteins) of the present disclosure in a plant or plant cell, the methods described herein comprise transforming a plant or plant cell with a polynucleotide, for example, as disclosed herein, that encodes the target protein. The polynucleotides described herein can be operably linked to a promoter that drives expression in a plant cell. Any promoter known in the art can be used in the methods of the present disclosure including, but not limited to, constitutive promoters, pathogen-inducible promoters, wound-inducible promoters, tissue-preferred promoters, and chemical-regulated promoters. The choice of promoter may depend on the desired timing and location of expression in the transformed plant as well as other factors, which are known to those of skill in the art. Transformed cells or plants can be grown or bred to generate a plant comprising one or more of polynucleotides that were introduced into the cell or plant that, for example, encodes CcRpp2-R1 and CcRpp2-R3 proteins.

A number of promoters can be used in the practice of the disclosure. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 promoter and other constitutive promoters disclosed in WO 99/43838 and U.S. Pat. No. 6,072,050; the core CaMV 35S promoter; rice actin; ubiquitin; pEMU; MAS; ALS; and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611, which are known in the art, and can be contemplated for use in the present disclosure.

Generally, it can be beneficial to express the gene from an inducible promoter, particularly from a pathogen-inducible promoter. Such promoters include those from pathogenesis-related proteins (PR proteins), which are induced following infection by a pathogen, e.g., PR proteins, SAR proteins, beta-1,3-glucanase, chitinase, etc.

Of interest are promoters that are expressed locally at or near the site of pathogen infection. Additionally, as pathogens find entry into plants through wounds or insect damage, a wound-inducible promoter can be used in the constructions of the disclosure. Such wound-inducible promoters include potato proteinase inhibitor (pin II) gene, wun1 and wun2, win1 and win2, systemin, WIP1, MPI gene, and the like.

Chemical-regulated promoters can be used to modulate the expression of a gene in a plant through the application of an exogenous chemical regulator. Depending upon the objective, the promoter can be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (e.g., the glucocorticoid-inducible promoter, and tetracycline-inducible and tetracycline-repressible promoters).

Tissue-preferred promoters can be utilized to target enhanced expression of the target genes or proteins (e.g., polynucleotide sequences encoding legume-derived CcRpp2-R1 and CcRpp2-R3 polypeptides) within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) Plant J. 12(2): 255 -265; Kawamata et al. (1997) Plant Cell Physiol. 38(7):792-803; Hansen et al. (1997) Mol. Gen Genet. 254(3):337-343; Russell et al. (1997) Transgenic Res. 6(2): 157-168; Rinehart et al. (1996) Plant Physiol. 112(3): 1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20: 181-196; Orozco et al. (1993) Plant Mol Biol. 23(6): 1129-1138; Matsuoka et al. (1993) Proc Natl. Acad. Sci. USA 90(20):9586-9590; and Guevara-Garcia et al. (1993) Plant J. 4(3):495-505. Such promoters can be modified.

Leaf-specific promoters are known in the art. See, for example, Yamamoto et al. (1997) Plant J. 12(2)255-265; Kwon et al. (1994) Plant Physiol. 105:357-67; Yamamoto et al. (1994) Plant Cell Physiol. 35(5):773-778; Gotor et al. (1993) Plant J. 3:509-18; Orozco et al. (1993) Plant Mol. Biol. 23(6): 1129-1138; and Matsuoka et al. (1993) Proc. Natl. Acad. Sci. USA 90(20):9586-9590.

"Seed-preferred" promoters include both "seed-specific" promoters (those promoters active during seed development such as promoters of seed storage proteins) as well as "seed-germinating" promoters (those promoters active during seed germination). Such seed-preferred promoters include, but are not limited to, Ciml (cytokinin-induced message), cZ19B1 (maize 19 kDa zein), milps (myo-inositol-1-phosphate synthase), and celA (cellulose synthase) (see WO 00/11177, herein incorporated by reference). Gama-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

Expression of the polynucleotides of the present disclosure can involve the use of the intact, native CcRpp2-R1 and CcRpp2-R3 genes, wherein the expression is driven by a cognate 5' upstream promoter sequence(s). Alternatively, expression can be generated using constructs assembled with 5' transcriptional control sequences provided by heterologous CcRpp2-R1 and CcRpp2-R3 disease resistance genes expressed in the host legume. One skilled in the art will be able to identify genes encoding CcRpp2-R1 and CcRpp2-R3 proteins following the teachings of this application, to evaluate their expression level, and to select preferred promoter sequences that can be used for expression of the CcRpp2-R1 and/or CcRpp2-R3 gene of interest. The use of either cognate or heterologous CcRpp2-R1 and CcRpp2-R3 promoter sequences provides an option to regulate protein expression to avoid or minimize any potential undesired outcomes associated with inappropriate or unwanted expression and plant defense activation.

Specific soybean promoters include but are not limited to soy ubiquitin (subi-1), elongation factor 1A, and S-adenosyl methionine synthase for constitutive expression and Rpp4, RPG1-B, and promoters contained in gene models such as Glyma promoters.

In another embodiment, transgenic plants expressing polynucleotides and polypeptides disclosed herein (i.e. the CcRpp2-R1 and CcRpp2-R3 resistance gene and polypeptide sequences) may also have one or more fungicides applied to the transgenic plants as a method of further preventing ASR associated damage to a legume crop species. These fungicidal compounds may also be applied to supplement the protection of a transgenic legume crop species comprising the CcRpp2-R1 and CcRpp2-R3 resistance gene sequences to a wider variety of undesirable diseases. These fungicides may be formulated or tank-mixed with other fungicide(s) disclosed herein or applied sequentially with the other fungicide(s). Such fungicides may include 2-(thiocyanatomethylthio)-benzothiazole, 2-phenylphenol, 8-hydroxyquinoline sulfate, ametoctradin, aminopyrifen, amisulbrom, antimycin, Ampelomyces quisqualis, azaconazole, azoxystrobin, Bacillus subtilis, Bacillus subtilis strain QST713, benalaxyl, benomyl, benthiavalicarb-isopropyl, benzovindiflupyr, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroinconazide, chloroneb, chlorothalonil, chlozolinate, Coniothyrium minitans, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, fluindapyr, flumorph, fluopicolide, fluopyram, fluoroimide, fluoxapiprolin, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), inpyrfluxam, iodocarb, ipconazole, ipfenpyrazolone, iprobenfos, iprodione, iprovalicarb, isofetamide, isoflucypram, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxathiapiprolin, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pydiflumetofen, pyrametostrobin, pyraoxystrobin, pyraclostrobin, pyraziflumid, pyrazophos, pyribencarb, pyributicarb, pyrifenox, pyrimethanil, pyriofenone, pyroquilon, quinoclamine, quinoxyfen, quintozene, Reynoutria sachalinensis extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)-N-(3,5-dichlorophenyl)-2-(methoxymethyl)-succinimide, 1,2-dichloropropane, 1,3-dichloro-1,1, 3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethyl-mercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril, benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, coumoxystrobin, cufraneb, cupric hydrazinium sulfate, cuprobam, cyclafuramid, cypendazole, cyprofuram, decafentin, dichlobentiazox, dichlone, dichlozoline, diclobutrazol, dimethirimol, dinocton, dinosulfon, dinoterbon, dipymetitrone, dipyrithione, ditalimfos, dodicin, drazoxolon, EBP, enoxastrobin, ESBP, etaconazole, etem, ethirim, fenaminstrobin, fenaminosulf, fenapanil, fenitropan, fenpicoxamid, florylpicoxamid, flubeneteram, flufenoxystrobin, fluopimomide, fluotrimazole, furcarbanil, furconazole, furconazole-cis, furmecyclox, furophanate, glyodine, griseofulvin, halacrinate, Hercules 3944, hexylthiofos, ICIA0858, ipfentriflu-conazole, ipflufenoquin, isopamphos, isovaledione, mandestrobin, mebenil, mecarbinzid, mefentrifluconazole, metazoxolon, methfuroxam, methylmercury dicyandiamide, metsulfovax, metyltetraprole, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyrapropoyne, pyridachlometyl, pyridinitril, pyrisoxazole, pyroxychlor, pyroxyfur, quinacetol; quinacetol sulfate, quinazamid, quinconazole, quinofumelin, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, triclopyricarb, triflumezopyrim, urbacid, zarilamid, (2S,3S)-3-(o-tolyl)butan-2-yl (4-methoxy-3-(propionyloxy)picolinoyl)-L-alaninate, and any combinations thereof.

The present disclosure also includes kits for the assays described herein. The polypeptide sequences and polynucleotides can be packaged as a component of a kit with instructions for completing the assay disclosed herein. The kits of the present disclosure can include any combination of the polypeptides and/or polynucleotides described herein and suitable instructions (written and/or provided as audio-, visual-, or audiovisual material). In one embodiment, the kit relates to a DNA detection kit for identifying TIR genes (e.g., CcRpp2-R1 and CcRpp2-R3 genes) or CcRpp2-R1 and CcRpp2-R3 proteins against ASR. Kits utilizing any of the sequences disclosed herein for the identification of a transgenic event (e.g., CcRpp2-R1 and CcRpp2-R3) in a plant for efficacy against ASR are provided. For example, the kits can comprise a specific probe having a sequence corresponding to or is complementary to a sequence having between 80% and 100% sequence identity with a specific region of the transgenic event. The kits can include any reagents and materials required to carry out the assay or detection method.

In accordance with embodiment 1 an ASR resistance polypeptide is provided selected from:

a) a CcRpp2-R1 polypeptide comprising an amino acid sequence having greater than 60% sequence identity compared to the amino acid sequence of any one of SEQ ID NOs: 2 and 21-36; or b) a CcRpp2-R3 polypeptide comprising an amino acid sequence having greater than 60% sequence identity compared to the amino acid sequence of any one of SEQ ID NOs: 4 and 48-58.

In accordance with embodiment 2 an ASR resistance composition is provided comprising a CcRpp2-R1 polypeptide of embodiment 1 and a CcRpp2-R3 polypeptide of embodiment 1.

In accordance with embodiment 3 a polynucleotide encoding an ASR resistance polypeptide is provided wherein the encoded polypeptide is selected from:

a) a CcRpp2-R1 polypeptide comprising an amino acid sequence having greater than 60% sequence identity compared to the amino acid sequence of any one of SEQ ID NOs: 2 and 21-36, optionally wherein the polynucleotide encoding an ASR resistance polypeptide is operably linked to a heterologous regulatory element such as a heterologous plant promoter; or b) a CcRpp2-R3 polypeptide comprising an amino acid sequence having greater than 60% sequence identity compared to the amino acid sequence of any one of SEQ ID NOs: 4 and 48-58, optionally wherein the polynucleotide encoding an ASR resistance polypeptide is operably linked to a heterologous regulatory element such as a heterologous plant promoter.

In accordance with embodiment 4 the recombinant polynucleotide of embodiment 3 is provided, wherein the recombinant polynucleotide is selected from:

a) a polynucleotide having at least 70% sequence identity to the polynucleotide of any one of SEQ ID NOs: 1 and 5-20; and b) the polynucleotide having at least 70% sequence identity to the polynucleotide of any one of SEQ ID NOs: 3 and 37-47.

In accordance with embodiment 5 a DNA construct is provided comprising, the recombinant polynucleotide of embodiment 3 or 4 and a heterologous regulatory sequence operably linked to the recombinant polynucleotide.

In accordance with embodiment 6 a transgenic plant or plant cell is provided comprising the DNA construct of any one of embodiments 1-5.

In accordance with embodiment 7 the transgenic plant of claim 6 is provided, wherein the plant is a legume crop plant.

In accordance with embodiment 8 a transgenic legume crop plant of embodiment 7 is provided, wherein transgenic legume crop plant is soybean.

In accordance with embodiment 9 a method of conferring disease resistance in a legume crop species is provided, wherein the method comprises transforming a legume crop species with a heterologous legume-derived CcRpp2-R1 gene and a heterologous legume-derived CcRpp2-R3 gene that confer disease resistance to a legume crop species disease.

In accordance with embodiment 10 a method of embodiment 9 is provided, wherein the legume crop species disease is caused by a plant pathogen.

In accordance with embodiment 11 a method of embodiment 9 or 10 is provided, wherein the plant pathogen is *Phakopsora pachyrhizi* or *Phakopsora meibomiae.*

In accordance with embodiment 12 a method of any one of embodiments 9-11 is provided, wherein the legume crop species disease is Asian soybean rust.

In accordance with embodiment 13 a method of any one of embodiments 9, 10, 11 or 12 is provided, wherein the legume crop species is an alfalfa, clover, pea, bean lentil, lupin, mesquite, carob, soybean, peanut or tamarind.

In accordance with embodiment 14 a method of any one of embodiments 9, 10, 11, 12 or 13 is provided, wherein the legume crop species is soybean.

In accordance with embodiment 15 a method of any one of embodiments 9, 10, 11, 12, 13 or 14 is provided, wherein the legume-derived CcRpp2-R1 or CcRpp2-R3 genes are derived from genus *Arachis, Cercis, Cajanus, Glycine, Medicago, Phaseolus, Pisum* or *Vigna.*

In accordance with embodiment 16 a transgenic legume crop plant of any one of embodiments 6-8 is provided, further comprising one or more additional resistance genes, optionally wherein the additional resistance gene is a CcRpp1 gene.

In accordance with embodiment 17 a transgenic legume crop plant of any one of embodiments 6-8 or 16 is provided, further comprising an improved agronomic trait.

In accordance with embodiment 18 a seed from the transgenic legume crop plant of embodiments 16 or 17, wherein the seed has a DNA construct of any one of embodiments 1-5.

In accordance with embodiment 19 a method of reducing one or more symptoms of a legume plant disease is provided, wherein the method comprises exposing the transgenic legume crop plant of any one of claims 6-8 to the legume plant disease wherein the transgenic legume crop plant has an enhanced resistance to the plant disease.

In accordance with embodiment 20 the method of embodiment 19 is provided, wherein the plant disease is Asian soybean rust.

In accordance with embodiment 21 a method of producing an Asian soybean rust resistant plant is provided, wherein the method comprising transforming a plant cell with a legume-derived CcRpp2-R1 gene and a legume-derived CcRpp2-R3 gene.

In accordance with embodiment 22 the method of embodiment 21 is provided, further comprising regenerating the transformed plant from the transformed plant cell.

In accordance with embodiment 22 the method of embodiment 22 is provided, further comprising the step of growing the transformed plant wherein the expression of the legume-derived CcRpp2-R1 gene and the legume-derived CcRpp2-R3 gene results in enhanced resistance to Asian soybean rust disease in the transformed plant.

In accordance with embodiment 23 the method of any one of embodiments 21-23 is provided, wherein the Asian soybean rust resistant plant is a legume species.

In accordance with embodiment 24 a legume plant is provided that is a progeny from a cross between a transgenic legume plant comprising a legume-derived CcRpp2-R1 gene and a legume-derived CcRpp2-R3 gene disclosed herein and a similar legume plant that is not transformed with the legume-derived CcRpp2-R1 gene and the legume-derived CcRpp2-R3 gene.

In accordance with embodiment 25 the plant of embodiment 24 is provided, wherein the legume plant is an alfalfa, clover, pea, bean, lentil, lupin, mesquite, carob, soybean, peanut or tamarind species.

In accordance with embodiment 26 a method of assaying a legume plant for disease resistance to a plant disease is provided, wherein the method comprises exposing a portion of the legume plant comprising a legume-derived CcRpp2-R1 gene and a legume-derived CcRpp2-R3 gene to a plant pathogen; measuring plant disease symptoms on the legume plant exposed to the plant pathogen; and comparing the plant disease symptoms to a reference standard for disease resistance, optionally wherein the plant disease is caused by a plant pathogen, optionally wherein the plant pathogen is caused by *Phakopsora pachyrhizi* or *Phakopsora meibomiae,* optionally wherein the plant disease is Asian soybean rust In accordance with embodiment 27 a method of enhancing plant resistance to Asian soybean rust (ASR) disease is provided, wherein the method comprises conferring resistance to an ASR pathogen by introgression of a legume-derived CcRpp2-R1 gene and a legume-derived CcRpp2-R3 gene into germplasm in a breeding program for resistance to ASR.

In accordance with embodiment 28 the method of embodiments 27 is provided, wherein the legume-derived CcRpp2-R1 gene encodes a polypeptide having at least 90% sequence identity to the polypeptide of SEQ ID NO: 2 and the legume-derived CcRpp2-R3 gene encodes a polypeptide having at least 90% sequence identity to the polypeptide of SEQ ID NO: 4.

In accordance with embodiment 29 the method of any one of embodiments 27 or 28 is provided, wherein the CcRpp2-R1 gene encodes the polypeptide of SEQ ID NO: 2 and the CcRpp2-R3 gene encodes the polypeptide of SEQ ID NO: 4, optionally wherein the germplasm is a legume crop species, optionally wherein the legume crop species is an alfalfa, clover, pea, bean, lentil, lupin, mesquite, carob, soybean, peanut or tamarind species, optionally wherein the legume crop species is soybean.

In accordance with embodiment 30 the method of embodiment 29 is provided, wherein a plant transformed with the polypeptide displays enhanced resistance to ASR when compared to a susceptible plant.

In accordance with embodiment 31 a recombinant DNA construct of embodiment 5 is provided, further comprising one or more NB-LRR polynucleotides or a fragment thereof.

In accordance with embodiment 32 a recombinant DNA construct of embodiment 5 or 31 is provided, The recombinant DNA construct of claim 5, further comprising one or more resistance genes.

In accordance with embodiment 32 a seed comprising the recombinant DNA construct of any one of embodiments 5, 31 or 32 is provided.

In accordance with embodiment 33 a plant comprising the recombinant DNA construct of any one of embodiments 5, 31 or 32 is provided.

In accordance with embodiment 34 a seed of embodiment 32 or a plant of embodiment 33 is provided wherein said seed or plant comprises a nucleic acid sequence encoding a polypeptide selected from:

a) a CcRpp2-R1 polypeptide comprising an amino acid sequence having greater than 90% sequence identity compared to the amino acid sequence of any one of
SEQ ID NOs: 2 and 21-36; or b) a CcRpp2-R3 polypeptide comprising an amino acid
sequence having greater than 90% sequence identity
compared to the amino acid sequence of any one of
SEQ ID NOs: 4 and 48-58.

In accordance with embodiment 34, the seed or plant of
embodiment 33 is provided wherein the CcRpp2-R1 poly-
peptide is SEQ ID NO: 2 and the CcRpp2-R3 polypeptide is
SEQ ID NO: 4, optionally wherein the CcRpp2-R1 poly-
nucleotide is SEQ ID NO: 1 and the CcRpp2-R3 polynucle-
otide is SEQ ID NO: 3.

The following examples are offered by way of illustration
and not by way of limitation.

EXAMPLE 1

Mapping and Cloning of CcRpp2 Genes

Pigeon pea (*Cajanus cajan*) is a diploid legume, with a
genome size of approximately 830 Mbp (Varshney et al.
(2012) Nat. Biotechnol., 30:83-89). The plant is self-fertile
and has a life cycle between 2-3 months seed-to-seed. *C.
cajan* (accession G108-99) was previously characterized as
exhibiting resistance to Asian Soybean Rust (ASR) disease.
As disclosed herein this variety was further screened to
investigate if additional uncharacterized resistance genes to
Asian Soybean Rust (ASR) disease, other than the known
CcRpp1 locus are present in the plant's genome. More
particularly, several segregating populations were generated
by crossing *C. cajan* (accession G108-99) with accessions
that show full susceptibility, including Ra, Rb, Rc, Rd, Re
and Rf. Segregation analysis indicated that a single major
resistance gene confers resistance in these populations,
except for the Rd population that showed a 15:1 segregation
pattern. Further analysis showed that the resistances
observed in these accessions map to the same locus, except
for a potential second locus in the Rd population.

Specifically, segregation and marker analysis were con-
ducted and demonstrated the existence of a second resis-
tance locus in the accession G108-99 (Rd). 292 F2 plants
from population CG8-1 (G48-95 x G108-99) were screened
with ASR isolate PPUFV-02. 266 plants were classified as
resistant and 24 as susceptible. The observed numbers fit a
15:1 segregation ratio expected for two independent genes.
The same population was screened using markers SSR10581
and dCAPS239615 that flank the interval that contains the
previously described CcRpp1. Based on this screening, 56
plants were selected that were homozygous susceptible for
this interval, i.e., do not contain the resistance allele at the
CcRpp1 locus. At least twelve plants homozygous for the
susceptible allele at the interval displayed an immune phe-
notype (class 0) corroborating the hypothesis on the exis-
tence of a new resistance locus in accession G108-99. These
56 F2 plants were selfed to obtain F3 seed. The F3 families
were inoculated with isolate PPUFV-02 and genotyped
using markers SSR10581 and dCAPS239615. The resis-
tance in some of these F3 families displayed a 3:1 segrega-
tion and markers analysis confirmed the presence of G48-95
DNA at CcRpp1 locus, corroborating the segregation of a
single resistance gene elsewhere in the *Cajanus* genome.

Two segregating F3 families were selected for mapping of
the new resistance locus. DNA was isolated and sent to The
DNA Facility at Iowa State University for SNP genotyping
using the Sequenom MassARRAY iPLEX platform. The
SNPs to be screened span the Cajanus genome at 10-20 cM intervals. They were selected after comparison of G48-95
and G108-99 genomic Illumina data.

Fine mapping and BAC library screens were used to
identify the physical interval of the new resistance gene
identified herein as CcRpp2 (See FIG. 1). Three BAC clones
were identified from a Rd library: BACP6 (116,744 bp),
BACJ17 (139,830 bp) and xcajanus-2 (161,443 bp). All
BACs include the markers Rdint_264620 and
dCAPS_393933, but they don't contain the marker
Rdint_385686. BACJ17 includes the full BACP6 and the
third BAC and neither of the BACs fully covers the interval
of 121 kb (FIG. 1). Using suitable markers one loss and one
gain of function recombinant on the distal side (marker
position Rdint_264620) and three loss of function recom-
binants on the proximal side of the interval on the marker
position Rdint_385686, were identified narrowing down the
interval to 121,252 bp. Rd BAC library were constructed
and screened using three markers located in this interval:
Rdint_264620; dCAPS_393933 and Rdint_385686.

The region between the contig_153610 and con-
tig_135277 harbours a sequence that resembles a TIR-NB-
LRR gene (homolog to Glyma14g024500). However, after
a more detailed observation by checking the C. cajan TIR-
NB-LRR sequence on the SMART (Simple Modular Archi-
tecture Research Tool; a web resource that provides a simple
identification and extensive annotation of protein domains
and the exploration of protein domain architectures), the
sequence was not a full NB-LRR gene but a TIR-TIR
domain. Four copies of the TIR domain are present twice in
the interval of 121,252 bp and appear to be duplicated.

To visualize the expressed genes the programs Geneious
and TopHat (fast splice junction mapper for RNAseq reads)
were used and the mapping results were analysed to identify
splice junctions between exons. The first TIR-TIR domain
set on the BAC did not show any polymorphism between the
resistant and susceptible transcriptome reads. Interestingly
though, a clear frameshift caused by a two nucleotide
deletion was observed in the TIR-TIR sequence of the
susceptible parent. In addition, TopHat analysis showed a
slight induction in the transcriptome dataset of the resistant
parent. Therefore this TIR-TIR sequence was a prime can-
didate for conferring the CcRpp2 resistance. The second
TIR-TIR domain did not show an induction in the resistant
transcriptome reads and no polymorphisms were detected
between the resistant and susceptible reads in the expressed
contigs. However, again a frame shift in the gene variant
present in the susceptible parent is intriguing.

The TIR-TIR gene found in BACJ17 (BACJ17 position:
63,676 to 66,081) is upregulated in the transcriptome of the
resistant parent (G108-99) in relation to the susceptible
transcriptome parent (G48-95). The TIR-TIR domains
encoded by this gene belong to a rare TIR-2 superfamily in
which the number of family members in the dicots is
restricted to 2-5 genes per species (Sarris et al., 2016). A CT
deletion on the second exon was present only in the sus-
ceptible allele (position on the BACJ17: 64,691) causing a
frameshift on the gene, which results in an early stop codon,
creating a short polypeptide sequence that will most likely
not be functional and contains only one TIR domain. This
CT deletion found in the susceptible allele S48 is fixed in
other four *C. cajan* accessions that do not convey resistance
at the CcRpp2 locus, indicating that this gene is likely to be
the CcRpp2 resistant gene candidate. A comparison of the
TIR-TIR gene present at the CcRpp2 locus of G108-99 to six
other accessions of *C. cajan* reveals that only G108-99
conveys resistance via the CcRpp1 and CcRpp2 locus.
G48-95 is the susceptible mother plant used in the cross.

G59-95, G119-99, G127-97 and G146-97 contain resistance at the CcRpp1 locus but do not convey resistance via the CcRpp2 locus.

RNA Ligase Mediated Rapid Amplification of cDNA Ends.

(RLM-RACE) was conducted on the first TIR-TIR gene present in the resistant accession to obtain the whole TIR-TIR gene sequence including the 5' and 3' UTRs. The RNA used for the RACE experiments was isolated from uninfected tissue and from non-etiolated leaf material. Interestingly, two different full length transcripts were observed, with one of them showing a deletion of 51 nucleotides at the end of the second exon. The two splice variants observed in the first TIR-TIR resistant transcript are caused by an alternative splicing event resulting in two variations of peptide sequences, with one losing 17 aa from their sequence but this event did not change the function of these two variants.

To determine the relative abundance of the full TIR-TIR transcript versus the splice variant RACE products the program TopHat was used to align the transcriptome of both parents against the updated version of the BACJ17. The relative abundance of the full TIR-TIR resistant transcript with a coverage of 220×the number of reads versus 9×the number of reads on the variant carrying the 51 nt deletion.

To identify the minimal effective promoter of the TIR-TIR transcript it was assumed that a shorter promoter length, not containing reads from the upstream RNA Helicase gene, has all the transcription elements to drive both TIRs gene expression in the soybean transformants.

EXAMPLE 2

Transformation of Soybean with the *Cajanus cajan* Genes, CcRpp2-R1Aa (SEQ ID NO: 1) and CcRpp2-R3Aa (SEQ ID NO: 3)

A plant transformation construct was designed to provide high-level constitutive expression of CcRpp2-R1Aa (SEQ ID NO: 1) and moderate-level constitutive expression of CcRpp2-R3Aa (SEQ ID NO: 3) in soybean. A slot vector was produced with a 1026 bp SfiI fragment containing the CcRpp2-R1Aa coding region that was ligated at the 5' end to a 1948 bp soybean ubiquitin promoter+IntronI fragment and on the 3' end to a 1163 bp phaseolin terminator fragment. The entire promoter-coding region-terminator cassette was flanked by attR1 and attL4 Gateway® recombination sites. A second slot vector was generated with a 1035 bp BamHI+SnaBI fragment containing the CcRpp2-R3Aa coding region that was ligated at the 5' end to a 2,576 bp maize histone 2B promoter+IntronI fragment and on the 3' end to a 902 bp soybean ubiquitin 14 (UBQ14) terminator fragment. The entire promoter-coding region-terminator cassette was located between Gateway attL3 and attR2 recombination sites. The final stacked gene construct was created by recombining the two promoter-coding region-terminator cassettes, separated by a 1,531 bp attL2 and attL1 flanked buffer fragment, in a Gateway based plant expression vector between compatible attR4 and attR3 recombination sites. This vector, in addition to the above elements, contained a spectinomycin resistance gene for bacterial selection and an herbicide resistant soybean ALS gene as a plant selectable marker.

The final CcRpp2Aa binary-containing plant expression vector was electroporated into *Escherichia coli*. Transformants were then selected and pDNA were isolated by standard miniprep methods. Transformants were characterized by diagnostic restriction enzyme digestions of miniprep DNA. A positive clone containing the expected pattern of digestion bands was selected and subsequently transformed into *Agrobacterium tumefaciens*. Transformants were selected, sequence verified to contain the binary CcRpp2Aa plant transformation construct, and submitted for *Agrobacterium*-mediated transformation.

*Agrobacterium*-mediated transformation of soybean. Transgenic soybean lines were produced from immature seed cultures following the *Agrobacterium*-mediated transformation protocol (Finer and McMullen 1991; Stewart et al. 1996; Cho et al. 2015). Briefly, immature seeds were harvested from soybean pods of plants grown in the greenhouse under standard conditions. Seeds were surface sterilized, immature cotyledons were aseptically excised and the cultures were maintained in 250 ml flasks containing 50 ml of liquid media on rotary shakers at 26° C. under cool white fluorescent lights with a 16/8 h day/night photoperiod (Samoylov et al. 1998; Cho et al. 2011). *Agrobacterium tumefaciens* carrying plasmids with genes of interest were used to transform the immature cotyledons. Transgenic events were selected and regenerated to maturity. These plants were grown under the same conditions as the wild type plants but in separate growth chambers.

Additional molecular stack constructs were assembled to express the genomic and predicted cDNA of both CcRpp2-R1Aa and CcRpp2-R3Aa behind either a soybean ubiquitin promoter or a maize histone 2B promoter for high-level or moderate-level expression, respectively. Events were generated from each of the additional constructs and confirmed to express the CcRpp2 transgenes. Homozygous and hemizygous plants displayed the red-brown (RB) phenotype when challenged with *Phakopsora pachyrhizi;* however, in contrast to event 1-2 (see below), the additional construct designs resulted in a reduced resistance profile with no significant decrease in sporulation detected.

EXAMPLE 3

Testing Transgenic Plants for Efficacy Against ASR

The molecular stack of CcRpp2-R1Aa (SEQ ID NO: 1) and CcRpp2-R3Aa (SEQ ID NO: 3) genes was tested for efficacy against ASR by transformation of the plant expression construct into soybean, followed by inoculation of transgenic plants with *Phakopsora pachyrhizi* and scoring of plant disease symptoms.

One transgenic event, event 1-2, was recovered from the soy transformation experiment and confirmed by qPCR to contain the CcRpp2-R1Aa and CcRpp2-R3Aa genes. The event was additionally shown by qRT-PCR to express a diagnostic 197 bp fragment of the CcRpp2-R1Aa transcript and a 202 bp fragment of the CcRpp2-R3Aa transcript.

T1 transgenic testing for efficacy of binary CcRpp2Aa against *Phakopsora pachyrhizi*. Seeds from one T1 event were planted and grown under growth chamber conditions for 15 days until Vc. The plants were sampled at V1 for qPCR to determine the transgene copy number and inoculated with a suspension of *Phakopsora pachyrhizi* spores. The inoculation was performed with urediniospores collected from a susceptible variety. Freshly harvested spores were suspended in an aqueous solution of 0.01% Tween 20 and mixed thoroughly; the spore concentration was then adjusted to $4 \times 10^3$ sp/ml with a hemocytometer. Plants were spray-inoculated with the urediniospore suspension, incubated at 100% relative humidity in the dark for 22 hours and then transferred to a growth chamber optimized for disease development (23° C., 70% RH, 16 hr photoperiod) where they were allowed to grow and develop symptoms for 15 days. New growth was excised regularly in order to keep the unifoliates for the duration of the experiment.

In order to assess the effect of the binary CcRpp2-R1Aa and CcRpp2-R3Aa, plants were scored qualitatively as Resistant (R; red-brown (RB), low or non-sporulating lesions), and Susceptible (S; tan, highly sporulating lesions) and quantitatively, by excising and scanning leaves followed by determination of lesion counts. The null, heterozygous and homozygous plants were scored 15 days after inoculation. In order to determine the effect of the binary gene, the transgenic plants were compared to the null plants from the same event.

ASR infection assay results were summarized in Table 2. These results showed that the binary CcRpp2Aa (CcRpp2-R1Aa and CcRpp2-R3Aa) in homozygous samples provided red-brown type resistance to ASR with little to no sporulation. Plant leaves were visually assessed for the presence of lesions and microscopically evaluated to detect the presence of uredinia. Low to no sporulation was observed on 95.45% of homozygous plants representing event 1-2 that were confirmed to express CcRpp2-R1Aa and CcRpp2-R3Aa, with one plant showing mid-level sporulation. Heterozygous plants also displayed resistance, red-brown lesions with low to no sporulation observed on 89.47% of plants; however, mid-level sporulation was observed on three plants and one heterozygous plant displayed high-level sporulation. Null plants contained tan, highly sporulating lesions, typical of a susceptible reaction to the pathogen.

These ASR infection assay results show that the binary CcRpp2 genes CcRpp2-R1Aa and CcRpp2-R3Aa were able to provide resistance to *Phakopsora pachyrhizi* when transgenically transferred from the host legume, *Cajanus cajan* to *Glycine max* plants.

Table 2. Measured traits for event 1-2 carrying binary CcRpp2Aa. Zygosity was used as transgene copy number (null=0, hemiz=1, homoz=2); R=resistant, S=susceptible; Avg LC/cm$^2$=average lesion count per area unit (cm$^2$); Phenotype pct=percent of plants with observed phenotype

| Event | Zygosity | n | Reaction | Lesion type | Sporulation | Phenotype (pct) | Avg (LC/cm$^2$) |
|---|---|---|---|---|---|---|---|
| 1-2 | Homoz | 22 | R | RB | None-Low | 95.45 | 12.37 |
| | Hemiz | 38 | R | RB | None-Low | 89.47 | 13.84 |
| | Null | 15 | S | Tan | High | 100 | 16.78 |

EXAMPLE 4

Identification of Homologous Proteins

Gene identities may be determined by conducting BLAST (Basic Local Alignment Search Tool; Altschul, et al., (1993) *J. Mol. Biol.* 215:403-410; see also ncbi.nlm.nih.gov/BLAST/, which can be accessed using the www prefix) searches under default parameters for similarity to sequences contained in the publicly available BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). In addition to public databases, proprietary internal databases were also searched. Certain polynucleotide sequences were analyzed. The resulting percent identity values of CcRpp2-R1Aa (SEQ ID NO: 1) and certain homologous proteins are presented in Table 3. The resulting percent identity values of CcRpp2-R3Aa (SEQ ID NO: 3) and certain homologous proteins are presented in Table 4.

TABLE 3

CcRpp2-R1Aa homologous proteins and their origins

| Reference | NT SEQ ID NO | AA SEQ ID NO | Percent Amino Acid Sequence Identity to full length CcRpp2-R1Aa (SEQ ID NO: 2) | Variety | Public Database Gene Reference | Source Organism |
|---|---|---|---|---|---|---|
| CcRpp2-R1Aa | 1 | 2 | — | — | — | *Cajanus cajan* |
| CcRpp2-R1Ad* | 5 | 21 | 45.22 | V14167 | aradu.V14167.gnm1.ann1.Aradu.L0FGB.1 gene = aradu.Aradu.L0FGB | *Arachis duranensis* |

TABLE 3-continued

CcRpp2-R1Aa homologous proteins and their origins

| Reference | NT SEQ ID NO | AA SEQ ID NO | Percent Amino Acid Sequence Identity to full length CcRpp2-R1Aa (SEQ ID NO: 2) | Variety | Public Database Gene Reference | Source Organism |
|---|---|---|---|---|---|---|
| CcRpp2-R1Ah* | 6 | 22 | 44.08 | Tifrunner | arahy.Tifrunner.gnm2.ann1.SGE08U.1 gene = arahy.SGE08U | *Arachis hypogaea* |
| CcRpp2-R1Ai* | 6 | 22 | 44.08 | K30076 | araip.K30076.gnm1.ann1.Araip.FPQ85.1 gene = araip.Araip.FPQ85 | *Arachis ipaensis* |
| CcRpp2-R1Cc* | 7 | 23 | 39.88 | ICPL87119 | cajca.ICPL87119.gnm1.ann1.C.cajan__05869.1 gene = cajca.C.cajan__05869 | *Cajanus cajan* |
| CcRpp2-R1Cc2* | 8 | 24 | 43.12 | ISC453364 | cerca.ISC453364.gnm1.ann1.Cerca571S26910 | *Cercis canadensis* |
| CcRpp2-R1Gs1 | 9 | 25 | 66.57 | PI483463 | glyso.PI483463.gnm1.ann1.GlysoPI483463.14G021900.1 gene = glyso.PI483463.gnm1.ann1.GlysoPI483463.14G021900 | *Glycine soja* |
| CcRpp2-R1Mt* | 10 | 26 | 49.86 | A17 | medtr.A17__HM341.gnm4.ann2.Medtr5g092630.1 gene = medtr.A17__HM341.Medtr5g092630 | *Medicago truncatula* |
| CcRpp2-R1Pv1 | 11 | 27 | 65.11 | G19833 | phavu.G19833.gnm2.ann1.Phvul.008G267700.1 gene = phavu.Phvul.008G267700 | *Phaseolus vulgaris* |
| CcRpp2-R1Ps1 | 12 | 28 | 30.50 | VC1973A | pissa.Cameor.gnm1.ann1.Psat2g013520.1 gene = pissa.Cameor.gnm1.ann1.Psat2g013520 | *Pisum sativum* |
| CcRpp2-R1Gm1 | 13 | 29 | 67.64 | 93B86 | Internal | *Glycine max* |
| CcRpp2-R1Gm2 | 13 | 29 | 67.64 | 93Y21 | Internal | *Glycine max* |
| CcRpp2-R1Gm3 | 13 | 29 | 67.64 | Wm82 | glyma.Wm82.gnm2.ann1.Glyma.14G024400.1 gene = glyma.Glyma.14G024400 | *Glycine max* |
| CcRpp2-R1Tp | 14 | 30 | 34.02 | Milvus | tripr.MilvusB.gnm2.ann1.mRNA23019 gene = tripr.gene22257 | *Trifolium pratense* |
| CcRpp2-R1Va* | 15 | 31 | 60.11 | Gyeongwon | vigan.Gyeongwon.gnm3.ann1.Vang01g02730.1 gene = vigan.Vang01g02730 | *Vigna angularis* |
| CcRpp2-R1Vr | 16 | 32 | 61.00 | VC1973A | vigra.VC1973A.gnm6.ann1.Vradi06g01780.1 gene = vigra.Vradi06g01780 | *Vigna radiata* |
| CcRpp2-R1Ps2 | 17 | 33 | 25.51 | PI220189 | Internal | *Pisum sativum* |
| CcRpp2-R1Pv2 | 18 | 34 | 58.95 | PI173046 | Internal | *Phaseolus vulgaris* |
| CcRpp2-R1Gm4 | 19 | 35 | 64.81 | Zh13 | glyma.Zh13.gnm1.ann1.SoyZH13__14G022300.m1 gene = glyma.Zh13.gnm1.ann1.SoyZH13__14G022300 | *Glycine max* |
| CcRpp2-R1Gm5 | 20 | 36 | 65.99 | Lee | glyma.Lee.gnm1.ann1.GlymaLee.14G022100.1 gene = glyma.Lee.gnm1.ann1.GlymaLee.14G022100 | *Glycine max* |
| CcRpp2-R1Gs2 | 13 | 29 | 67.64 | W05 | glyso.W05.gnm1.ann1.Glysoja.14G037482.1 gene = glyso.W05.gnm1.ann1.Glysoja.14G037482 | |

*may also function as an CcRpp2-R3 polypeptide

TABLE 4

CcRpp2-R3Aa homologous proteins and their origins

| Reference | NT SEQ ID NO | AA SEQ ID NO | Percent Amino Acid Sequence Identity to full length CcRpp2-R3Aa (SEQ ID NO: 4) | Variety | Public Database Gene Reference | Source Organism |
|---|---|---|---|---|---|---|
| CcRpp2-R3Aa | 3 | 4 | — | — | — | *Cajanus cajan* |
| CcRpp2-R3Ad* | 5 | 21 | 43.84 | V14167 | aradu.V14167.gnm1.ann1.Aradu.L0FGB.1 gene = aradu.Aradu.L0FGB | *Arachis duranensis* |

TABLE 4-continued

CcRpp2-R3Aa homologous proteins and their origins

| Reference | NT SEQ ID NO | AA SEQ ID NO | Percent Amino Acid Sequence Identity to full length CcRpp2-R3Aa (SEQ ID NO: 4) | Variety | Public Database Gene Reference | Source Organism |
|---|---|---|---|---|---|---|
| CcRpp2-R3Ah* | 6 | 22 | 45.10 | Tifrunner | arahy.Tifrunner.gnm2.ann1.SGE08U.1 gene = arahy.SGE08U | *Arachis hypogaea* |
| CcRpp2-R3Ai* | 6 | 22 | 45.10 | K30076 | araip.K30076.gnm1.ann1.Araip.FPQ85.1 gene = araip.Araip.FPQ85 | *Arachis ipaensis* |
| CcRpp2-R3Cc* | 7 | 23 | 73.55 | ICPL87119 | cajca.ICPL87119.gnm1.ann1.C.cajan__05869.1 gene = cajca.C.cajan__05869 | *Cajanus cajan* |
| CcRpp2-R3Cc2* | 8 | 24 | 45.55 | ISC453364 | cerca.ISC453364.gnm1.ann1.Cerca571S26910 | *Cercis canadensis* |
| CcRpp2-R3Gs1 | 37 | 48 | 66.91 | PI483463 | glyso.PI483463.gnm1.ann1.GlysoPI483463.14G021800.1 gene = glyso.PI483463.gnm1.ann1.GlysoPI483463.14G021800 | *Glycine soja* |
| CcRpp2-R1Mt* | 10 | 26 | 60.74 | A17 | medtr.A17__HM341.gnm4.ann2.Medtr5g092630.1 gene = medtr.A17__HM341.Medtr5g092630 | *Medicago truncatula* |
| CcRpp2-R3Pv1 | 38 | 49 | 65.70 | G19833 | >phavu.G19833.gnm2.ann1.Phvul.008G267600.1 gene = phavu.Phvul.008G267600 | *Phaseolus vulgaris* |
| CcRpp2-R3Ps1 | 39 | 50 | 29.07 | VC1973A | pissa.Cameor.gnm1.ann1.Psat2g013440.1 gene = pissa.Cameor.gnm1.ann1.Psat2g013440; | *Pisum sativum* |
| CcRpp2-R3Gm1 | 40 | 51 | 64.83 | 93B86 | [INTERNAL] >1765.dpgm014g604650.11.2 gene = dpgm014g604650.11 | *Glycine max* |
| CcRpp2-R3Gm2 | 41 | 52 | 67.15 | 93Y21 | [INTERNAL] >3441.dpgm14g481120.646.1 gene = dpgm14g481120.646 | *Glycine max* |
| CcRpp2-R3Gm3 | 41 | 52 | 67.15 | Wm82 | >glyma.Wm82.gnm2.ann1.Glyma.14G024500.1 gene = glyma.Glyma.14G024500 | *Glycine max* |
| CcRpp2-R1Va* | 15 | 31 | 48.26 | Gyeongwon | vigan.Gyeongwon.gnm3.ann1.Vang01g02730.1 gene = vigan.Vang01g02730 | *Vigna angularis* |
| CcRpp2-R3Vr | 42 | 53 | 67.73 | VC1973A | >vigra.VC1973A.gnm6.ann1.Vradi06g01790.1 gene = vigra.Vradi06g01790 | *Vigna radiata* |
| CcRpp2-R3Ps2 | 43 | 54 | 21.22 | PI220189 | [INTERNAL] >g56190.t1 gene = g56190 | *Pisum sativum* |
| CcRpp2-R3Pv2 | 44 | 55 | 64.82 | PI173046 | [INTERNAL] >g61862.t1 gene = g61862 | *Phaseolus vulgaris* |
| CcRpp2-R3Gm4 | 45 | 56 | 65.70 | Zh13 | >glyma.Zh13.gnm1.ann1.SoyZH13__14G022200.m1 gene = glyma.Zh13.gnm1.ann1.SoyZH13__14G022200 | *Glycine max* |
| CcRpp2-R3Gm5 | 46 | 57 | 66.87 | Lee | >glyma.Lee.gnm1.ann1.GlymaLee.14G022200.1 gene = glyma.Lee.gnm1.ann1.GlymaLee.14G022200 | *Glycine max* |
| CcRpp2-R3Gs2 | 47 | 58 | 66.87 | W05 | >glyso.W05.gnm1.ann1.Glysoja.14G037483.1 gene = glyso.W05.gnm1.ann1.Glysoja.14G037483 | *Glycine soja* |

*may also function as an CcRpp2-R1 polypeptide

The above description of various illustrated embodiments of the disclosure is not intended to be exhaustive or to limit the scope to the precise form disclosed. While specific embodiments of and examples are described herein for illustrative purposes, various equivalent modifications are possible within the scope of the disclosure, as those skilled in the relevant art will recognize. The teachings provided herein can be applied to other purposes, other than the examples described above. Numerous modifications and variations are possible in light of the above teachings and, therefore, are within the scope of the appended claims.

The entire disclosure of each document cited (including patents, patent applications, journal articles, abstracts, manuals, books or other disclosures) in the Background, Detailed Description, and Examples is herein incorporated by reference in their entireties.

Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight; temperature is in degrees Celsius; and pressure is at or near atmospheric.

What is claimed is:

1. A legume plant cell comprising an exogenous polynucleotide that encodes a polypeptide having at least 95% sequence identity with a full length sequence of SEQ ID NO: 2 or SEQ ID NO: 4, or a plant or plant part comprising a plurality of said legume plant cells.

2. The legume plant cell, plant, or plant part of claim 1, further comprising an exogenous polynucleotide that encodes a polypeptide having the sequence of SEQ ID NO: 60 or a sequence having at least 95% sequence identity to SEQ ID NO: 60.

3. The legume plant cell, plant or plant part of claim 1, wherein the legume plant cell, plant or plant part is a soybean plant cell, plant or plant part.

4. The legume plant cell, plant, or plant part of claim 1, wherein the exogenous polynucleotide encodes (i) a first polypeptide having at least 95% sequence identity with the full length sequence of SEQ ID NO: 2 and (ii) a second polypeptide having at least 95% sequence identity with the full length sequence of SEQ ID NO: 4.

5. The legume plant cell, plant, or plant part of claim 1, wherein the plant cell, plant, or plant part comprises a first exogenous polynucleotide that encodes the polypeptide having at least 95% sequence identity with the full length sequence of SEQ ID NO: 2 and a second exogenous polynucleotide that encodes the polypeptide having at least 95% sequence identity with the full length sequence of SEQ ID NO: 4.

6. The legume plant cell, plant, or plant part of claim 1, wherein the exogenous polynucleotide is an expression construct comprising a sequence having at least 95% sequence identity with the full length sequence of SEQ ID NO: 1 or SEQ ID NO: 3, which is operably linked to a heterologous regulatory sequence operable in plant cells.

7. The legume plant cell, plant, or plant part of 6, wherein the expression construct comprises a first polynucleotide having at least 95% sequence identity with the full length sequence of SEQ ID NO: 1 and a second polynucleotide having at least 95% sequence identity with the full length sequence of SEQ ID NO: 3, wherein each of said first and second polynucleotides are operably linked to a heterologous regulatory sequence operable in plant cells.

8. The legume plant cell, plant, or plant part of claim 6, wherein the plant cell, plant, or plant part comprises a first expression construct comprising the first polynucleotide having at least 95% sequence identity with the full length sequence of SEQ ID NO: 1 and a second expression cassette comprising the second polynucleotide having at least 95% sequence identity with the full length sequence of SEQ ID NO: 3, wherein each of said first and second polynucleotides are operably linked to a heterologous regulatory sequence operable in plant cells.

9. The legume plant cell, plant, or plant part of claim 1, wherein the polypeptide has at least 98% sequence identity with the full length sequence of SEQ ID NO: 2 or SEQ ID NO: 4.

10. The transgenic legume plant cell, plant, or plant part of claim 4, wherein the first polypeptide has at least 98% sequence identity with the full length sequence of SEQ ID NO: 2 and the second polypeptide has at least 98% sequence identity with the full length sequence of SEQ ID NO: 4.

11. The transgenic legume plant cell, plant, or plant part of claim 4, wherein the first polypeptide comprises SEQ ID NO: 2 and the second polypeptide comprises SEQ ID NO: 4.

12. A soybean seed comprising a plurality of the transgenic legume plant cells of claim 1.

13. A soybean seed comprising a plurality of the transgenic legume plant cells of claim 2.

14. A soybean seed comprising a plurality of the transgenic legume plant cells of claim 4.

15. A soybean seed comprising a plurality of the transgenic legume plant cells of claim 5.

16. A soybean seed comprising a plurality of the transgenic legume plant cells of claim 6.

17. A soybean seed comprising a plurality of the transgenic legume plant cells of claim 7.

18. A soybean seed comprising a plurality of the transgenic legume plant cells of claim 8.

19. A soybean seed comprising a plurality of the transgenic legume plant cells of claim 9.

20. A soybean seed comprising a plurality of the transgenic legume plant cells of claim 10.

21. A soybean seed comprising a plurality of the transgenic legume plant cells of claim 11.

\*   \*   \*   \*   \*